United States Patent
Kosugi et al.

(10) Patent No.: US 11,786,444 B2
(45) Date of Patent: *Oct. 17, 2023

(54) DENTAL POLYFUNCTIONAL MONOMERS AND DENTAL HYDROXYL GROUP-CONTAINING MONOMERS

(71) Applicant: MITSUI CHEMICALS, INC., Tokyo (JP)

(72) Inventors: Yoko Kosugi, Ichihara (JP); Akiko Matsumoto, Narashino (JP); Kazuhiko Yoshinaga, Ichihara (JP)

(73) Assignee: MITSUI CHEMICALS, INC., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 17/408,804

(22) Filed: Aug. 23, 2021

(65) Prior Publication Data

US 2021/0378919 A1  Dec. 9, 2021

Related U.S. Application Data

(62) Division of application No. 16/485,612, filed as application No. PCT/JP2018/013236 on Mar. 29, 2018, now abandoned.

(30) Foreign Application Priority Data

Mar. 31, 2017 (JP) ................... 2017-072677
Mar. 31, 2017 (JP) ................... 2017-072678

(51) Int. Cl.
| | |
|---|---|
| *A61K 6/887* | (2020.01) |
| *C07C 271/16* | (2006.01) |
| *A61K 6/40* | (2020.01) |
| *C07C 275/10* | (2006.01) |
| *A61K 6/30* | (2020.01) |

(52) U.S. Cl.
CPC ............ *A61K 6/887* (2020.01); *A61K 6/30* (2020.01); *A61K 6/40* (2020.01); *C07C 271/16* (2013.01); *C07C 275/10* (2013.01)

(58) Field of Classification Search
None
See application file for complete search history.

(56) References Cited

U.S. PATENT DOCUMENTS

| | | | | |
|---|---|---|---|---|
| 4,287,323 | A | * | 9/1981 | Tefertiller ............ C08G 18/635 525/55 |
| 4,859,780 | A | | 8/1989 | Molock et al. |
| 2004/0077754 | A1 | | 4/2004 | Moszner et al. |
| 2005/0124721 | A1 | | 6/2005 | Arthur et al. |
| 2008/0076043 | A1 | | 3/2008 | Mori et al. |
| 2010/0022682 | A1 | | 1/2010 | Klee et al. |
| 2010/0056665 | A1 | | 3/2010 | Sekiguchi |
| 2011/0207086 | A1 | | 8/2011 | Yang et al. |
| 2012/0129973 | A1 | | 5/2012 | Sun |
| 2015/0196462 | A1 | | 7/2015 | Sun |
| 2017/0174621 | A1 | | 6/2017 | Yoshinaga et al. |
| 2017/0181932 | A1 | | 6/2017 | Yoshinaga et al. |
| 2019/0365610 | A1 | | 12/2019 | Kosugi et al. |
| 2021/0161771 | A1 | | 6/2021 | Kosugi et al. |

FOREIGN PATENT DOCUMENTS

| | | |
|---|---|---|
| CN | 105801795 A | 7/2016 |
| CN | 105859584 A | 8/2016 |
| CN | 105859585 A | 8/2016 |
| CN | 105859587 A | 8/2016 |
| CN | 105860026 A | 8/2016 |
| CN | 105860028 A | 8/2016 |
| EP | 1 449 650 A2 | 8/2004 |
| JP | 2000204069 A | 7/2000 |
| JP | 2008088251 A | 4/2008 |
| JP | 2010505895 A | 2/2010 |
| JP | 2010150290 A | 7/2010 |
| JP | 2013133290 A | 7/2013 |
| JP | 2013544823 A | 12/2013 |
| WO | 2015152220 A1 | 10/2015 |
| WO | 2015152221 A1 | 10/2015 |

OTHER PUBLICATIONS

PubChem (National Center for Biotechnology Information. "PubChem Compound Summary for CID 32881, 2-(2-Hydroxypropoxy) propan-1-ol" PubChem, https://pubchem.ncbi.nlm.nih.gov/compound/2-_2-Hydroxypropoxy_propan-1-ol. Accessed Dec. 21, 2022) (Year: 2022).*
Moszner ("New Diluents for Dental Composites" Macromolecular Materials and Engineering, 2016, p. 750-759). (Year: 2016).*
International Search Report (PCT/ISA/210) and translation and Written Opinion (PCT/ISA/237) dated Jul. 3, 2018, by the Japanese Patent Office as the International Searching Authority for International Application No. PCT/JP2018/013236.

* cited by examiner

*Primary Examiner* — Amy C Bonaparte
(74) *Attorney, Agent, or Firm* — BUCHANAN INGERSOLL & ROONEY PC

(57) ABSTRACT

Provided are monomers useful for dental materials that include a compound in which a core and a specific terminal group are bonded to each other directly or via a linking group, wherein the core is a $C_{1-200}$ polyvalent organic group having a valence of not less than 3 containing an oxygen atom or a nitrogen atom in which an atom bonded to the terminal group or the linking group is the oxygen atom or the nitrogen atom; the terminal group is a specific (meth)acryloyl group-containing group, a (meth)acryloyl group, a $C_{1-20}$ hydrocarbon group or a hydrogen atom, and the terminal group needs to meet specific requirements; and the linking group is a specific divalent group, and when the compound contains a plurality of linking groups, the linking groups may be the same as or different from each other. Compositions, dental materials and kits are also provided.

20 Claims, No Drawings

DENTAL POLYFUNCTIONAL MONOMERS AND DENTAL HYDROXYL GROUP-CONTAINING MONOMERS

CROSS-REFERENCE TO RELATED APPLICATIONS

This application is a division of U.S. patent application Ser. No. 16/485,612, filed on Aug. 13, 2019, now abandoned, which is a national stage of International Patent Application No. PCT/JP2018/013236 filed on Mar. 29, 2018, which in turn claims priority to Japanese Patent Application No. 2017-072677, filed on Mar. 31, 2017, and Japanese Patent Application No. 2017-072678, filed on Mar. 31, 2017, the entire disclosures of all of which are incorporated herein by reference.

TECHNICAL FIELD

The present invention relates to dental polyfunctional monomers, dental materials including the monomers, cured products of the dental materials, and kits including the dental materials. The present invention also relates to dental hydroxyl group-containing monomers, dental materials including the monomers, cured products of the dental materials, and kits including the dental materials.

BACKGROUND ART

In the dental clinical practice, the use of resin-based materials has been expanding. However, the mechanical properties of the resin-based materials are still insufficient. In particular, the poor strength obstructs the application of the resin-based materials to sites subjected to a high stress.

Many of the resin-based dental materials contain a monomer having a (meth)acrylate group in the molecular structure. Typical examples of monomers for dental materials include bisphenol A diglycidyl methacrylate (Bis-GMA), and dimethacrylates having methacrylic groups at both terminals, such as 2,2,4-trimethylhexamethylenebis(2-carbamoyloxyethyl) dimethacrylate (UDMA) and triethylene glycol dimethacrylate (TEGDMA).

In recent years, attempts have been made to enhance the mechanical strength of cured products of composite resins as base monomers to be used for dental materials (see, for example, Patent Literatures 1 and 2). Some of these compositions have been reported to be usable for dental products in view of their mechanical properties. Further, in recent years, it has been reported that introduction of rigid groups into monomers enhances the strength of dental resins (see, for example, Patent Literature 3 and Patent Literature 4).

Further, it has been reported that (meth)acrylate groups present in conventional resin-based dental materials are difficult to fully polymerize, and the polymerization rate reaches only a moderate value (see, for example, Non-Patent Literature 1). Presence of unpolymerized (meth)acrylate groups concerned are presumed to adversely affect the mechanical properties of the cured products, and may cause unpolymerized monomers to leach from the cured products.

2-Hydroxyethyl methacrylate (hereinafter, written as HEMA) has a hydroxyl group and a polymerizable group in the molecule, molecular hydrophilicity derived from the hydroxyl group is considered to be beneficial for tooth compatibility and tooth surface modification, and polymerizability is beneficial for integration with a resin matrix. Such properties of HEMA are useful for primers, and HEMA is widely used particularly for dental primers and dental bonding materials in the field of dental materials (see, for example, Non-Patent Literature 2).

In recent years, attempts to make an improvement in HEMA have been reported. For example, a composition containing a compound in which some of hydroxyl groups of trehalose are converted into polymerizable groups has been reported to exhibit high bonding performance (see, for example, Patent Literature 5).

Further, a compound having a sulfonate group and a (meth)acrylamide group in the molecule (see, for example, Patent Literature 6), a compound having a hydroxyl group and a (meth)acrylamide group in the molecule (see, for example, Patent Literature 7), and the like have been proposed.

CITATION LIST

Patent Literature

Patent Literature 1: JP-A-2000-204069
Patent Literature 2: JP-W-2013-544823
Patent Literature 3: WO 2015/152220
Patent Literature 4: WO 2015/152221
Patent Literature 5: JP-A-2013-133290
Patent Literature 6: JP-W-2010-505895
Patent Literature 7: JP-A-2010-150290

Non-Patent Literature

Non-Patent Literature 1: Cynthia J. E. Floyd et al., Network structure of Bis-GMA- and UDMA-based resin systems, Dental Materials, 22, 2006, pp. 1143-1149
Non-Patent Literature 2: Yoshihiro Nishitani et al., Effects of resin hydrophilicity on dentin bonds, Adhesive Dentistry, 26, 2008, pp. 92-98

SUMMARY OF INVENTION

Technical Problem

An object of the present invention is to provide monomers useful for dental materials, compositions, dental materials, kits and the like. Further, objects of a first aspect and a second aspect are as follows.

In view of the above-described problems, objects of the first aspect of the present invention are to provide dental polyfunctional monomers that can give cured products having high strength, and to provide cured products of the dental polyfunctional monomers. Further, an object of the first aspect of the present invention is to provide dental materials including the dental polyfunctional monomers and having a low residual ratio of unreacted polymerizable terminals after curing.

Further enhancement of adhesiveness to the tooth is desired. In view of the above-described problems, an object of the second aspect of the present invention is to provide dental hydroxyl group-containing monomers having the function of enhancing adhesive strength with the tooth in dental treatment.

Solution to Problem

The present inventors have conducted studies for solving the above-described problems, and as a resultant found that a polyfunctional monomer containing a (meth)acryloyl group can be produced by reaction of a polyhydric alcohol or a polyol with a (meth)acryloyl group-containing isocyanate compound, a cured product of a composition including the polyfunctional monomer containing a (meth)acryloyl group exhibits high strength, and the composition including the polyfunctional monomer containing a (meth)acryloyl group exhibits a high polymerization rate in curing. Consequently, the first aspect of the present invention has been completed.

Further, the present inventors have conducted studies for solving the above-described problems, and as a resultant found that a monomer containing a hydroxyl group and a (meth)acryloyl group can be produced by reaction of a polyhydric alcohol or a polyol with a (meth)acryloyl group-containing isocyanate compound, and adhesiveness of a dental material including the monomer containing a hydroxyl group and a (meth)acryloyl group to the tooth is enhanced. Consequently, the second aspect of the present invention has been completed.

The first aspect of the present invention includes the subject matters described in [1A] to [23A] below.

[1A]

A dental polyfunctional monomer comprising a compound represented by the general formula (8A) below, in which the core (X) below and the terminal group (Y2A) below are bonded to each other directly or via the linking group (Z) below:

[Chem. 1]

$$X(Y2A)n^{8aA}(Z—Y2A)n^{8bA} \tag{8A}$$

(in the general formula (8A), $n^{8aA}$ represents the number of terminal groups (Y2A) directly bonded to the core (X), $n^{8bA}$ represents the number of terminal groups (Y2A) bonded to the core (X) via the linking group (Z), and the sum of $n^{8aA}$ and $n^{8bA}$ is equal to the valence of the core (X);

the core (X) is a $C_{1-200}$ polyvalent organic group having a valence of not less than 3 containing an oxygen atom or a nitrogen atom in which an atom bonded to the terminal group (Y2A) or the linking group (Z) is the oxygen atom or the nitrogen atom;

the terminal group (Y2A) is a (meth)acryloyl group-containing group (Y3) represented by the general formula (9) below, a (meth)acryloyl group or a $C_{1-20}$ hydrocarbon group, and a plurality of terminal groups (Y2A) may be the same as or different from each other, with the proviso that among all the terminal groups (Y2A) in the compound represented by the general formula (8A), three or more terminal groups are (meth)acryloyl group-containing groups (Y3) or (meth)acryloyl groups, and one or more terminal groups are (meth)acryloyl group-containing groups (Y3); and the linking group (Z) is a divalent group represented by the general formula (2) below, and when the compound represented by the general formula (8A) contains a plurality of linking groups (Z), the linking groups (Z) may be the same as or different from each other);

[Chem. 2]

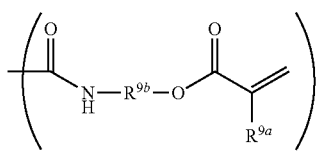
(9)

(in the general formula (9), $R^{9a}$ represents a hydrogen atom or a methyl group, $R^{9b}$ represents a $C_{2-6}$ linear alkylene group or a $C_{2-6}$ linear oxyalkylene group, and the linear alkylene group or the linear oxyalkylene group is optionally substituted with a $C_{1-6}$ alkyl group or a (meth)acryloyloxymethylene group in place of a hydrogen atom); and

[Chem. 3]

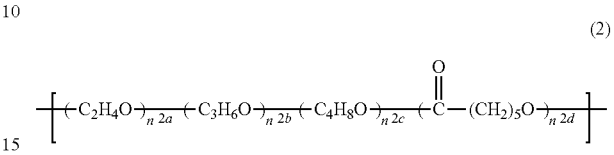
(2)

(in the general formula (2), $n^{2a}$, $n^{2b}$, $n^{2c}$ and $n^{2d}$ represent the unit numbers of respective repeating units, and are each 0 to 100, the sum of $n^{2a}$, $n^{2b}$, $n^{2c}$ and $n^{2d}$ is 1 to 100, the left end of the group is bonded to the core (X), and the right end of the group is bonded to the terminal group (Y2A)).

[2A]

The dental polyfunctional monomer according to [1A], wherein the terminal group (Y2A) is a (meth)acryloyl group-containing group (Y3) or a (meth)acryloyl group.

[3A]

The dental polyfunctional monomer according to [1A] or [2A], wherein the terminal group (Y2A) is a (meth)acryloyl group-containing group (Y3).

[4A]

The dental polyfunctional monomer according to any of [1A] to [3A], wherein in the linking group (Z) $n^{2a}$, $n^{2b}$, $n^{2c}$ and $n^{2d}$ are each 0 to 20, and the sum of $n^{2a}$, $n^{2b}$, $n^{2c}$ and $n^{2d}$ is 1 to 20.

[5A]

The dental polyfunctional monomer according to any of [1A] to [4A], wherein the linking group (Z) is a divalent group represented by the general formula (4) below:

[Chem. 4]

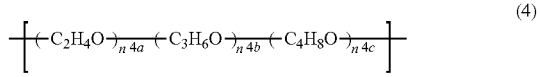
(4)

(in the general formula (4), $n^{4a}$, $n^{4b}$ and $n^{4c}$ represent the unit numbers of respective repeating units, and are each 0 to 20, the sum of $n^{4a}$, $n^{4b}$ and $n^{4c}$ is 1 to 20, the left end of the group is bonded to the core (X), and the right end of the group is bonded to the terminal group (Y2A)).

[6A]

The dental polyfunctional monomer according to any of [1A] to [5A], wherein the linking group (Z) is a divalent group represented by the general formula (5) below:

[Chem. 5]

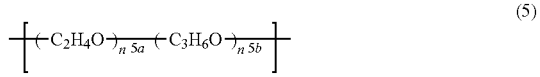
(5)

(in the general formula (5), $n^{5a}$ and $n^{5b}$ represent the unit numbers of respective repeating units, and are each 0 to 20, the sum of $n^{5a}$ and $n^{5b}$ is 1 to 20, the left end of the group is bonded to the core (X), and the right end of the group is bonded to the terminal group (Y2A)).

[7A]

The dental polyfunctional monomer according to any of [1A] to [6A], wherein the core (X) is an organic group having a valence of 3 to 12.

[8A]

The dental polyfunctional monomer according to any of [1A] to [7A], wherein the core (X) is at least one selected from the group consisting of groups represented by the general formulas (6a) to (6j) below:

[Chem. 6]

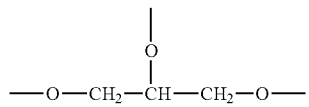
(6a)

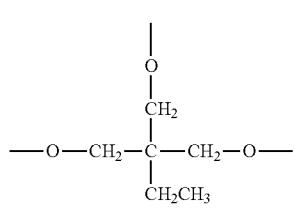
(6b)

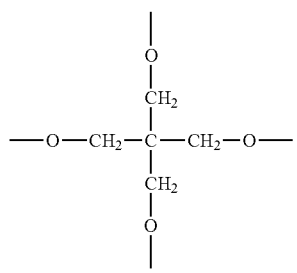
(6c)

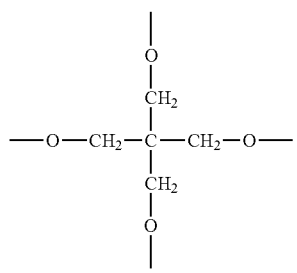
(6d)

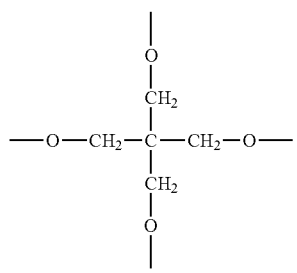
(6e)

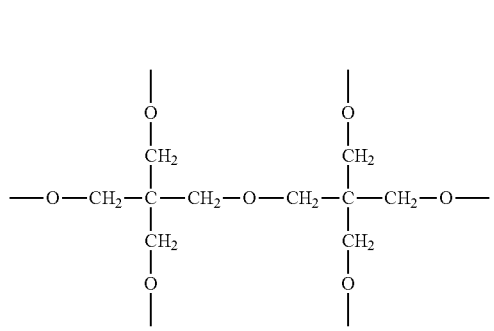

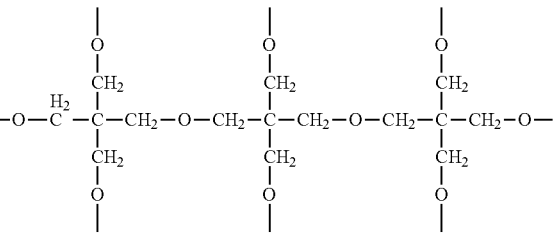
(6f)

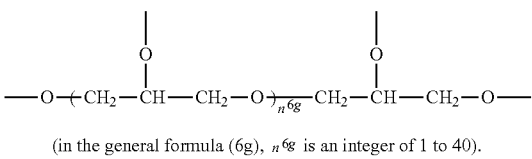
(6g)

(in the general formula (6g), $n^{6g}$ is an integer of 1 to 40).

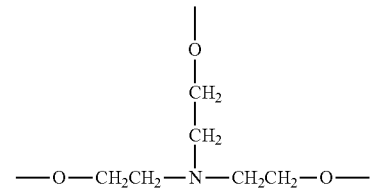
(6h)

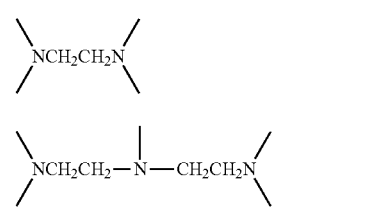
(6i)

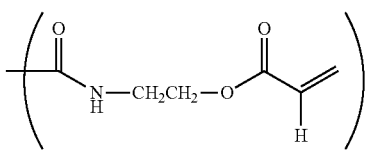
(6j)

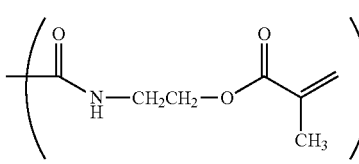

[9A]

The dental polyfunctional monomer according to any of [1A] to [8A], wherein the (meth)acryloyl group-containing group (Y3) is at least one selected from the group consisting of groups represented by the general formulas (9a) to (9f) below:

[Chem. 7]

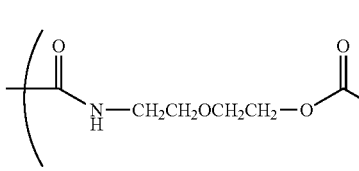
(9a)

(9b)

(9c)

(9d)

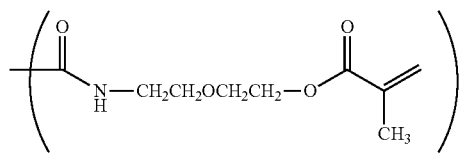

(9e)

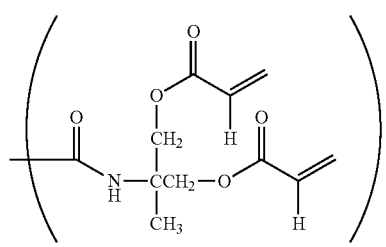

(9f)

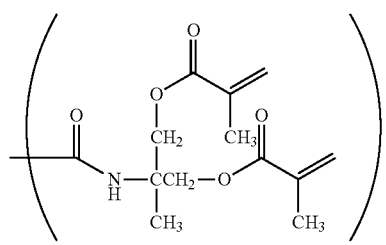

[10A]

A dental polyfunctional monomer which is a product of reaction of a compound represented by the general formula (1A) below, in which the core (X) below and the terminal group (Y1A) below are bonded to each other directly or via the linking group (Z) below, with a (meth)acryloyl group-containing isocyanate compound represented by the general formula (3) below, under a condition of (the number of isocyanate groups present in the compound represented by the general formula (3) below)/(the number of active protons bonded to oxygen atoms and nitrogen atoms present in the compound represented by the general formula (1A) below) =1:

[Chem. 8]

$$X(Y1A)n^{1aA}(z\text{-}Y1A)n^{1bA} \quad (1A)$$

(in the general formula (1A), $n^{1aA}$ represents the number of terminal groups (Y1A) directly bonded to the core (X), $n^{1bA}$ represents the number of terminal groups (Y1A) bonded to the core (X) via the linking group (Z), and the sum of $n^{1aA}$ and $n^{1bA}$ is equal to the valence of the core (X);

the core (X) is a $C_{1\text{-}200}$ polyvalent organic group having a valence of not less than 3 containing an oxygen atom or a nitrogen atom in which an atom bonded to the terminal group (Y1A) or the linking group (Z) is the oxygen atom or the nitrogen atom;

the terminal group (Y1A) is a (meth)acryloyl group, a $C_{1\text{-}20}$ monovalent hydrocarbon group or a hydrogen atom, and a plurality of terminal groups (Y1A) may be the same as or different from each other, with the proviso that among the terminal groups (Y1A) in the compound represented by the general formula (1A), three or more terminal groups are hydrogen atoms or (meth)acryloyl groups, and one or more terminal groups are hydrogen atoms; and the linking group (Z) is a divalent group represented by the general formula (2) below, and when the compound represented by the general formula (1A) contains a plurality of linking groups (Z), the linking groups (Z) may be the same as or different from each other);

[Chem. 9]

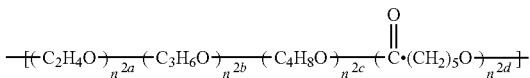

(2)

(in the general formula (2), $n^{2a}$, $n^{2b}$, $n^{2c}$ and $n^{2d}$ represent the unit numbers of respective repeating units, and are each 0 to 100, the sum of $n^{2a}$, $n^{2b}$, $n^{2c}$ and $n^{2d}$ is 1 to 100, the left end of the group is bonded to the core (X), and the right end of the group is bonded to the terminal group (Y1A)); and

[Chem. 10]

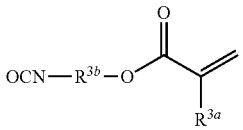

(3)

(in the general formula (3), $R^{3a}$ represents a hydrogen atom or a methyl group, $R^{3b}$ represents a $C_{2\text{-}6}$ linear alkylene group or a $C_{2\text{-}6}$ linear oxyalkylene group, and the linear alkylene group or the linear oxyalkylene group is optionally substituted with a $C_{1\text{-}6}$ alkyl group or a (meth)acryloyloxymethylene group in place of a hydrogen atom)

[11A]

The dental polyfunctional monomer according to [10A], wherein the terminal group (Y1A) is a hydrogen atom.

[12A]

The dental polyfunctional monomer according to [10A] or [11A], wherein in the linking group (Z) $n^{2a}$, $n^{2b}$, $n^{2c}$ and $n^{2d}$ are each 0 to 20, and the sum of $n^{2a}$, $n^{2b}$, $n^{2c}$ and $n^{2d}$ is 1 to 20.

[13A]

The dental polyfunctional monomer according to any of [10A] to [12A], wherein the linking group (Z) is a divalent group represented by the general formula (4) below:

[Chem. 11]

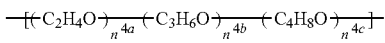

(4)

(in the general formula (4), $n^{4a}$, $n^{4b}$ and $n^{4c}$ represent the unit numbers of respective repeating units, and are each 0 to 20, the sum of $n^{4a}$, $n^{4b}$ and $n^{4c}$ is 1 to 20, the left end of the group is bonded to the core (X), and the right end of the group is bonded to the terminal group (Y1A)).

[14A]

The dental polyfunctional monomer according to any of [10A] to [13A], wherein the linking group (Z) is a divalent group represented by the general formula (5) below:

[Chem. 12]

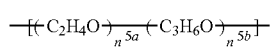   (5)

(in the general formula (5), $n^{5a}$ and $n^{5b}$ represent the unit numbers of respective repeating units, and are each 0 to 20, the sum of $n^{5a}$ and $n^{5b}$ is 1 to 20, the left end of the group is bonded to the core (X), and the right end of the group is bonded to the terminal group (Y1A)).

[15A]

The dental polyfunctional monomer according to any of [10A] to [14A], wherein the core (X) is an organic group having a valence of 3 to 12.

[16A]

The dental polyfunctional monomer according to any of [10A] to [15A], wherein the compound (1A) is at least one selected from the group consisting of compounds represented by the general formulas (6'a) to (6'k) below:

[Chem. 13]

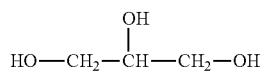   (6'a)

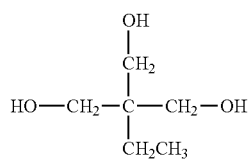   (6'b)

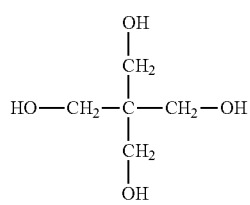   (6'c)

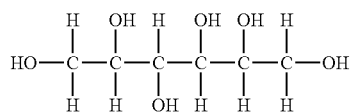   (6'd)

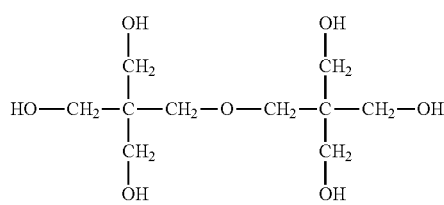   (6'e)

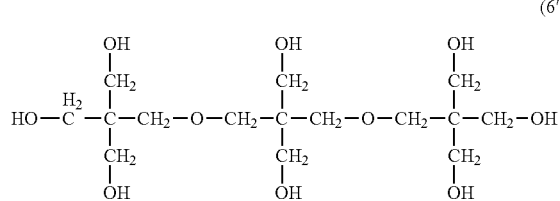   (6'f)

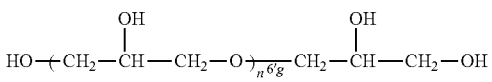   (6'g)

(in the general formula (6g), $n^{6'g}$ is an integer of 1 to 40)

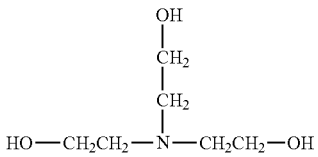   (6'h)

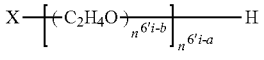   (6'i)

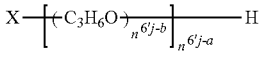   (6'j)

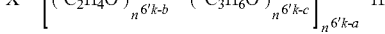   (6'k)

($n^{6'i-a}$, $n^{6'j-a}$ and $n^{6'k-a}$ in the general formulas (6'i), (6'j) and (6'k) each represent the number of arms of a polyol bonded to the core (X), and are each an integer of not less than 3; and $n^{6'i-b}$ and $n^{6'j-b}$ in the general formulas (6'i) and (6'j) represent the numbers of oxyethylene units and oxypropylene units, respectively, and are each in the range of 1 to 100, the numbers of units for respective arms may be the same as or different from each other, $n^{6'k-b}$ and $n^{6'k-c}$ in the general formula (6'k) represent the numbers of oxyethylene units and oxypropylene units, respectively, the sum thereof is in the range of 1 to 100, and the sums of the numbers of units for respective arms may be the same as or different from each other).

[17A]

The dental polyfunctional monomer according to any of [10A] to [16A], wherein the (meth)acryloyl group-containing isocyanate compound represented by the general formula (3) is at least one selected from the group consisting of compounds represented by the general formulas (3a) to (3f) below:

[Chem. 14]

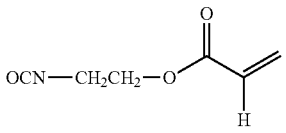   (3a)

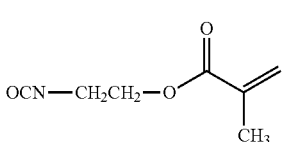   (3b)

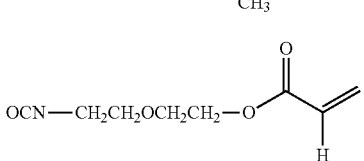   (3c)

(3d)

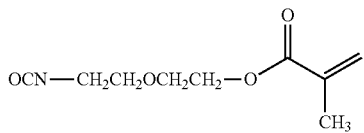

(3e)

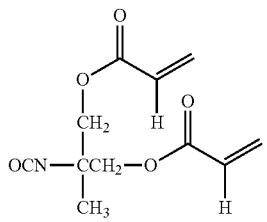

(3f)

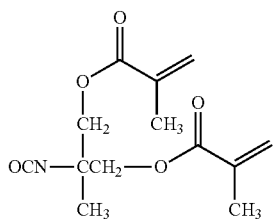

[18A]

A dental monomer composition comprising the dental polyfunctional monomer according to any of [1A] to [17A].

[19A]

The dental monomer composition according to [18A], wherein the dental monomer composition is negative in a reverse mutation test.

[20A]

A dental material comprising the dental polyfunctional monomer according to any of [1A] to [17A].

[21A]

The dental material according to [20A], wherein the dental material is negative in a reverse mutation test.

[22A]

A cured product obtained by curing the dental material according to [20A] or [21A].

[23A]

A kit comprising the dental material according to [20A] or [21A].

The second aspect of the present invention includes the subject matters described in [1B] to [21B] below.

[1B]

A dental hydroxyl group-containing monomer comprising a compound represented by the general formula (8B) below, in which the core (X) below and the terminal group (Y2B) below are bonded to each other directly or via the linking group (Z) below:

[Chem. 15]

$$X(Y2B)_{n^{8aB}}(Z-Y2B)_{n^{8bB}} \quad (8B)$$

(in the general formula (8B), $n^{8aB}$ represents the number of terminal groups (Y2B) directly bonded to the core (X), $n^{8bB}$ represents the number of terminal groups (Y2B) bonded to the core (X) via the linking group (Z), and the sum of $n^{8aB}$ and $n^{8bB}$ is equal to the valence of the core (X);

the core (X) is a $C_{1-200}$ polyvalent organic group having a valence of not less than 3 containing an oxygen atom or a nitrogen atom in which an atom bonded to the terminal group (Y2B) or the linking group (Z) is the oxygen atom or the nitrogen atom;

the terminal group (Y2B) is a (meth)acryloyl group-containing group (Y3) represented by the general formula (9) below, a (meth)acryloyl group, a $C_{1-20}$ hydrocarbon group or a hydrogen atom, and a plurality of terminal groups (Y2B) may be the same as or different from each other, with the proviso that among all the terminal groups (Y2B) in the compound represented by the general formula (8B), one or more terminal groups are (meth)acryloyl group-containing groups (Y3), and one or more terminal groups are hydrogen atoms; and the linking group (Z) is a divalent group represented by the general formula (2) below, and when the compound represented by the general formula (8B) contains a plurality of linking groups (Z), the linking groups (Z) may be the same as or different from each other);

[Chem. 16]

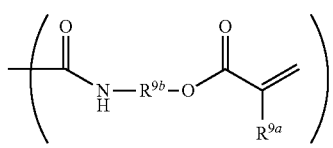

(9)

(in the general formula (9), $R^{9a}$ represents a hydrogen atom or a methyl group, $R^{9b}$ represents a $C_{2-6}$ linear alkylene group or a $C_{2-6}$ linear oxyalkylene group, and the linear alkylene group or the linear oxyalkylene group is optionally substituted with a $C_{1-6}$ alkyl group or a (meth)acryloyloxymethylene group in place of a hydrogen atom); and

[Chem. 17]

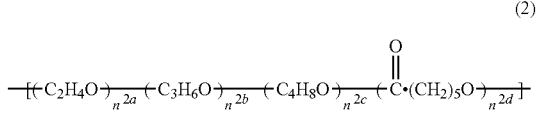

(2)

(in the general formula (2), $n^{2a}$, $n^{2b}$, $n^{2c}$ and $n^{2d}$ represent the unit numbers of respective repeating units, and are each 0 to 100, the sum of $n^{2a}$, $n^{2b}$, $n^{2c}$ and $n^{2d}$ is 1 to 100, the left end of the group is bonded to the core (X), and the right end of the group is bonded to the terminal group (Y2B)).

[2B]

The dental hydroxyl group-containing monomer according to [1B], wherein the terminal group (Y2B) is a (meth)acryloyl group-containing group (Y3) or a hydrogen atom.

[3B]

The dental hydroxyl group-containing monomer according to [1B] or [2B], wherein in the linking group (Z) $n^{2a}$, $n^{2b}$, $n^{2c}$ and $n^{2d}$ are each 0 to 20, and the sum of $n^{2a}$, $n^{2b}$, $n^{2c}$ and $n^{2d}$ is 1 to 20.

[4B]

The dental hydroxyl group-containing monomer according to any of [1B] to [3B], wherein the linking group (Z) is a divalent group represented by the general formula (4) below:

[Chem. 18]

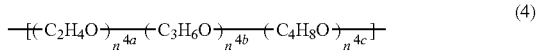

(4)

(in the general formula (4), $n^{4a}$, $n^{4b}$ and $n^{4c}$ represent the unit numbers of respective repeating units, and are each 0 to 20, the sum of $n^{4a}$, $n^{4b}$ and $n^{4c}$ is 1 to 20, the left end of the group is bonded to the core (X), and the right end of the group is bonded to the terminal group (Y2B)).

[5B]

The dental hydroxyl group-containing monomer according to any of [1B] to [4B], wherein the linking group (Z) is a divalent group represented by the general formula (5) below:

[Chem. 19]

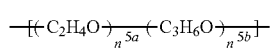
(5)

(in the general formula (5), $n^{5a}$ and $n^{5b}$ represent the unit numbers of respective repeating units, and are each 0 to 20, the sum of $n^{5a}$ and $n^{5b}$ is 1 to 20, the left end of the group is bonded to the core (X), and the right end of the group is bonded to the terminal group (Y2B)).

[6B]

The dental hydroxyl group-containing monomer according to any of [1B] to [5B], wherein the core (X) is an organic group having a valence of 3 to 12.

[7B]

The dental hydroxyl group-containing monomer according to any of [1B] to [6B], wherein the core (X) is at least one selected from the group consisting of groups represented by the general formulas (6a) to (6j) below:

[Chem. 20]

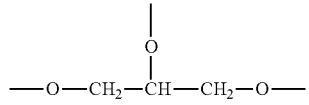
(6a)

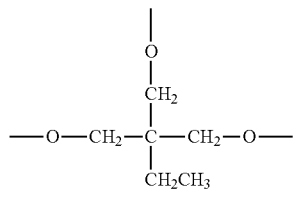
(6b)

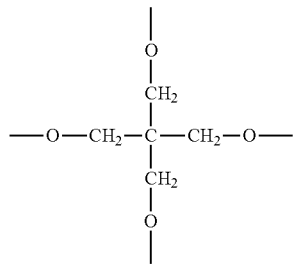
(6c)

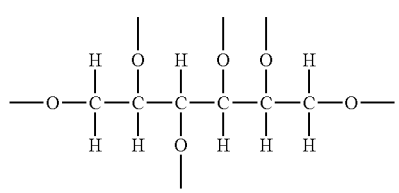
(6d)

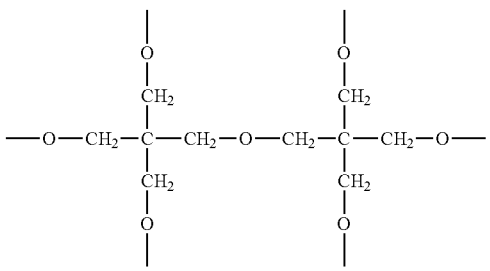
(6e)

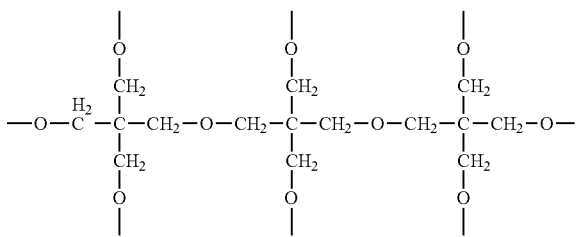
(6f)

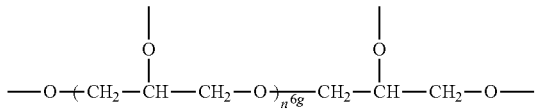
(6g)

(in the general formula (6g), $n^{6g}$ is an integer of 1 to 40).

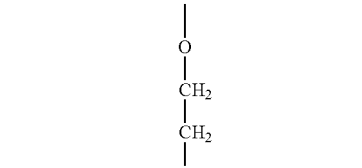
(6h)

(6i)

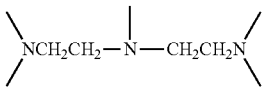
(6j)

[8B]

The dental hydroxyl group-containing monomer according to any of [1B] to [7B], wherein the (meth)acryloyl group-containing group (Y3) is at least one selected from the group consisting of groups represented by the general formulas (9a) to (9f) below:

[Chem. 21]

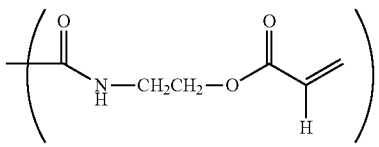
(9a)

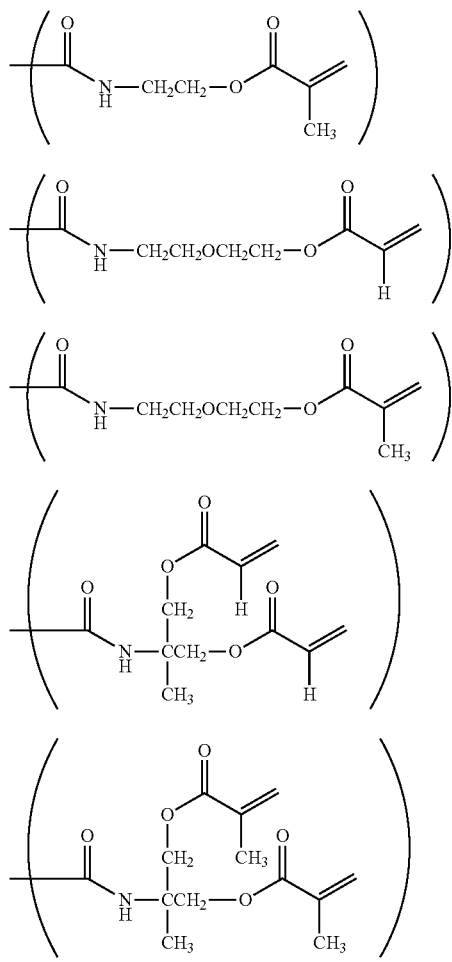

[9B]

A dental hydroxyl group-containing monomer which is a product of reaction of a compound represented by the general formula (1B) below, in which the core (X) below and the terminal group (Y1B) below are bonded to each other directly or via the linking group (Z) below, with a (meth)acryloyl group-containing isocyanate compound represented by the general formula (3) below, under a condition of 1/(the number of active protons bonded to oxygen atoms and nitrogen atoms present in the compound represented by the general formula (1B) below) (the number of isocyanate groups present in the compound represented by the general formula (3) below)/(the number of active protons bonded to oxygen atoms and nitrogen atoms present in the compound represented by the general formula (1B) below)<1:

[Chem. 22]

$$X(Y1B)_{n^{1aB}}(Z-Y1B)_{n^{1bB}} \quad (1B)$$

(in the general formula (1B), $n^{1aB}$ represents the number of terminal groups (Y1B) directly bonded to the core (X), $n^{1bB}$ represents the number of terminal groups (Y1B) bonded to the core (X) via the linking group (Z), and the sum of $n^{1aB}$ and $n^{1bB}$ is equal to the valence of the core (X);

the core (X) is a $C_{1-200}$ polyvalent organic group having a valence of not less than 3 containing an oxygen atom or a nitrogen atom in which an atom bonded to the terminal group (Y1B) or the linking group (Z) is the oxygen atom or the nitrogen atom;

the terminal group (Y1B) is a (meth)acryloyl group, a $C_{1-20}$ monovalent hydrocarbon group or a hydrogen atom, and a plurality of terminal groups (Y1B) may be the same as or different from each other, with the proviso that among the terminal groups (Y1B) in the compound represented by the general formula (1B), two or more terminal groups are hydrogen atoms; and the linking group (Z) is a divalent group represented by the general formula (2) below, and when the compound represented by the general formula (1B) contains a plurality of linking groups (Z), the linking groups (Z) may be the same as or different from each other);

[Chem. 23]

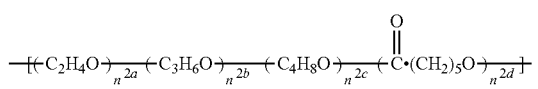

(2)

(in the general formula (2), $n^{2a}$, $n^{2b}$, $n^{2c}$ and $n^{2d}$ represent the unit numbers of respective repeating units, and are each 0 to 100, the sum of $n^{2a}$, $n^{2b}$, $n^{2c}$ and $n^{2d}$ is 1 to 100, the left end of the group is bonded to the core (X), and the right end of the group is bonded to the terminal group (Y1B)); and

[Chem. 24]

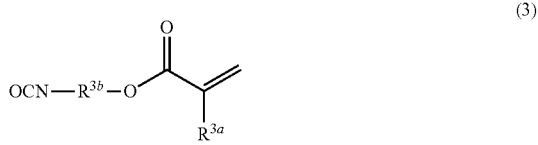

(3)

(in the general formula (3), $R^{3a}$ represents a hydrogen atom or a methyl group, $R^{3b}$ represents a $C_{2-6}$ linear alkylene group or a $C_{2-6}$ linear oxyalkylene group, and the linear alkylene group or the linear oxyalkylene group is optionally substituted with a $C_{1-6}$ alkyl group or a (meth)acryloyloxymethylene group in place of a hydrogen atom).

[10B]

The dental hydroxyl group-containing monomer according to [9B], wherein the terminal group (Y1B) is a hydrogen atom.

[11B]

The dental hydroxyl group-containing monomer according to [9B] or [10B], wherein in the linking group (Z) $n^{2a}$, $n^{2b}$, $n^{2c}$ and $n^{2d}$ are each 0 to 20, and the sum of $n^{2a}$, $n^{2b}$, $n^{2c}$ and $n^{2d}$ is 1 to 20.

[12B]

The dental hydroxyl group-containing monomer according to any of [9B] to [11B], wherein the linking group (Z) is a divalent group represented by the general formula (4) below:

[Chem. 25]

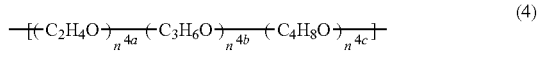

(4)

(in the general formula (4), $n^{4a}$, $n^{4b}$ and $n^{4c}$ represent the unit numbers of respective repeating units, and are each 0 to 20, the sum of $n^{4a}$, $n^{4b}$ and $n^{4c}$ is 1 to 20, the left end of the group is bonded to the core (X), and the right end of the group is bonded to the terminal group (Y1B)).

[13B]

The dental hydroxyl group-containing monomer according to any of [9B] to [12B], wherein the linking group (Z) is a divalent group represented by the general formula (5) below:

[Chem. 26]

$$-\!\!\!\!+\!(C_2H_4O)_{n^{5a}}\!\!+\!(C_3H_6O)_{n^{5b}}\!\!+\!\!-\qquad(5)$$

(in the general formula (5), $n^{5a}$ and $n^{5b}$ represent the unit numbers of respective repeating units, and are each 0 to 20, the sum of $n^{5a}$ and $n^{5b}$ is 1 to 20, the left end of the group is bonded to the core (X), and the right end of the group is bonded to the terminal group (Y1B)).

[14B]

The dental hydroxyl group-containing monomer according to any of [9B] to [13B], wherein the core (X) is an organic group having a valence of 3 to 12.

[15B]

The dental hydroxyl group-containing monomer according to any of [9B] to [14B], wherein the compound (1B) is at least one selected from the group consisting of compounds represented by the general formulas (6'a) to (6'k) below:

[Chem. 27]

(6'a) HO—CH₂—CH(OH)—CH₂—OH (6'b) HO—CH₂—C(CH₂OH)(CH₂CH₃)—CH₂—OH (6'c) HO—CH₂—C(CH₂OH)(CH₂OH)—CH₂—OH (6'd) HO—C(H)(OH)—C(H)(OH)—C(OH)(H)—C(H)(OH)—C(H)(OH)—C(H)(OH)—OH (6'e) HO—CH₂—C(CH₂OH)(CH₂OH)—CH₂—O—CH₂—C(CH₂OH)(CH₂OH)—CH₂—OH (6'f) HO—CH₂—C(H₂)(CH₂OH)(CH₂OH)—CH₂—O—CH₂—C(CH₂OH)(CH₂OH)—CH₂—O—CH₂—C(CH₂OH)(CH₂OH)—CH₂—OH (6'g) HO—(CH₂—CH(OH)—CH₂—O)$_{n^{6'g}}$—CH₂—CH(OH)—CH₂—OH (in the general formula (6g), $n^{6'g}$ is an integer of 1 to 40)

(6'h) HO—CH₂CH₂—N(CH₂CH₂OH)—CH₂CH₂—OH (6'i) $X\!-\!\!\left[\!(C_2H_4O)_{n^{6'i\text{-}b}}\right]_{n^{6'i\text{-}a}}\!\!\!-H$ (6'j) $X\!-\!\!\left[\!(C_3H_6O)_{n^{6'j\text{-}b}}\right]_{n^{6'j\text{-}a}}\!\!\!-H$ (6'k) $X\!-\!\!\left[\!(C_2H_4O)_{n^{6'k\text{-}b}}\!(C_3H_6O)_{n^{6'k\text{-}c}}\right]_{n^{6'k\text{-}a}}\!\!\!-H$ ($n^{6'i\text{-}a}$, $n^{6'j\text{-}a}$ and $n^{6'k\text{-}a}$ in the general formulas (6'i), (6'j) and (6'k) each represent the number of arms of a polyol bonded to the core X, and are each an integer of not less than 3; and $n^{6'i\text{-}b}$ and $n^{6'j\text{-}b}$ in the general formulas (6'i) and (6'j) represent the numbers of oxyethylene units and oxypropylene units, respectively, and are each in the range of 1 to 100, the numbers of units for respective arms may be the same as or different from each other, $n^{6'k\text{-}b}$ and $n^{6'k\text{-}c}$ in the general formula (6'k) represent the numbers of oxyethylene units and oxypropylene units, respectively, the sum thereof is in the range of 1 to 100, and the sums of the numbers of units for respective arms may be the same as or different from each other).

[16B]

The dental hydroxyl group-containing monomer according to any of [9B] to [15B], wherein the (meth)acryloyl group-containing isocyanate compound represented by the general formula (3) is at least one selected from the group consisting of compounds represented by the general formulas (3a) to (3f) below:

[Chem. 28]

(3a) OCN—CH₂CH₂—O—C(=O)—CH=CH₂

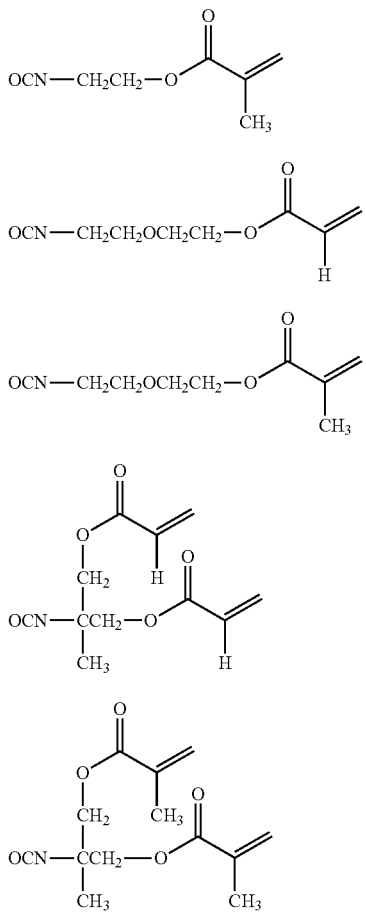

A dental monomer composition comprising the dental hydroxyl group-containing monomer according to any of [1B] to [16B].

[18B]

The dental monomer composition according to [17B], wherein the dental monomer composition is negative in a reverse mutation test.

[19B]

A dental material comprising the dental hydroxyl group-containing monomer according to any of [1B] to [16B].

[20B]

The dental material according to [19B], wherein the dental material is negative in a reverse mutation test.

[21B]

A kit comprising the dental material according to [19B] or [20B].

Advantageous Effects of Invention

The monomers obtained in the present invention are useful as dental materials.

A cured product having high strength is obtained by curing a composition containing a dental polyfunctional monomer according to the first aspect of the present invention. Further, the dental material containing the dental polyfunctional monomer has a low residual ratio of unreacted polymerizable terminals after curing.

A dental hydroxyl group-containing monomer according to the second aspect of the present invention has the function of enhancing adhesive strength with the tooth in dental treatment.

DESCRIPTION OF EMBODIMENTS

Hereinafter, the present invention will be described in detail. Herein, the "(meth)acryl" means acryl or mathacryl, and for example, the "(meth)acrylic acid" means methacrylic acid or acrylic acid. Similarly, the "(meth)acryloyl" means "acryloyl" or "methacryloyl", and the "(meth)acrylate" means "acrylate" or "methacrylate".

[Dental Polyfunctional Monomer]

A dental polyfunctional monomer according to the first aspect of the invention is a compound represented by the general formula (8A) below, in which the core (X) below and the terminal group (Y2A) below are bonded to each other directly or via the linking group (Z) below.

[Chem. 29]

$$X(Y2A)n^{8aA}(Z-Y2A)n^{8bA} \qquad (8A)$$

In the general formula (8A), $n^{8aA}$ represents the number of terminal groups (Y2A) directly bonded to the core (X), $n^{8bA}$ represents the number of terminal groups (Y2A) bonded to the core (X) via the linking group (Z), and the sum of $n^{8aA}$ and $n^{8bA}$ is equal to the valence of the core (X). The combination of $n^{8aA}$ and $n^{8bA}$ is not limited as long as each of $n^{8aA}$ and $n^{8bA}$ is an integer of not less than 0 and the sum thereof is not less than 3. As an example of the combination, $n^{8aA}$ is 0 and $n^{8bA}$ is an integer of not less than 3, and in this case, all the terminal groups (Y2A) are bonded to the core X via the linking group (Z). As another example of the combination, $n^{8bA}$ is 0 and $n^{8aA}$ is an integer of not less than 3, and in this case, all the terminal groups (Y2A) are directly bonded to the core X.

[Core (X)]

The core (X) is a polyvalent organic group having a valence of not less than 3 containing an oxygen atom or a nitrogen atom in which an atom bonded to the terminal group (Y2A) or the linking group (Z) is the oxygen atom or the nitrogen atom. The oxygen atom or nitrogen atom bonded to the terminal group (Y2A) or the linking group (Z) is bonded to a methylene group or a divalent aromatic carbon group in addition to the terminal group (Y2A) or the linking group (Z). Any hydrogen atom present in the methylene group or the divalent aromatic carbon group may be substituted by a $C_{1-12}$ monovalent hydrocarbon group. The number of carbon atoms in the core (X) is usually in the range of 1 to 200, preferably 1 to 100, more preferably 1 to 30, still more preferably 2 to 20.

The valence of the core (X) is not less than 3 as described above, and preferably 3 to 12, more preferably 3 to 8. The atom bonded to the terminal group (Y2A) or the linking group (Z) is selected from an oxygen atom and a nitrogen atom as described above, and is preferably an oxygen atom. Examples of the core (X) include groups represented by the general formulas (6a) to (6j) below.

[Chem. 30]

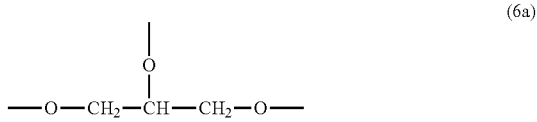

(6a)

(6b) 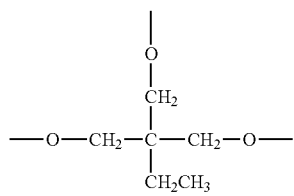

(6c) 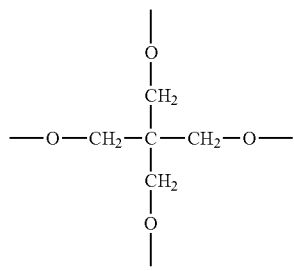

(6d) 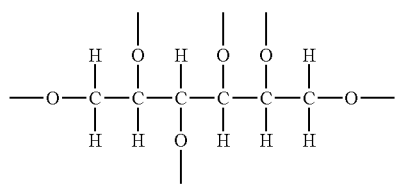

(6e) 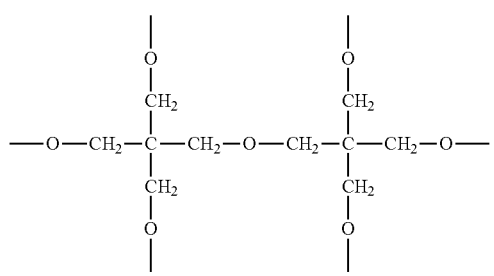

(6f) 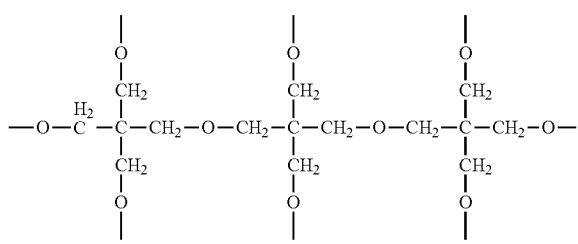

(6g) 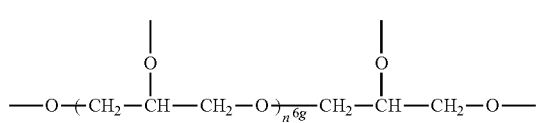

(6h) 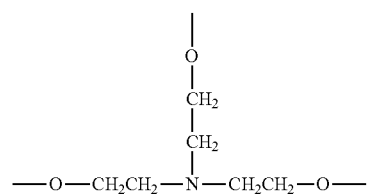

(6i) 

(6j) 

$n^{6g}$ in the general formula (6g) is an integer of 1 to 40, preferably 1 to 20, more preferably 1 to 10, still more preferably 1 to 5.

[Terminal Group (Y2A)]

The terminal group (Y2A) is a (meth)acryloyl group-containing group (Y3) represented by the general formula (9) below, a (meth)acryloyl group or a $C_{1-20}$ hydrocarbon group, and a plurality of terminal groups (Y2A) may be the same as or different from each other, with the proviso that among all the terminal groups (Y2A) in the compound represented by the general formula (8A), three or more terminal groups are (meth)acryloyl group-containing groups (Y3) or (meth)acryloyl groups, and one or more terminal groups are (meth)acryloyl group-containing groups (Y3).

[Chem. 31]

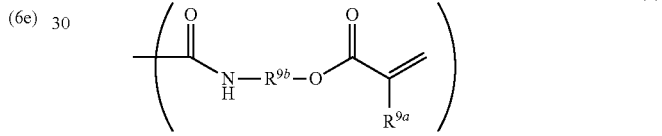

(9)

In the general formula (9), $R^{9a}$ represents a hydrogen atom or a methyl group, $R^{9b}$ represents a $C_{2-6}$ linear alkylene group or a $C_{2-6}$ linear oxyalkylene group, and the linear alkylene group or the linear oxyalkylene group is optionally substituted with a $C_{1-6}$ alkyl group or a (meth)acryloyloxymethylene group in place of a hydrogen atom. Examples of the (meth)acryloyl group-containing group (Y3) represented by the general formula (9) include groups represented by the general formulas (9a) to (9f) below.

[Chem. 32]

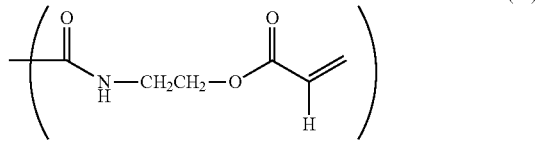

(9a)

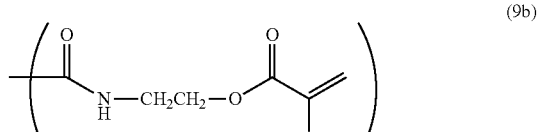

(9b)

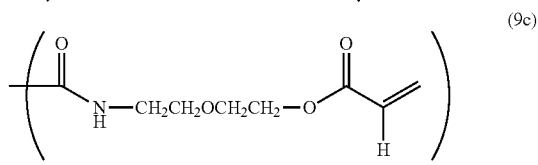

(9c)

-continued (9d)
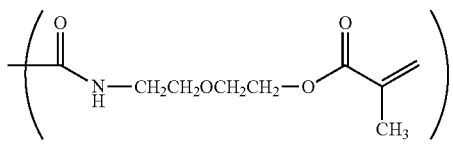

(9e)
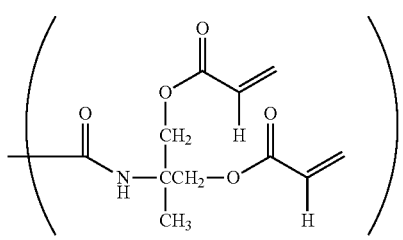

(9f)
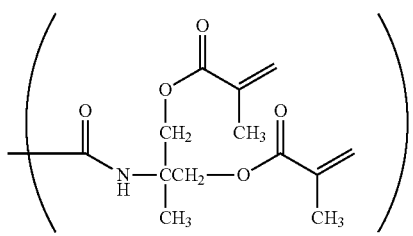

The terminal group (Y2A) is a (meth)acryloyl group-containing group (Y3) represented by the general formula (9), a (meth)acryloyl group or a $C_{1-20}$ hydrocarbon group as described above, and preferably a (meth)acryloyl group-containing group (Y3) or a (meth)acryloyl group, more preferably a (meth)acryloyl group-containing group (Y3).

[Linking Group (Z)]

The linking group (Z) is a divalent group represented by the general formula (2) below, and when the compound represented by the general formula (8A) contains a plurality of linking groups (Z), the linking groups (Z) may be the same as or different from each other.

[Chem. 33]

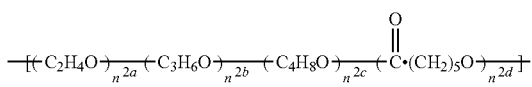
(2)

In the general formula (2), $n^{2a}$, $n^{2b}$, $n^{2c}$ and $n^{2d}$ represent the unit numbers of respective repeating units, and are each 0 to 100, preferably 0 to 20. The sum of $n^{2a}$, $n^{2b}$, $n^{2c}$ and $n^{2d}$ is 1 to 100, preferably 1 to 20. The left end of the group is bonded to the core (X), and the right end of the group is bonded to the terminal group (Y2A).

The repeating unit represented by —$C_2H_4O$— in the general formula (2) is an oxyethylene unit. Examples of the oxyethylene unit include —$CH_2CH_2O$— and —$CH(CH_3)O$—. Of these oxyethylene units, —$CH_2CH_2O$— is preferable. These oxyethylene units may be present singly, or two or more thereof may be present in combination.

The repeating unit represented by —$C_3H_6O$— in the general formula (2) is an oxypropylene unit. Examples of the oxypropylene unit include groups such as —$CH_2CH_2CH_2O$—, —$CH(CH_3)CH_2O$— and —$CH_2CH(CH_3)O$—. Of these oxypropylene units, —$CH(CH_3)CH_2O$— and —$CH_2CH(CH_3)O$— are preferable. These oxypropylene units may be present singly, or two or more thereof may be present in combination.

The repeating unit represented by —$C_4H_8O$— in the general formula (2) is an oxybutylene unit. Examples of the oxybutylene unit include groups such as —$CH_2CH_2CH_2CH_2O$—, —$CH(CH_3)CH_2CH_2O$—, —$CH_2CH(CH_3)CH_2O$—, —$CH_2CH_2CH(CH_3)O$—, —$CH(CH_2CH_3)CH_2O$—, —$CH_2CH(CH_2CH_3)O$—, —$CH(CH_3)CH(CH_3)O$—, —$C(CH_3)_2CH_2O$— and —$CH_2C(CH_3)_2O$—. Of these oxybutylene units, —$CH_2CH_2CH_2CH_2O$— is preferable. These oxybutylene units may be present singly, or two or more thereof may be present in combination.

The repeating unit represented by —$CO(CH_2)_5O$— in the general formula (2) is one unit of a polycaprolactone chain.

The repeating unit may be composed of one type of repeating unit, or two or more types of repeating units. When the repeating unit includes two or more types of repeating units, the form in which these repeating units are present is not particularly limited, and for example, the repeating units may be randomly present, or a certain number of certain repeating units may be grouped, that is, repeating units may be present in the form of blocks. Further, the sequence of these repeating units is not limited.

The linking group (Z) is preferably a divalent group represented by the general formula (4) below. When the compound represented by the general formula (8A) contains a plurality of linking groups (Z), the linking groups (Z) may be the same as or different from each other.

[Chem. 34]

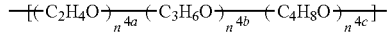
(4)

In the general formula (4), $n^{4a}$, $n^{4b}$ and $n^{4c}$ represent the unit numbers of respective repeating units, and are each 0 to 100, preferably 0 to 20. The sum of $n^{4a}$, $n^{4b}$ and $n^{4c}$ is 1 to 100, preferably 1 to 20. The left end of the group is bonded to the core (X), and the right end of the group is bonded to the terminal group (Y2A). The descriptions of the repeating units in the general formula (4) are the same as the descriptions of the repeating units in the general formula (2).

The linking group (Z) is more preferably a divalent group represented by the general formula (5) below. When the compound represented by the general formula (8A) contains a plurality of linking groups (Z), the linking groups (Z) may be the same as or different from each other.

[Chem. 35]

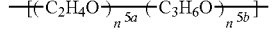
(5)

In the general formula (5), $n^{5a}$ and $n^{5b}$ represent the unit numbers of respective repeating units, and are each 0 to 100, preferably 0 to 20. The sum of $n^{5a}$ and $n^{5b}$ is 1 to 100, preferably 1 to 20. The left end of the group is bonded to the core (X), and the right end of the group is bonded to the terminal group (Y2A). The descriptions of the repeating units in the general formula (5) are the same as the descriptions of the repeating units in the general formula (2).

More specific examples of the linking group (Z) may include linking groups having repeating units composed of only oxyethylene units (linking groups in which $n^{5b}$ is 0, and $n^{5a}$ is 1 to 100, preferably 1 to 20 in the general formula (5)), linking groups having repeating units composed of only oxypropylene units (linking groups in which $n^{5a}$ is 0, and $n^{5b}$ is 1 to 100, preferably 1 to 20 in the general formula (5)), and linking groups having a block structure of polymer block composed of oxypropylene units/polymer block composed of oxyethylene units/polymer block composed of oxypropylene units (linking groups having a structure in which blocks are linked in the structure (5') below in the general formula (5)).

[Chem. 36]

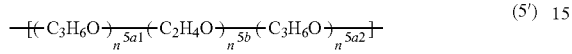
(5')

In the general formula (5'), $n^{5a1}$, $n^{5a2}$ and $n^{5b}$ represent the unit numbers of respective repeating units, and are each 1 to 100, preferably 1 to 20. The sum of $n^{5a1}$, $n^{5a2}$ and $n^{5b}$ is 1 to 100, preferably 1 to 20. The left end of the group is bonded to the core (X), the right end of the group is bonded to the terminal group (Y2A), and the oxypropylene polymer blocks and the oxyethylene polymer block in the bracket are bonded in the order presented. The descriptions of the repeating units in the general formula (5') are the same as the descriptions of the repeating units in the general formula (2).

[Method for Producing Dental Polyfunctional Monomer]

The dental polyfunctional monomer of the invention is obtained by, for example, reacting all active protons in a compound represented by the general formula (1A) below, in which the core (X) below and the terminal group (Y1A) below are bonded to each other directly or via the linking group (Z) below, with isocyanate groups in a (meth)acryloyl group-containing isocyanate compound represented by the general formula (3) below to form corresponding carbamate groups or urea groups. The active proton mentioned here is a hydrogen atom which is bonded to alcoholic oxygen and amine nitrogen and which has reactivity with isocyanate at a practical rate.

The condition for production of the dental polyfunctional monomer of the invention is, for example, reaction of a raw material containing a compound represented by the general formula (1A) below, in which the core (X) below and the terminal group (Y1A) below are bonded to each other directly or via the linking group (Z) below, with a raw material containing a (meth)acryloyl group-containing isocyanate compound represented by the general formula (3) below, at a ratio of (the number of moles of isocyanate groups present in the compound represented by the general formula (3) below)/(the number of moles of active protons bonded to oxygen atoms and nitrogen atoms present in the compound represented by the general formula (1A) below) (hereinafter, written as a reaction ratio during production)=1.

As another example thereof, there is reaction under a condition of the reaction ratio during production >1. Here, in terms of a stoichiometric ratio, the (meth)acryloyl group-containing isocyanate compound represented by the general formula (3) below remains, but all active protons in the compound represented by the general formula (1A) below can be reacted with isocyanate groups to give a mixture containing the dental polyfunctional monomer of the invention. The reaction ratio during production is preferably close to 1, and is, for example, not more than 2, preferably not more than 1.5, more preferably not more than 1.2. Such a mixture can also be blended with the dental material of the invention directly or even by way of known reaction or treatment.

As still another example thereof, there is reaction under a condition of the reaction ratio during production <1. Here, in terms of a stoichiometric ratio, some of active protons in the compound represented by the general formula (1A) below remain in the reaction product, but when the reaction ratio during production is higher than a certain level, a mixture containing the dental polyfunctional monomer of the invention can be obtained. For enhancing the ratio of the dental polyfunctional monomer of the invention in the mixture, the reaction ratio during production is preferably close to 1, and is, for example, equal to or greater than ((the average number of active protons per molecule−1)/(the average number of active protons per molecule)). Such a mixture can also be blended with the dental material of the invention directly or even by way of known reaction or treatment.

The number of moles of active protons in a raw material containing the compound represented by the general formula (1A) below can be determined by calculation on the basis of a known analysis method, for example measurement of a hydroxyl group value, specifically JIS K 0070-1992, JIS K 1557-1-2007, ISO 14900-2001, a method conforming thereto, or the like. Further, the number of moles of isocyanate groups present in the compound represented by the general formula (3) below can be determined by calculation on the basis of a known analysis method, for example measurement of a NCO value, specifically JIS K 7301-1995, JIS K 1603-2007, JIS K 1556-2006, ISO 14896-2006, a method conforming thereto, or the like.

[Chem. 37]

(1A)

In the general formula (1A), $n^{1aA}$ represents the number of terminal groups (Y1A) directly bonded to the core (X), $n^{1bA}$ represents the number of terminal groups (Y1A) bonded to the core (X) via the linking group (Z), and the sum of $n^{1aA}$ and $n^{1bA}$ is equal to the valence of the core (X). The combination of $n^{1aA}$ and $n^{1bA}$ is not limited as long as each of $n^{1aA}$ and $n^{1bA}$ is an integer of not less than 0 and the sum thereof is not less than 3. As an example of the combination, $n^{1aA}$ is 0 and $n^{1bA}$ is an integer of not less than 3, and in this case, all the terminal groups (Y1A) are bonded to the core X via the linking group (Z). As another example of the combination, $n^{1bA}$ is 0 and $n^{1aA}$ is an integer of not less than 3, and in this case, all the terminal groups (Y2A) are directly bonded to the core X. The core (X) and the linking group (Z) are as described for the general formula (8A)

[Terminal group Y1A]

The terminal group (Y1A) is a (meth)acryloyl group, a $C_{1-20}$ monovalent hydrocarbon group or a hydrogen atom, a plurality of terminal groups (Y1A) may be the same as or different from each other, with the proviso that among the terminal groups (Y1A) present in the compound represented by the general formula (1A), three or more terminal groups (Y1A) are hydrogen atoms or (meth)acryloyl groups, and one or more terminal groups (Y1A) are hydrogen atoms. The terminal group (Y1A) is preferably a (meth)acryloyl group or a hydrogen atom, and is more preferably composed of only a hydrogen atom.

Specific Examples of Compounds of General Formula (1A)

Examples of the compounds of the general formula (1A) include polyols represented by the general formulas (6'a) to (6'h) below.

[Chem. 38]

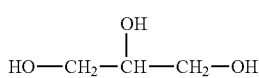
(6'a)

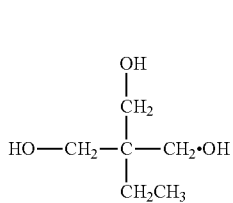
(6'b)

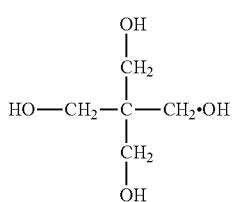
(6'c)

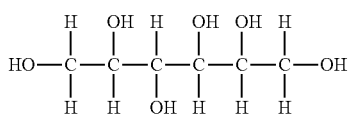
(6'd)

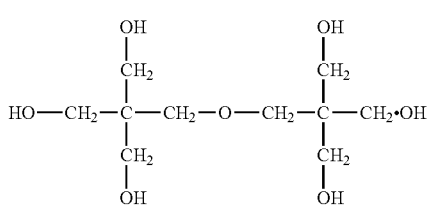
(6'e)

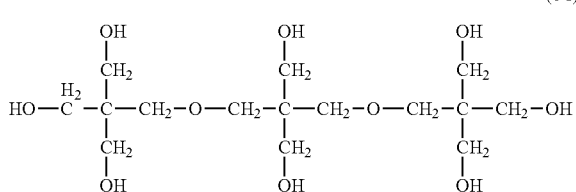
(6'f)

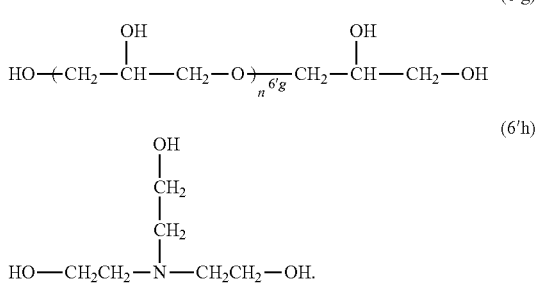
(6'g)

(6'h)

HO—CH$_2$CH$_2$—N(—CH$_2$CH$_2$—OH)—CH$_2$ CH$_2$ OH $n^{6'g}$ in the general formula (6'g) is an integer of 1 to 40, preferably 1 to 20, more preferably 1 to 10, still more preferably 1 to 5.

Among the compounds represented by the general formula (1A), other compounds are polyols represented by the general formulas (6'i) to (6'k) below.

[Chem. 39]

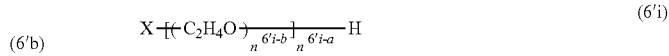
(6'i)

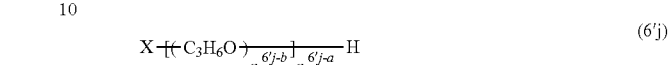
(6'j)

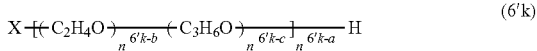
(6'k)

$n^{6'i\text{-}a}$, $n^{6'j\text{-}a}$ and $n^{6'k\text{-}a}$ in the general formulas (6'i), (6'j) and (6'k) each represent the number of arms of a polyol bonded to the core (X), and are each an integer of not less than 3, preferably 3 to 12, more preferably 3 to 8, still more preferably 3 to 6 in the invention. $n^{6'i\text{-}b}$ and $n^{6'j\text{-}b}$ in the general formulas (6'i) and (6'j) represent the numbers of oxyethylene units and oxypropylene units, respectively, and are each in the range of 1 to 100, preferably 1 to 20, and the numbers of repeating units for respective arms may be the same as or different from each other. $n^{6'k\text{-}b}$ and $n^{6'k\text{-}c}$ in the general formula (6'k) represent the numbers of oxyethylene units and oxypropylene units, respectively, the sum thereof is in the range of 1 to 100, preferably 1 to 20, and the sums of the numbers of repeating units for respective arms may be the same as or different from each other. X in each of the general formulas (6'i), (6'j) and (6'k) is the core (X), and examples thereof include at least one group selected from the group consisting of groups represented by the general formulas (6a) to (6h).

Some of the polyols having repeating units such as oxyethylene units and oxypropylene units in the molecule have been already widely used in the industrial world as materials for polyurethane and the like. While the method for producing the polyols is not particularly limited, these polyols are obtained by adding ethylene oxide, propylene oxide or the like to polyols represented by the general formulas (6'a) to (6'h) using a known method.

[(Meth)Acryloyl Group-Containing Isocyanate Compound]

[Chem. 40]

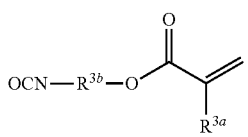
(3)

In the general formula (3), $R^{3a}$ represents a hydrogen atom or a methyl group, $R^{3b}$ represents a $C_{2\text{-}6}$ linear alkylene group or a $C_{2\text{-}6}$ linear oxyalkylene group, and the linear alkylene group or the linear oxyalkylene group is optionally substituted with a $C_{1\text{-}6}$ alkyl group or a (meth)acryloyloxymethylene group in place of a hydrogen atom.

Specific examples of the (meth)acryloyl group-containing isocyanate compounds represented by the general formula (3) may include at least one selected from the group consisting of compounds represented by the general formulas (3a) to (3f) below.

[Chem. 41]

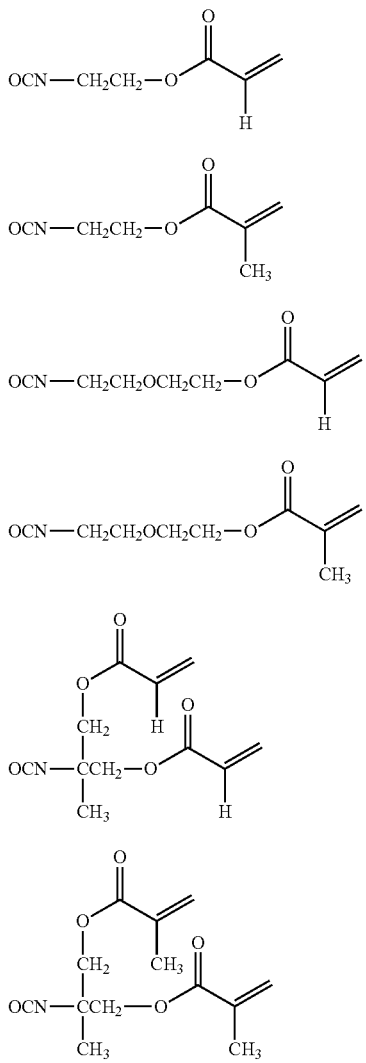

These (meth)acryloyl group-containing isocyanate compounds may be used singly, or two or more thereof may be used in combination.

[Reaction Conditions]

As described above, the dental polyfunctional monomer of the invention is obtained by reacting a compound represented by the general formula (1A) with a (meth)acryloyl group-containing isocyanate compound represented by the general formula (3). The reaction can be carried out by a known method or a substantially known method.

The dental polyfunctional monomer of the invention can be obtained by, for example, mixing a compound represented by the general formula (1A) with a (meth)acryloyl group-containing isocyanate compound represented by the general formula (3). During this process, the hydroxyl groups or the amino groups in the compound represented by the general formula (1A) react with the isocyanate groups in the (meth)acryloyl group-containing isocyanate compound represented by the general formula (3) to form carbamoyl groups or urea groups. This reaction is sometimes called the urethane-forming reaction.

The reaction may be carried out in the presence or absence of a catalyst. To enhance the reaction rate, a catalyst is preferably added. Known catalysts capable of accelerating the urethane-forming reaction may be used as the catalysts.

Examples of the urethane-forming catalysts include organotin compounds such as dibutyltin dilaurate, dibutyltin dioctoate and tin octanoate; organic compounds of metals other than tin such as copper naphthenate, cobalt naphthenate, zinc naphthenate, acetylacetonatozirconium, acetylacetonatoiron and acetylacetonatogermanium; amine compounds and salts thereof such as triethylamine, 1,4-diazabicyclo[2.2.2]octane, 2,6,7-trimethyl-1-diazabicyclo[2.2.2]octane, 1,8-diazabicyclo[5.4.0]undecene, N,N-dimethylcyclohexylamine, pyridine, N-methylmorpholine, N,N,N',N'-tetramethylethylenediamine, N,N,N',N'-tetramethyl-1,3-butanediamine, N,N,N',N'-pentamethyldiethylenetriamine, N,N,N',N'-tetra(3-dimethylaminopropyl)-methanediamine, N,N'-dimethylpiperazine and 1,2-dimethylimidazole; and trialkylphosphine compounds such as tri-n-butylphosphine, tri-n-hexylphosphine, tricyclohexylphosphine and tri-n-octylphosphine.

Of these, dibutyltin dilaurate and tin octanoate are advantageous in that the reaction is facilitated with a small amount of the catalyst and the catalyst has high selectivity for diisocyanate compounds.

When the urethane-forming catalyst is used, the amount thereof is preferably 0.001 to 0.5 parts by weight, more preferably 0.002 to 0.3 parts by weight, still more preferably 0.01 to 0.3 parts by weight, further preferably 0.01 to 0.2 parts by weight, still further preferably 0.05 to 0.2 parts by weight per 100 parts by weight in total of the compound represented by the general formula (1A) and the (meth)acryloyl group-containing isocyanate compound represented by the general formula (3). If the amount is below the lower limit, the catalytic effect is decreased to give rise to a risk that a significantly long reaction time is incurred. If the amount is above the upper limit, the catalytic effect is so increased that the reaction generates a large amount of heat possibly to make it difficult to control the temperature. The catalyst may be added in the whole amount at the initiation of the reaction, or may be added successively or in portions to the reaction system as required. Such successive or portionwise addition of the catalyst prevents the generation of an excessively large amount of reaction heat at the initial stage of the reaction and thus facilitates the control of the reaction temperature.

The reaction temperature is not particularly limited, but is preferably 0 to 120° C., more preferably 20 to 100° C., and still more preferably 40 to 80° C. At a reaction temperature below the lower limit, the reaction rate is markedly decreased and the reaction requires a very long time to complete or does not complete at times. On the other hand, the reaction at a temperature above the upper limit may involve side reactions generating impurities. Such impurities may cause the coloration of the dental polyfunctional monomer produced.

To ensure stable production at the aforementioned preferred range of temperatures, it is preferable that the reaction temperature be controlled. The urethane-forming reaction is usually exothermic. In the case where the reaction generates a large amount of heat and the temperature of the reaction product may be elevated above the preferred range of the reaction temperature, cooling is sometimes performed. When the reaction has substantially completed and the temperature of the reaction product may be decreased below the preferred range of the reaction temperature, heating is sometimes performed.

The dental polyfunctional monomer of the invention has polymerization activity. Thus, undesired polymerization reaction may take place when the system is subjected to a high temperature during the production of the acrylate. To prevent such undesired polymerization reaction, a known polymerization inhibitor may be added before the initiation of the reaction or during the reaction. The polymerization inhibitor is not particularly limited as long as the inhibitor can suppress undesired polymerization of (meth)acryloyl groups in production of the dental polyfunctional monomer of the invention. Examples thereof include dibutylhydroxytoluene (BHT), hydroquinone (HQ), hydroquinone monomethyl ether (MEHQ) and phenothiazine (PTZ). Of these polymerization inhibitors, BHT is particularly preferable because the consumption of the inhibitor by the reaction with the isocyanate groups is small as compared to other phenolic polymerization inhibitors and also because the coloration encountered with amine polymerization inhibitors is small. The amount of the polymerization inhibitor added is not particularly limited, but is preferably 0.001 to 0.5 parts by weight, more preferably 0.002 to 0.3 parts by weight, still more preferably 0.005 to 0.3 parts by weight, further preferably 0.005 to 0.1 parts by weight, still further preferably 0.01 to 0.1 parts by weight per 100 parts by weight in total of the compound represented by the general formula (1A) and the (meth)acryloyl group-containing isocyanate compound represented by the general formula (3). If the amount is below the lower limit, the polymerization inhibitor may fail to perform as expected. If the amount is above the upper limit, a dental material containing such a dental polyfunctional monomer may exhibit a markedly low curing rate and may have a limited practical applicability.

The urethane-forming reaction may involve a solvent. The solvent is not particularly limited as long as the solvent does not have practical reactivity with the compound represented by the general formula (1A) and the (meth)acryloyl group-containing isocyanate compound represented by the general formula (3), does not inhibit the reaction, and can dissolve the raw materials and the product. The reaction may be performed in the absence of solvents. The (meth)acryloyl group-containing isocyanate compound represented by the general formula (3) is usually a low viscous liquid and is miscible with the compound represented by the general formula (1A) to allow the reaction to take place without solvents.

The compound represented by the general formula (1A) and the (meth)acryloyl group-containing isocyanate compound represented by the general formula (3) may be mixed with each other by any methods without limitation. For example, a controlled amount of the (meth)acryloyl group-containing isocyanate compound represented by the general formula (3) may be admixed with the compound represented by the general formula (1A) placed in a reaction vessel; a controlled amount of the compound represented by the general formula (1A) may be admixed with the (meth) acryloyl group-containing isocyanate compound represented by the general formula (3) placed in a reaction vessel; or controlled amounts of the compound represented by the general formula (1A) and the (meth)acryloyl group-containing isocyanate compound represented by the general formula (3) may be added to a reaction vessel at the same time and mixed with each other. By these mixing methods, the amount of heat generated by the urethane-forming reaction can be controlled in an appropriate range and thus the temperature control during the reaction is facilitated. Alternatively, the urethane-forming reaction may be performed in such a manner that the whole amounts of the compound represented by the general formula (1A) and the (meth) acryloyl group-containing isocyanate compound represented by the general formula (3) are added to a reaction vessel and thereafter the temperature is increased. During the reaction, the reaction temperature may be sharply increased due to the generation of reaction heat and the temperature control by cooling may be appropriately required at times.

Oxygen is effective as a polymerization inhibitor for compounds containing (meth)acryloyl groups. Thus, oxygen is sometimes introduced into the reactor to prevent undesired polymerization of (meth)acryloyl groups during the reaction. For example, oxygen may be introduced into the reactor in such a form as dried air or oxygen gas. Preferably, oxygen is introduced into the reactor in the form of dried air. For example, the dried air may be obtained by removing water using a known drying method such as the use of a condensing air dryer. In another aspect, a mixed gas including oxygen and an inert gas such as nitrogen may be introduced into the reactor. The use of such a mixed gas including oxygen and an inert gas such as nitrogen is preferable similarly to the use of the dried air. The mixed gas including oxygen and an inert gas such as nitrogen may be obtained by mixing oxygen gas or the dried air containing oxygen with a prescribed amount of nitrogen. Here, nitrogen is preferably one that has been dehydrated by a known drying method. The method for the introduction is not particularly limited. For example, the gas may be introduced in the form of bubbles from the bottom of the reaction vessel continuously or intermittently. Alternatively, the gas may be introduced continuously or intermittently to the space at the top of the reaction vessel.

If water is present as an impurity in the system during the urethane-forming reaction, the (meth)acryloyl group-containing isocyanate compound represented by the general formula (3) and the water may react with each other, resulting in formation of unintended impurities. Thus, it is preferable that as little water as possible be present in the reaction system during the urethane-forming reaction.

Therefore, the amount of water present in the compound represented by the general formula (1A) is preferably as small as possible. Specifically, the amount of water is preferably not more than 0.5 wt %, more preferably not more than 0.3 wt %, still more preferably not more than 0.1 wt % based on the amount of the compound represented by the general formula (1A). In the case where the compound represented by the general formula (1A) contains water in an amount exceeding the upper limit, it is preferable that the compound be used as a raw material for the dental polyfunctional monomer of the invention after water is removed therefrom by a known method. The reaction vessel in which the urethane-forming reaction will be performed is preferably dried by a known method to remove water therefrom.

[Dental Monomer Composition Containing Dental Polyfunctional Monomer]

The dental polyfunctional monomer according to the first aspect of the invention can be blended with other components, for example components other than the polyfunctional monomers and suitable for dental materials, to form a dental monomer composition. The dental monomer composition may contain, for example, a polymerizable monomer other than the dental polyfunctional monomers according to the first aspect of the invention and capable of being blended with the later-described dental materials (for example a (meth)acrylate group-containing monomer other than the polyfunctional monomers of the invention).

In the dental monomer composition according to the first aspect of the invention, for example, the content of the dental polyfunctional monomer according to the first aspect of the invention may be not less than 1.0 mass % (e.g. not less than 10 mass %, not less than 50 mass %, not less than 80 mass % or not less than 90 mass %) and may be not more than 100 mass % (e.g. not more than 99 mass %, not more than 90 mass %, not more than 80 mass %, not more than 50 mass % or not more than 10 mass %) based on the total amount of the dental monomer composition.

(Reverse Mutation Test)

The dental monomer composition according to the first aspect of the invention is preferably negative in a reverse mutation test. The reverse mutation test (Ames test) means a test for examining the mutagenicity of a composition using microorganisms. The reverse mutation test in the present invention is conducted by the following method.

Specifically, the reverse mutation test is conducted under a fluorescent lamp with an ultraviolet absorbing film and/or a LED in accordance with the following procedure.

First, to a sterilized test tube are added 0.1 mL of a test composition solution having dimethyl sulfoxide (DMSO) as a medium, and 0.5 mL of a 0.1 M phosphate buffer solution (pH 7.4) in the case where metabolic activation is not performed, or 0.5 mL of the later-described S9mix in the case where metabolic activation is performed. Thereafter, 0.1 mL of the later-described bacterial suspension is added, and the resulting mixture is mixed. The resulting mixture is preincubated at about 100 rpm for 20 minutes, 2 mL of the later-described top agar is then added, and the resulting mixture is mixed, and overlaid on the later-described minimal glucose agar plate medium (five or more doses). After it is confirmed that the mixture has been overlaid and solidified, the minimal glucose agar plate medium is turned upside down, and culture is performed at 37° C. for 48 hours. Whether the result is negative or positive is determined on the cultured plate. When a negative control substance is subjected to the test, DMSO is used as the negative control substance, and 0.1 mL of the medium is added instead of the test composition solution in the above-described process.

After completion of the culture, the number of revertant colonies on each plate is measured.

Regarding the criterion for determining whether the result is negative or positive, it is determined that the test composition is negative when the average number of colonies with the test composition is equal to or less than two times the average number of colonies with only the negative control substance for all strains, at all doses and in both the cases where metabolic activation is not performed and metabolic activation is performed.

In the reverse mutation test, the doses of a test substance present in the test composition solution (specifically, the dental polyfunctional monomer present in the dental monomer composition) are adjusted so that a maximum dose of 5000 µg per plate is followed by five or more doses descending in a geometric progression with a common ratio of 2 to 4.

The strain to be used is *Salmonella typhimurium* TA 100 or TA 1535, or *Escherichia coli* WP2uvrA, which are a base pair substitution mutant strain, or *Salmonella typhimurium* TA 98 or TA 1537, which are a frameshift mutant strain.

The minimal glucose agar plate medium to be used is Tesmedia AN Medium (manufactured by Oriental Yeast Co., Ltd., for testing of mutagenicity).

The number of the minimal glucose agar plate media per dose is not less than 2 for the negative control substance, and not less than 2 for the test composition.

The case where metabolic activation is performed means that S9mix (a rat liver microsome fraction containing a coenzyme) is added together with a test substance, and the case where metabolic activation is not performed means that S9mix is not added. Specifically, the S9mix has the composition of S9: 0.1 mL (a supernatant portion of a liver homogenate centrifuged at 9000×g), $MgCl2$: 8 µmol, KCl: 33 µmol, glucose-6-phosphoric acid: 5 µmol, NADPH: 4 µmol, NAPH: 4 µmol and sodium phosphate buffer solution (pH 7.4): 100 µmol.

The top agar to be used is a mixture obtained by subjecting an amino acid solution (0.5 mmol/L L-histidine, 0.5 mmol/L D-biotin and 0.5 mmol/L L-tryptophane) to filtration sterilization, subjecting a soft agar solution (0.6% (w/v) agar (Bacto-Agar) and 0.5% (w/v) sodium chloride) to high-pressure steam sterilization at 121° C. for 20 minutes, and mixing the amino acid solution and the melted soft agar solution at a volume ratio of 1:10.

In preparation of each bacterial suspension, the bacterial concentration is adjusted to not less than $1 \times 10^9$ bacteria per mL for each bacterium. For culture of each bacterium, a nutrient broth culture is used. The nutrient broth culture is prepared by dissolving Nutrient Broth No. 2 (Oxoid, Nutrient Broth No. 2) in purified water to a concentration of 2.5 wt %, and subjecting the resulting solution to high-pressure steam sterilization at 121° C. for 20 minutes.

(Cytotoxicity Test by NRU Method)

The dental monomer composition according to the first aspect of the invention may allow the relative cell survival rate to fall within a certain range in a cytotoxicity test by an NRU method using the later-described Balb/3T3 cells. The cytotoxicity test is conducted by the following method.

Balb/3T3 cells (Balb/3T3 clone A31 cells (mouse skin-derived fibroblast cells)) are seeded at a density of 10000 cells per well in a 96-well plate, and precultured for 25 hours, the medium in each well is then removed, 0.1 mL of a test solution containing a test composition or a negative control solution is added to the cells, and the cells are cultured in a $CO_2$ incubator for 24 hours. Here, 12 wells are used for the negative control solution, and 6 wells are used for the test solution. After the culture, each well is observed under a microscope to confirm growth of the cells, the culture in each well is removed, and washing is performed with 0.15 mL of PBS. After the washing, 0.1 mL of an NR culture is added to each well, and the cells are cultured in a $CO_2$ incubator for 3 hours to perform staining. After the culture, the culture in each well is removed, and washing is performed with 0.15 mL of PBS. 0.15 ml of an NR-redissolving solution is added to each well, and shaken with a plate shaker for 10 minutes. Neutral red (NR) is dissolved in the NR-redissolving solution, the absorbance of the solution in each well is then measured at 540 nm, and the average value of the absorbances is determined. The absorbance of a solution in a well containing the test solution is calculated as a relative value against the absorbance of a solution in a well containing the negative control solution, with the latter absorbance set to 100, and the thus-obtained value is defined as a relative cell survival rate (%) of a test composition containing a test substance (a dental monomer composition containing a dental polyfunctional monomer).

For preparation of a test solution containing a test composition, a test composition is added to DMSO, and the resulting mixture is then diluted with DMSO to prepare a DMSO solution. Thereafter, 10 µL of the above-described DMSO solution is added per 2 mL of the later-described D05 culture, and the resulting mixture is stirred and mixed to prepare a test solution. The test solution is adjusted so that the test composition solution contains a test substance at a predetermined concentration (specifically, the dental monomer composition contains a dental polyfunctional monomer at a predetermined concentration).

The negative control solution is prepared by adding DMSO to the D05 culture to a concentration of 0.5 v/v %.

The D05 culture is D-MEM (Dulbecco's Modified Eagle's Medium 9, Cat No. 048-30275, containing 584 mg/L of glutamine and 5.958 g/L of HEPES) which contains 5 vol % of calf serum, 1 mmol/L sodium pyruvate and 1 vol % of a penicillin-streptomycin-amphotericin B suspension.

The D10 culture is D-MEM containing 10 vol % of calf serum, 1 vol % of a penicillin-streptomycin-amphotericin B suspension and 1 vol % of a 100 mmol/L sodium pyruvate solution.

The preculture of the Balb/3T3 cells is performed in the following manner: cells in the logarithmic growth phase are isolated using trypsin-EDTA, a cell suspension having a cell concentration of $1×10^5$ cells/mL is then prepared using a D05 culture, and 0.1 mL of the cell suspension is then dispensed and seeded in a 96-well plate ($1×10^4$ cells/well), and left standing in a $CO_2$ incubator for 25 hours.

The NR culture is a culture obtained by mixing an NR (neutral red) stock solution and a D10 culture at a ratio of 1:79, leaving the resulting mixture overnight at 37° C., and then removing the NR crystal by filtration with a filter.

The NR (neutral red) stock solution is a 0.4% (w/v) aqueous solution of neutral red (NR) (manufactured by Wako Pure Chemical Industries, Ltd.).

The NR-dissolving solution is a solution obtained by mixing acetic acid, ethanol and water at a ratio of 1:50:49. The NR-dissolving solution is prepared within an hour before use.

The concentration of the test substance of the test composition in the test solution may be, for example, 0.00164 mg/mL, 0.00410 mg/mL, 0.0102 mg/mL, 0.0256 mg/mL, 0.0640 mg/mL, 0.160 mg/mL, 0.400 mg/mL or 1.00 mg/mL.

When the concentration of the test substance of the test composition in the test solution is 0.00164 mg/mL, 0.00410 mg/mL, 0.0102 mg/mL, 0.0256 mg/mL, 0.0640 mg/mL, 0.160 mg/mL, 0.400 mg/mL or 1.00 mg/mL, the relative cell survival rate in the NRU method using the BALB/3T3 cells may be not less than 0.01% (e.g. not less than 0.05%, not less than 0.1%, not less than 0.5%, not less than 1.0%, not less than 5.0%, not less than 10%, not less than 20%, not less than 30%, not less than 40%, not less than 50%, not less than 60%, not less than 70%, not less than 80%, not less than 90%, not less than 95% or not less than 99%), and may be not more than 100% (e.g. not more than 99%, not more than 95%, not more than 90%, not more than 80%, not more than 70%, not more than 60%, not more than 50%, not more than 40%, not more than 30%, not more than 20%, not more than 10%, not more than 5.0%, not more than 1.0%, not more than 0.5%, not more than 0.1% or not more than 0.05%).

(Cell Test by WST Method)

The dental monomer composition according to the first aspect of the invention may allow the relative cell growth rate to fall within a certain range in a cell test by a WST method using the Balb/3T3 cells. The cell test is conducted by the following method.

Balb/3T3 cells (Balb/3T3 clone A31 cells (mouse skin-derived fibroblast cells)) are seeded at a density of 2000 cells per well in a 96-well plate, and precultured for 24 hours, the culture in each well is then removed, 0.1 mL of a test solution containing a test composition or a negative control solution is added to the cells, and the cells are cultured in a $CO_2$ incubator for 48 hours. Here, 6 wells are used for the negative control solution, and 3 wells are used for the test solution.

After the culture, the test solution or the negative control solution is discarded, washing is performed with PBS, 0.2 mL of a DMEM culture containing a 10% WST-8 reagent is added to each well, and color reaction is carried out in a $CO_2$ incubator for 2 hours. The absorbance of the solution in the well after the reaction is measured at 450 nm and 650 nm by a microplate reader. A value obtained by subtracting the 650 nm-absorbance from the 450 nm-absorbance of the solution in each well is defined as the absorbance for each well, and with a negative value set to 0 if any, the average value of the absorbances is determined. A value obtained by dividing the average absorbance of the solution in wells containing the test solution by the average absorbance of the solution in wells containing the negative control solution is defined as a relative cell growth rate (%) of a test composition containing a test substance (a dental monomer composition containing a dental polyfunctional monomer).

For preparation of a test solution containing a test composition, a test composition is added to DMSO, and the resulting mixture is then diluted with DMSO to prepare a DMSO solution. Thereafter, 5 µL of the solution diluted with DMSO solution is added per mL of a DMEM culture to prepare a test solution. The test solution is adjusted so that the test composition solution contains a test substance at a predetermined concentration (specifically, the dental monomer composition contains a dental polyfunctional monomer at a predetermined concentration).

The negative control solution is prepared by adding DMSO to the DMEM culture to a concentration of 0.5 v/v %.

The DMEM culture is Dulbecco's Modified Eagle's Medium (D-MEM) containing 10 vol % of calf serum and 1 vol % of a penicillin-streptomycin-amphotericin B suspension (×100).

The preculture of the Balb/3T3 cells is performed in the following manner: Balb/3T3 clone A31 cells in the logarithmic growth phase are isolated using 0.25% trypsin-1 mM EDTA, a cell suspension having a cell concentration of 20000 cells/mL is then prepared using a DMEM culture, and 0.1 mL of the cell suspension is then dispensed and seeded in a 96-well plate (2000 cells/well), and left standing in a $CO_2$ incubator for 24 hours.

The concentration of the test substance of the test composition in the test solution may be, for example, 0.00164 mg/mL, 0.00410 mg/mL, 0.0102 mg/mL, 0.0256 mg/mL, 0.0640 mg/mL, 0.160 mg/mL, 0.400 mg/mL or 1.00 mg/mL.

When the concentration of the test substance of the test composition in the test solution is 0.00164 mg/mL, 0.00410 mg/mL, 0.0102 mg/mL, 0.0256 mg/mL, 0.0640 mg/mL, 0.160 mg/mL, 0.400 mg/mL or 1.00 mg/mL, the relative cell growth blocking rate in the WST method using the BALB/3T3 cells may be not less than 0.001% (e.g. not less than 0.01%, not less than 0.05%, not less than 0.1%, not less than 0.5%, not less than 1.0%, not less than 5.0%, not less than 10%, not less than 20%, not less than 30%, not less than 40%, not less than 50%, not less than 60%, not less than 70%, not less than 80%, not less than 90%, not less than 95% or not less than 99%), and may be not more than 100% (e.g.

not more than 99%, not more than 95%, not more than 90%, not more than 80%, not more than 70%, not more than 60%, not more than 50%, not more than 40%, not more than 30%, not more than 20%, not more than 10%, not more than 5.0%, not more than 1.0%, not more than 0.5%, not more than 0.1%, not more than 0.05% or not more than 0.01%).

[Dental Material Containing Dental Polyfunctional Monomer]

The dental polyfunctional monomer according to the first aspect of the invention is suitable as a raw material for dental materials. By blending the dental polyfunctional monomer of the invention with components other than the dental polyfunctional monomers of the invention (for example polymerizable monomers other than the dental polyfunctional monomers ((meth)acrylate group-containing monomers other than the polyfunctional monomers of the invention, monomers containing epoxy groups, and the like)), a dental material containing the dental polyfunctional monomer of the invention can be produced.

[(Meth)Acrylate Group-Containing Monomers Other than Inventive Polyfunctional Monomers]

Examples of the components other than the dental polyfunctional monomers according to the first aspect of the invention may include (meth)acrylate group-containing monomers other than the polyfunctional monomers of the invention.

The (meth)acrylate group-containing monomer other than the polyfunctional monomers of the invention contains one or more (meth)acrylate groups in the molecule. The number of polymerizable groups present may be 1, or not less than 2.

The (meth)acrylate group-containing monomer other than the polyfunctional monomers of the invention may be composed of one compound, or composed of a mixture of two or more compounds.

Examples of the (meth)acrylate group-containing monomers other than the polyfunctional monomers, which have only one polymerizable group, include monomers represented by the general formula (21) below.

[Chem. 42]

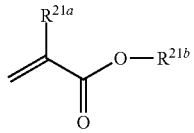
(21)

In the general formula (21), $R^{21a}$ represents hydrogen or a methyl group, and $R^{21b}$ represents a $C_{1-20}$ monovalent organic group which may contain oxygen or nitrogen.

Examples of the monovalent organic groups include hydrocarbon groups, for example, $C_{1-20}$ acyclic hydrocarbon groups such as alkyl groups, alkenyl groups and alkynyl groups, and $C_{1-20}$ cyclic hydrocarbon groups such as cycloalkyl groups, cycloalkenyl groups, cycloalkynyl groups and aryl groups; and $C_{1-20}$ oxygen-containing hydrocarbon groups such as those groups corresponding to the above hydrocarbon groups except that oxygen is introduced between at least part of the carbon atoms forming carbon-carbon bonds (but oxygen atoms are not inserted contiguously), for example, alkoxyalkyl groups, alkoxyalkylene glycol groups and tetrahydrofurfuryl groups. The $C_{1-20}$ cyclic hydrocarbon groups may have acyclic hydrocarbon moieties. Further, the acyclic hydrocarbon moieties present in these groups may be linear or branched.

In the case where the $C_{1-20}$ hydrocarbon groups or the $C_{1-20}$ oxygen-containing hydrocarbon groups contain linear alkylene moieties, at least one of the methylene groups in such moieties may be substituted by an ester bond, an amide bond, a carbonate bond, a urethane bond (a carbamoyl group) or a urea bond (but the methylene groups are not substituted contiguously).

Further, hydrogen atoms present in the organic groups such as the $C_{1-20}$ hydrocarbon groups and the $C_{1-20}$ oxygen-containing hydrocarbon groups may be substituted by acid groups such as carboxyl groups and phosphate groups, and functional groups such as hydroxyl groups, amino groups and epoxy groups.

Examples of the methacryloyl-containing compounds represented by the general formula (21) include methyl methacrylate, ethyl methacrylate, propyl methacrylate, butyl methacrylate, hexyl methacrylate, cyclohexyl methacrylate, ethoxydiethylene glycol methacrylate, methoxytriethylene glycol methacrylate, phenoxyethyl methacrylate, 2-hydroxyethyl methacrylate, 2-hydroxypropyl methacrylate, 2-hydroxybutyl methacrylate, 2-hydroxy-3-phenoxypropyl methacrylate, 4-hydroxybutyl methacrylate and 1,4-cyclohexanedimethanol monomethacrylate.

Examples of the methacryloyl-containing compounds represented by the general formula (21) include methyl acrylate, ethyl acrylate, propyl acrylate, butyl acrylate, hexyl acrylate, cyclohexyl acrylate, ethoxydiethylene glycol acrylate, methoxytriethylene glycol acrylate, phenoxyethyl acrylate, 2-hydroxyethyl acrylate, 2-hydroxypropyl acrylate, 2-hydroxybutyl acrylate, 2-hydroxy-3-phenoxypropyl acrylate, 4-hydroxybutyl acrylate and 1,4-cyclohexanedimethanol monoacrylate.

Examples of the (meth)acrylate group-containing monomers other than the polyfunctional monomers of the invention, which have two or more polymerizable groups, include monomers represented by the general formula (22) below.

[Chem. 43]

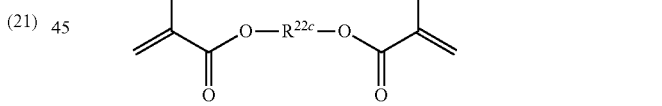
(22)

In the general formula (22), $R^{22a}$ and $R^{22b}$ each represent hydrogen or a methyl group and may be the same as or different from each other; and $R^{22c}$ represents a $C_{1-40}$ divalent organic group which may contain oxygen or nitrogen.

Examples of the divalent organic groups include hydrocarbon groups, for example, $C_{1-40}$ acyclic hydrocarbon groups such as alkylene groups, alkenylene groups and alkynylene groups, and $C_{1-40}$ cyclic hydrocarbon groups such as cycloalkylene groups, cycloalkenylene groups, cycloalkynylene groups and arylene groups; and $C_{1-40}$ oxygen-containing hydrocarbon groups such as those groups corresponding to the above hydrocarbon groups except that oxygen is introduced between at least part of the carbon atoms forming carbon-carbon bonds (but oxygen atoms are not inserted contiguously) for example, oxyalkylene groups. The $C_{1-40}$ cyclic hydrocarbon groups may have acyclic hydrocarbon moieties. Further, the acyclic hydrocarbon moieties present in these groups may be linear or branched.

In the case where the $C_{1-40}$ hydrocarbon groups or the $C_{1-40}$ oxygen-containing hydrocarbon groups contain linear alkylene moieties, at least one of the methylene groups in such moieties may be substituted by an ester bond, an amide bond, a carbonate bond, a urethane bond (a carbamoyl group) or a urea bond (but the methylene groups are not substituted contiguously).

Further, hydrogen atoms present in the organic groups such as the $C_{1-40}$ hydrocarbon groups and the $C_{1-40}$ oxygen-containing hydrocarbon groups may be substituted by acid groups such as carboxyl groups and phosphate groups, functional groups such as hydroxyl groups, amino groups and epoxy groups, and polymerizable groups such as acryloyl groups and methacryloyl groups.

Among the monomers represented by the general formula (22), some preferred monomers are those monomers in which $R^{22c}$ is a linear alkylene group having 2 to 20 carbon atoms, preferably 4 to 12 carbon atoms.

Examples of the compounds which correspond to the above preferred monomers and have methacryloyl groups include 1,4-butanediol dimethacrylate, 1,6-hexanediol dimethacrylate, 1,8-octanediol dimethacrylate, 1,9-nonanediol dimethacrylate and 1,10-decanediol dimethacrylate.

Examples of the compounds which correspond to the above preferred monomers and have acryloyl groups include 1,4-butanediol diacrylate, 1,6-hexanediol diacrylate, 1,8-octanediol diacrylate, 1,9-nonanediol diacrylate and 1,10-decanediol diacrylate.

Among the monomers represented by the general formula (22), other preferred monomers are those monomers in which $R^{22c}$ is a linear oxyalkylene group having 2 to 20 carbon atoms, preferably 4 to 12 carbon atoms.

Examples of the compounds which correspond to the above preferred monomers and have methacryloyl groups include ethylene glycol dimethacrylate, diethylene glycol dimethacrylate, triethylene glycol dimethacrylate, tetraethylene glycol dimethacrylate, polyethylene glycol dimethacrylate, tripropylene glycol dimethacrylate, tetrapropylene glycol dimethacrylate and polypropylene glycol dimethacrylate.

Examples of the compounds which correspond to the above preferred monomers and have acryloyl groups include ethylene glycol diacrylate, diethylene glycol diacrylate, triethylene glycol diacrylate, tetraethylene glycol diacrylate, polyethylene glycol diacrylate, tripropylene glycol diacrylate, tetrapropylene glycol diacrylate and polypropylene glycol diacrylate.

Among the monomers represented by the general formula (22), other preferred monomers are carbamoyl group-containing monomers represented by the general formula (23) below.

[Chem. 44]

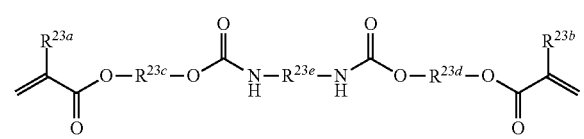

(23)

In the general formula (23), $R^{23a}$ and $R^{23b}$ each represent hydrogen or a methyl group and may be the same as or different from each other; and $R^{23c}$ and $R^{23d}$ each represent a $C_{1-12}$ divalent organic group which may contain oxygen, and may be the same as or different from each other.

Examples of the divalent organic groups include hydrocarbon groups, for example, $C_{1-12}$ acyclic hydrocarbon groups such as alkylene groups, and $C_{1-12}$ cyclic hydrocarbon groups such as cycloalkylene groups and arylene groups; and $C_{1-12}$ oxygen-containing hydrocarbon groups such as those groups corresponding to the above hydrocarbon groups except that oxygen is introduced between at least part of the carbon atoms forming carbon-carbon bonds (but oxygen atoms are not inserted contiguously), for example, oxyalkylene groups. The $C_{1-12}$ cyclic hydrocarbon groups may have acyclic hydrocarbon moieties. Further, the acyclic hydrocarbon moieties present in these groups may be linear or branched.

Further, hydrogen atoms present in the organic groups such as the $C_{1-12}$ hydrocarbon groups and the $C_{1-12}$ oxygen-containing hydrocarbon groups may be substituted by acid groups such as carboxyl groups and phosphate groups, functional groups such as hydroxyl groups, amino groups and epoxy groups, and polymerizable groups such as acryloyl groups and methacryloyl groups.

In the general formula (23), $R^{23e}$ represents a $C_{1-20}$ divalent organic group which may contain oxygen.

Examples of the divalent organic groups include hydrocarbon groups, for example, $C_{1-20}$ acyclic hydrocarbon groups such as alkylene groups, and $C_{1-20}$ cyclic hydrocarbon groups such as cycloalkylene groups and arylene groups; and $C_{1-20}$ oxygen-containing hydrocarbon groups such as those groups corresponding to the above hydrocarbon groups except that oxygen is introduced between at least part of the carbon atoms forming carbon-carbon bonds (but oxygen atoms are not inserted contiguously), for example, oxyalkylene groups. The $C_{1-20}$ cyclic hydrocarbon groups may have acyclic hydrocarbon moieties. Further, the acyclic hydrocarbon moieties present in these groups may be linear or branched.

Further, hydrogen atoms present in the organic groups such as the $C_{1-20}$ hydrocarbon groups and the $C_{1-20}$ oxygen-containing hydrocarbon groups may be substituted by acid groups such as carboxyl groups and phosphate groups, and functional groups such as hydroxyl groups, amino groups and epoxy groups.

Examples of the acryloyl group-containing compounds represented by the general formula (23) include urethane acrylates formed by the reaction between a hydroxyacrylate such as 2-hydroxyethyl acrylate, 2-hydroxypropyl acrylate, 2-hydroxybutyl acrylate, 2-hydroxy-3-phenoxypropyl acrylate, 4-hydroxybutyl acrylate or 1,4-cyclohexanedimethanol monoacrylate, and a diisocyanate such as 2,4- or 2,6-toluene diisocyanate, 4,4'-, 2,4'- or 2,2'-diphenylmethane-diisocyanate, 1,6-hexamethylene diisocyanate, or 2,2,4- or 2,4,4-trimethyl-1,6-hexamethylene-diisocyanate. Examples of such urethane acrylates include 2,2,4-trimethylhexamethylene bis(2-carbamoyloxyethyl) diacrylate).

Among the (meth)acryloyl group-containing compounds represented by the general formula (23), other preferred compounds may be at least one selected from the group consisting of compounds represented by the general formulas (24a) to (24e).

[Chem. 45]
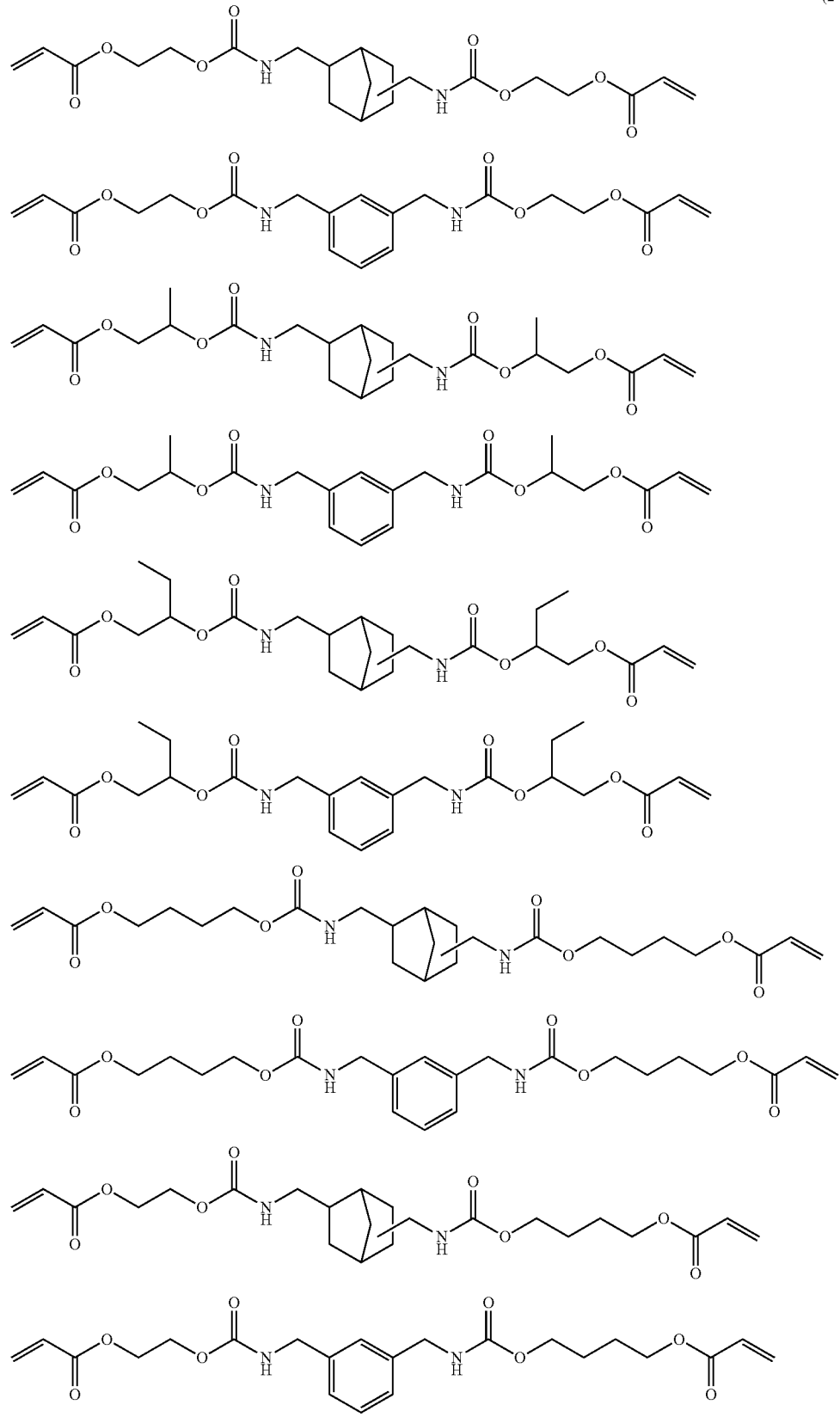
(24a)

-continued
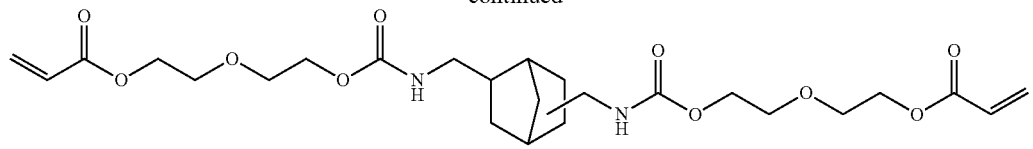
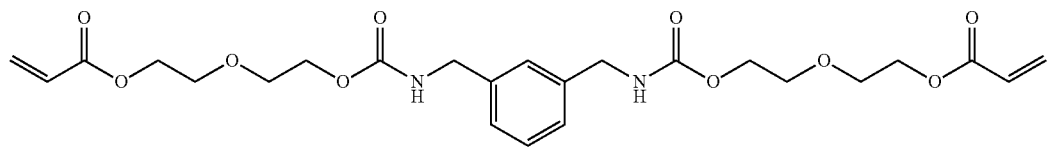
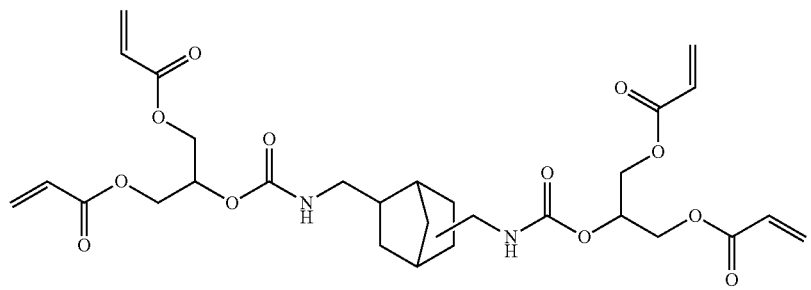
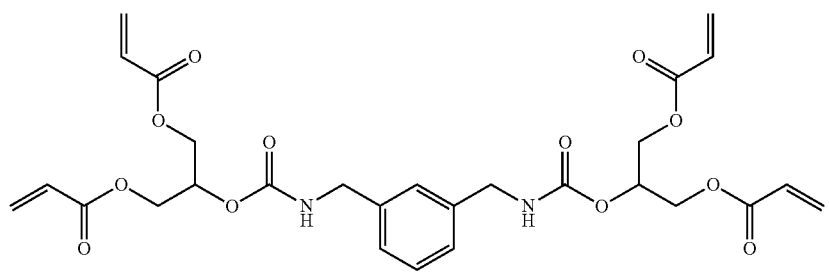
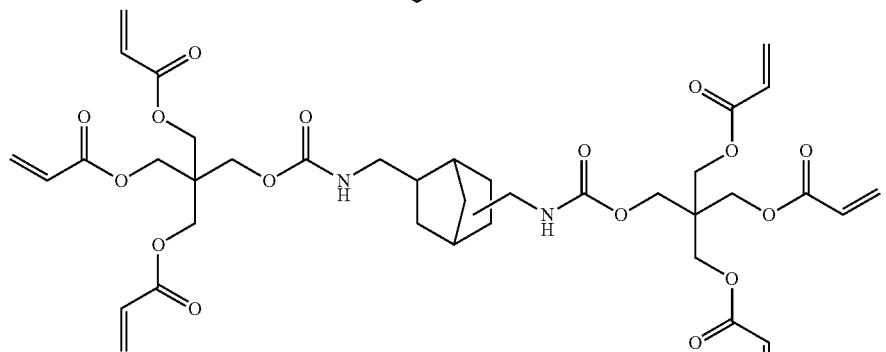
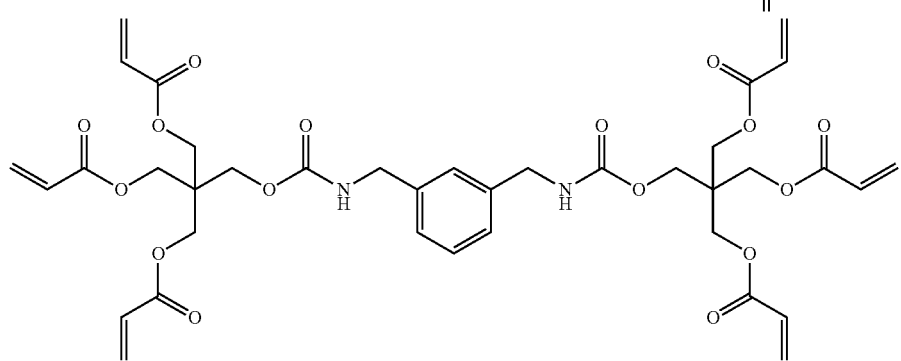

(24b)
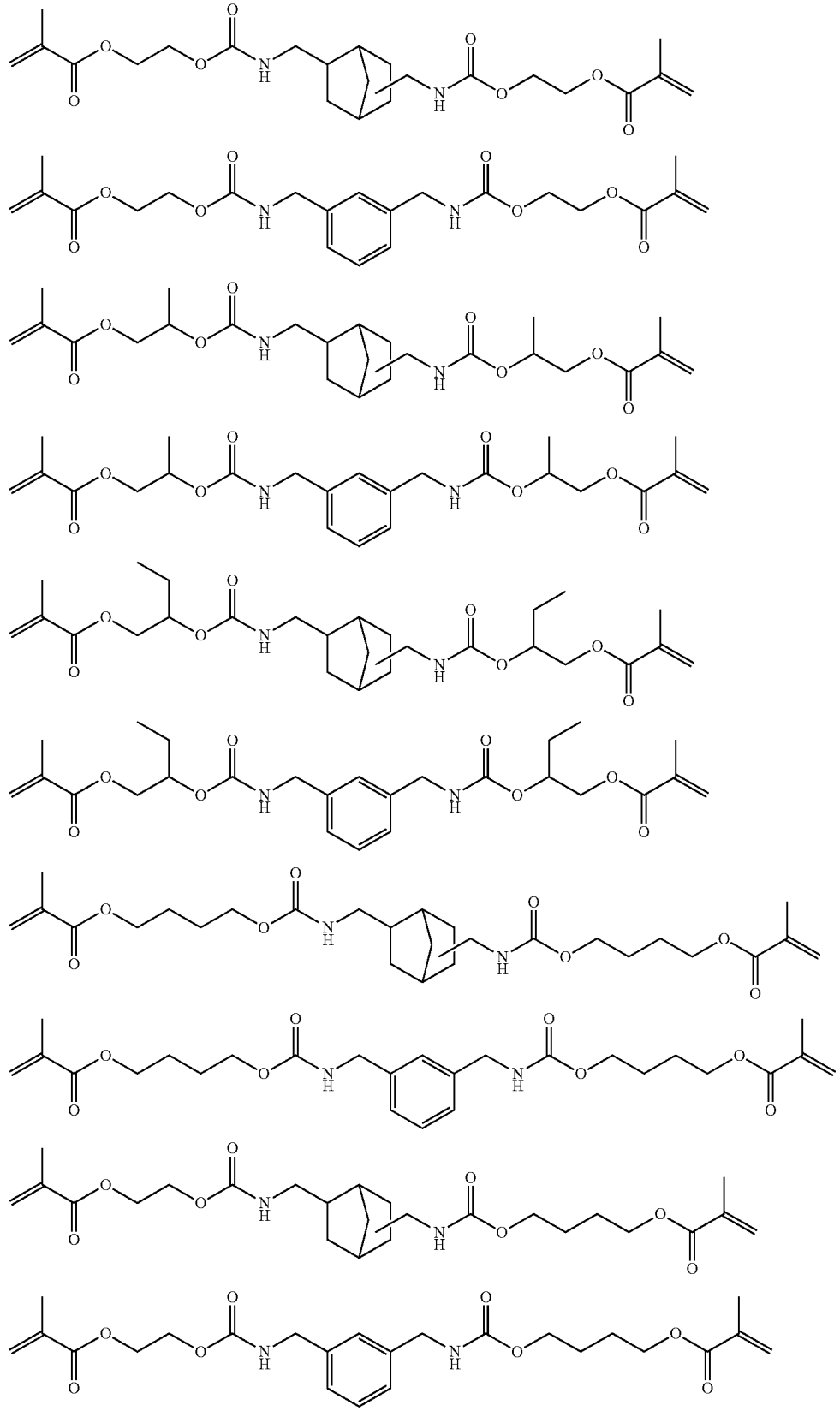

-continued
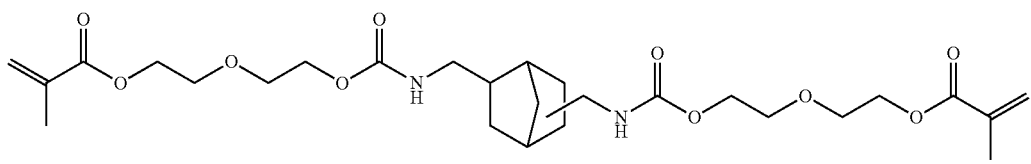
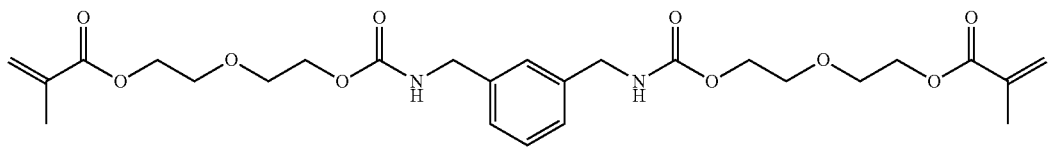
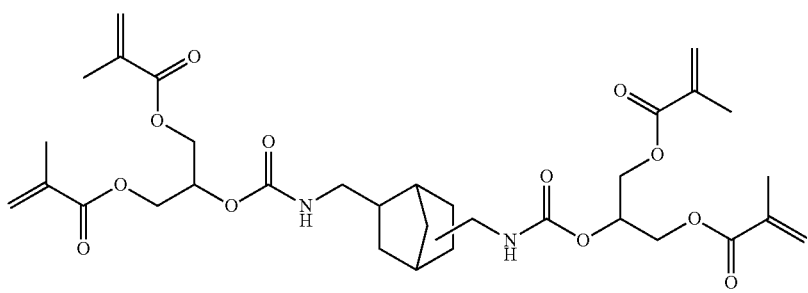
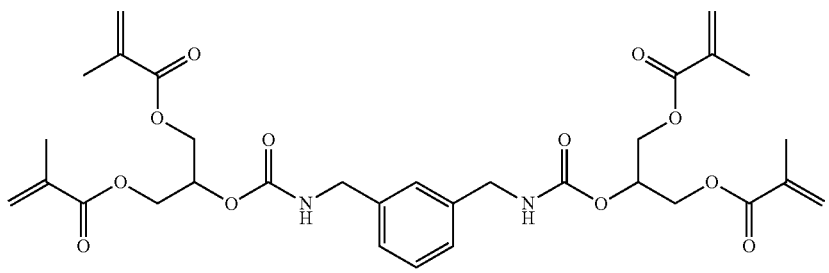
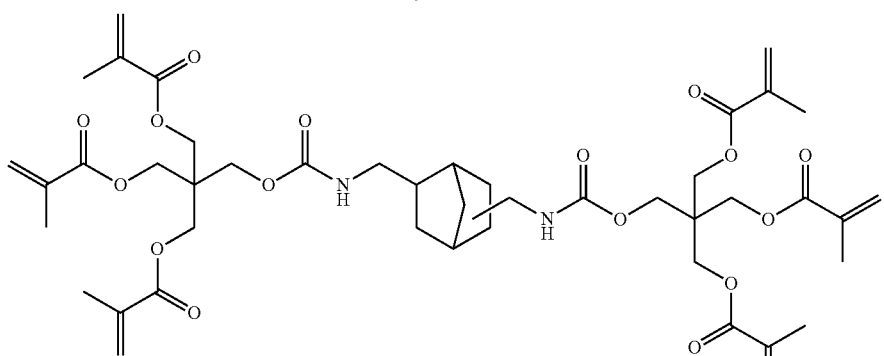
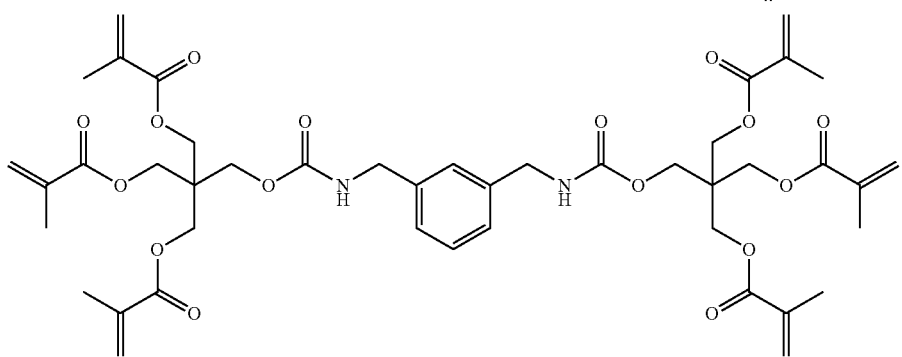

[Chem. 47]
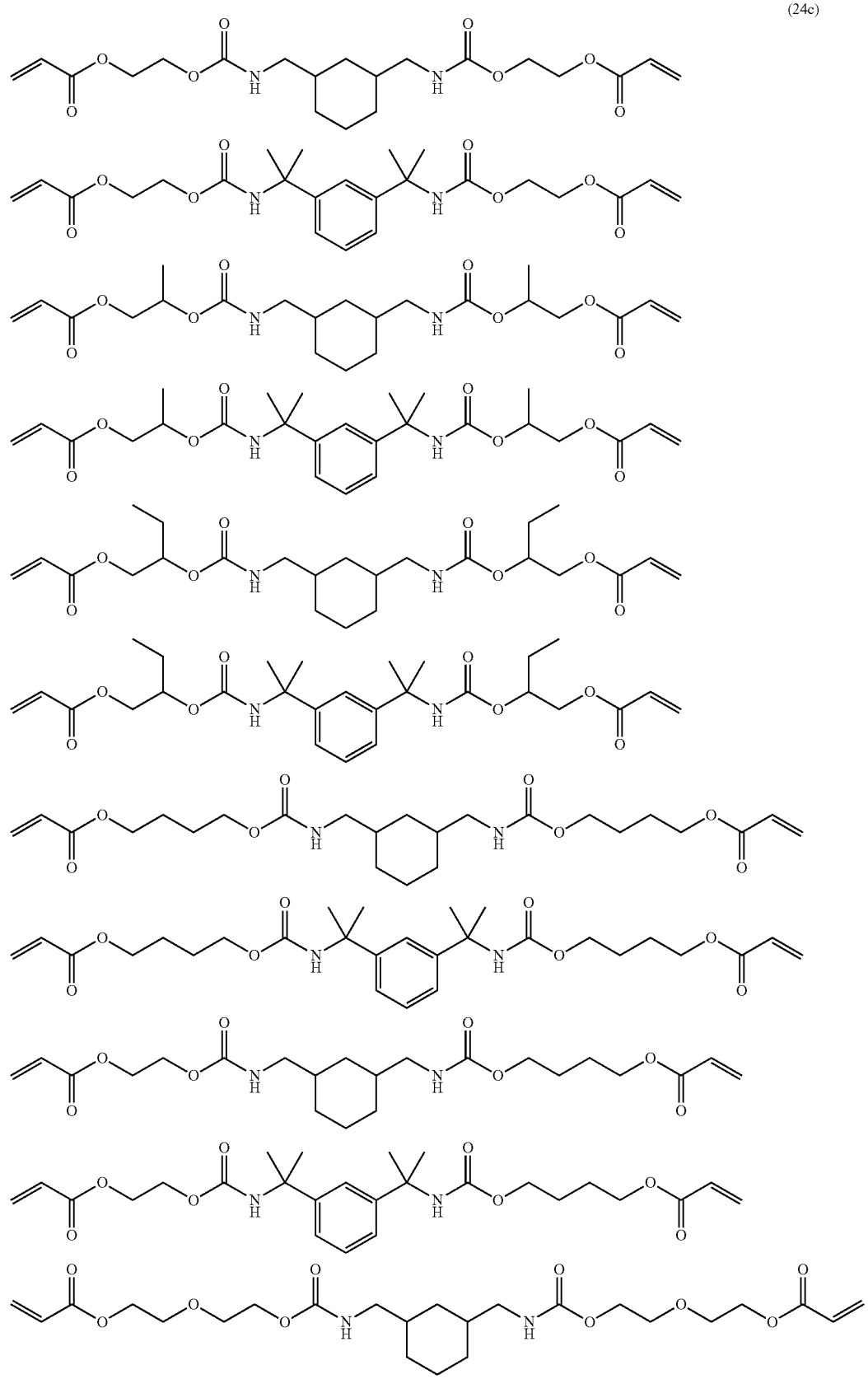
(24c)

-continued
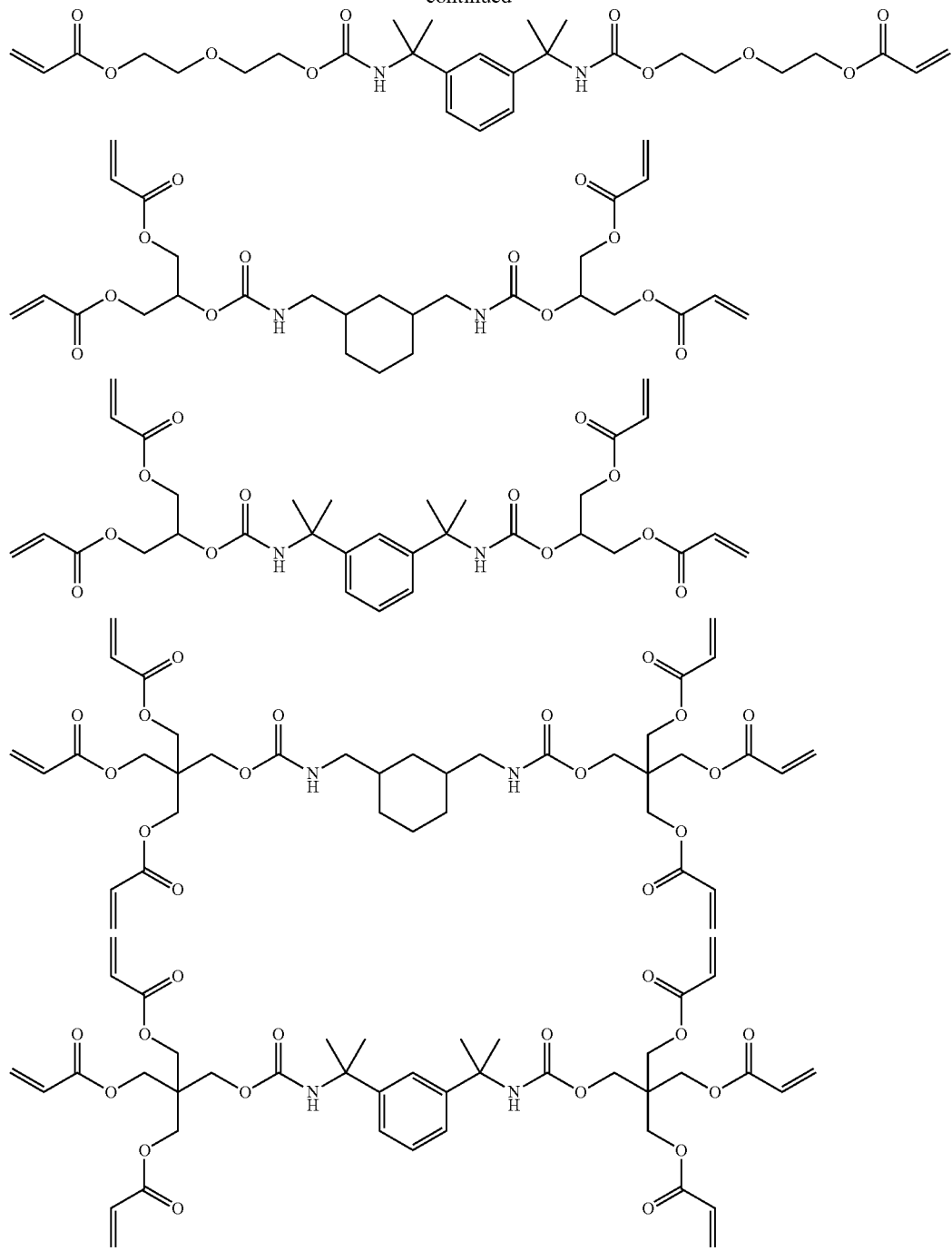
[Chem. 48]
(24d)
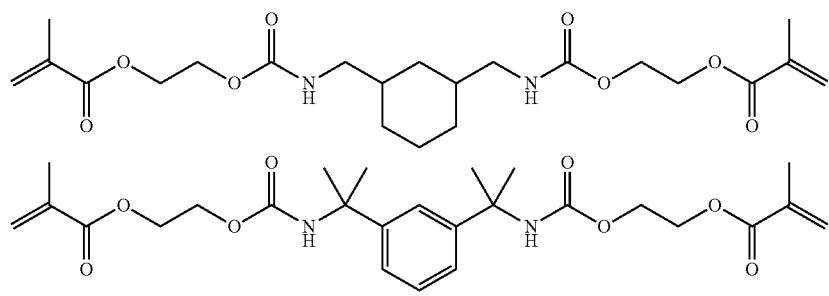

-continued
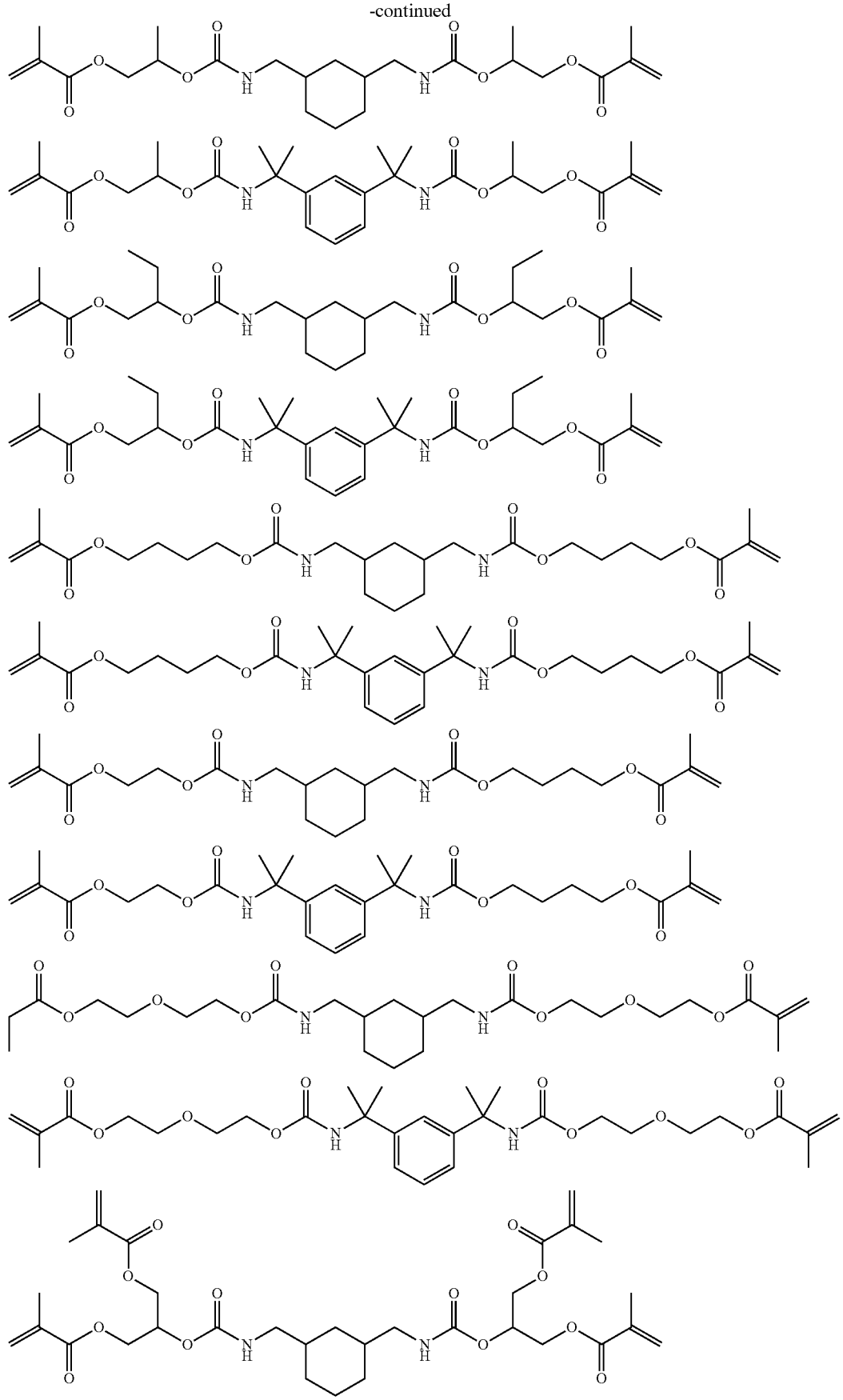

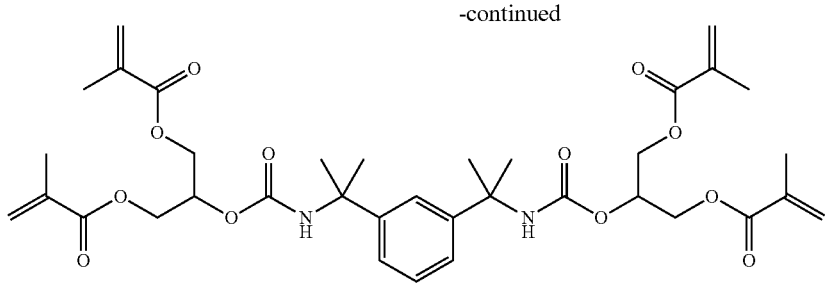
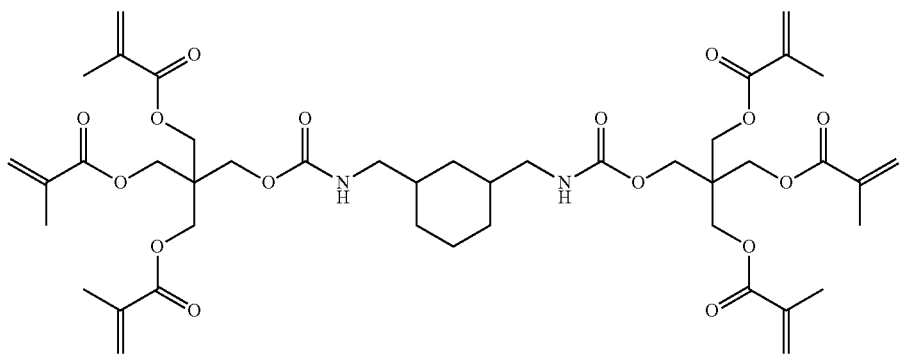
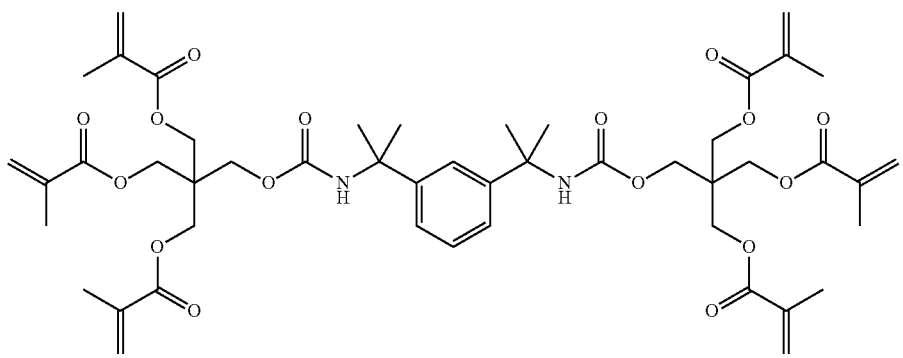
[Chem. 49]
(24e)
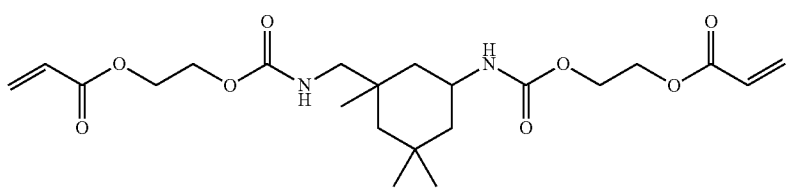
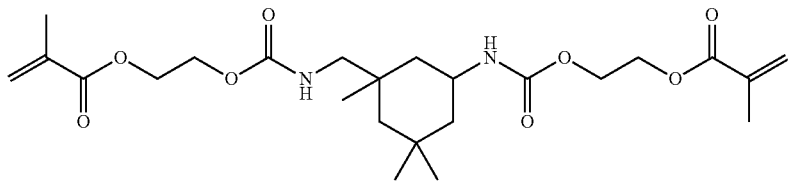
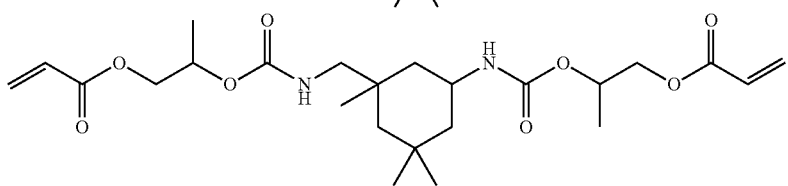

-continued
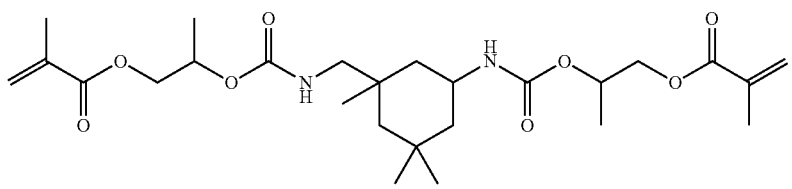
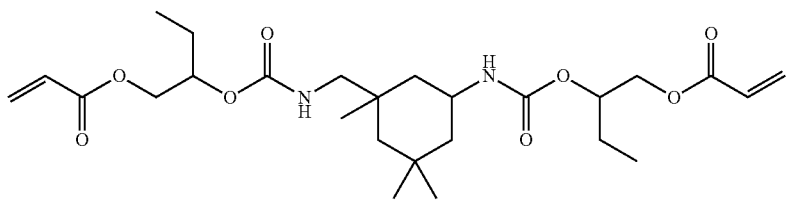
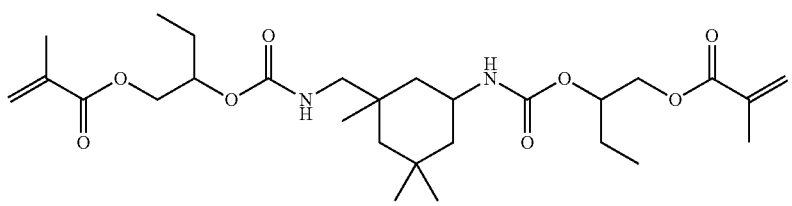
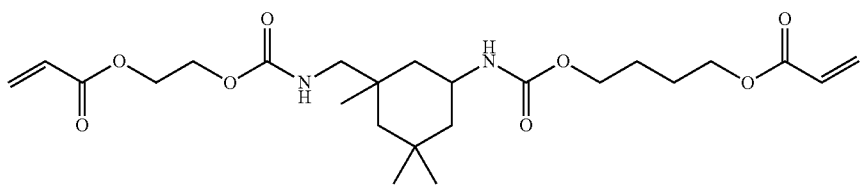
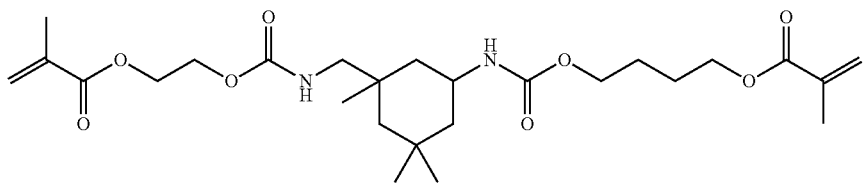
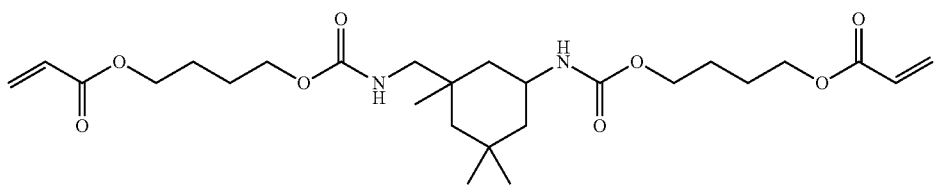
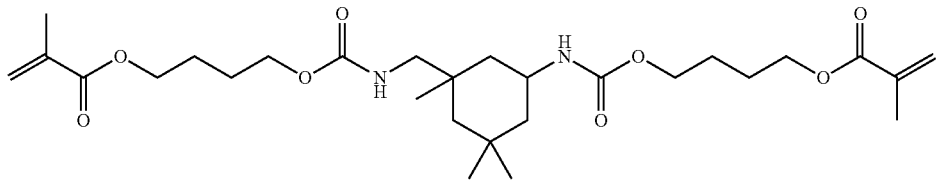
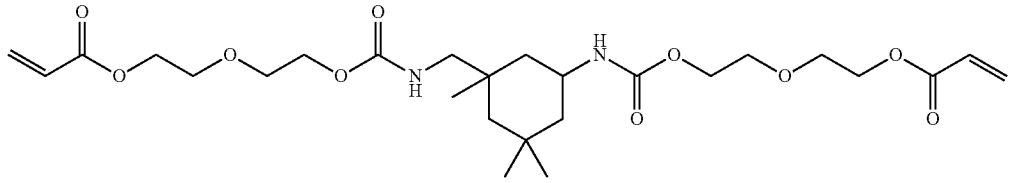
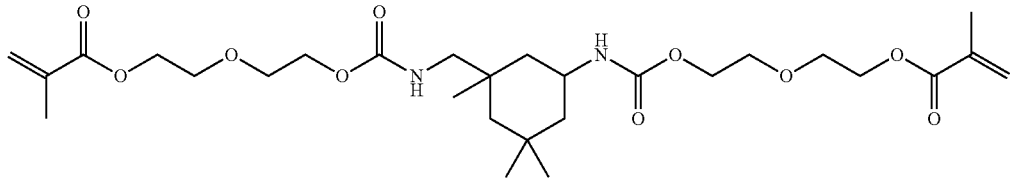

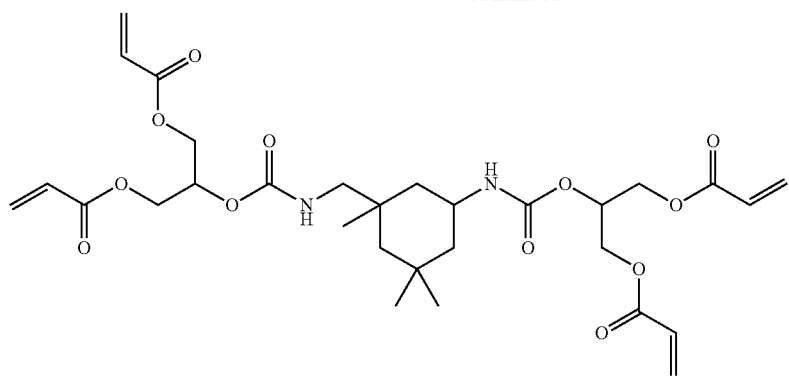
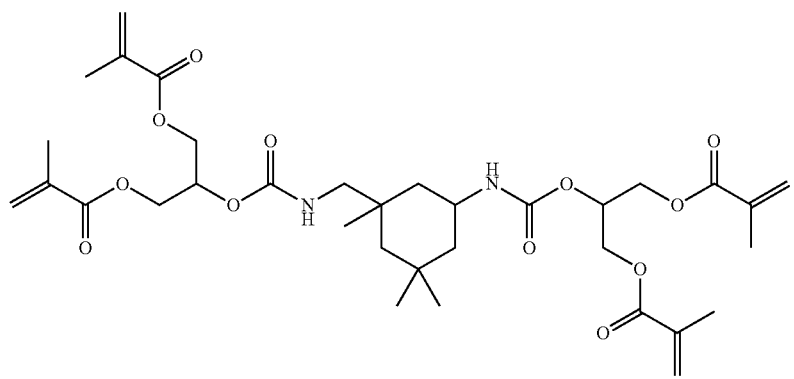
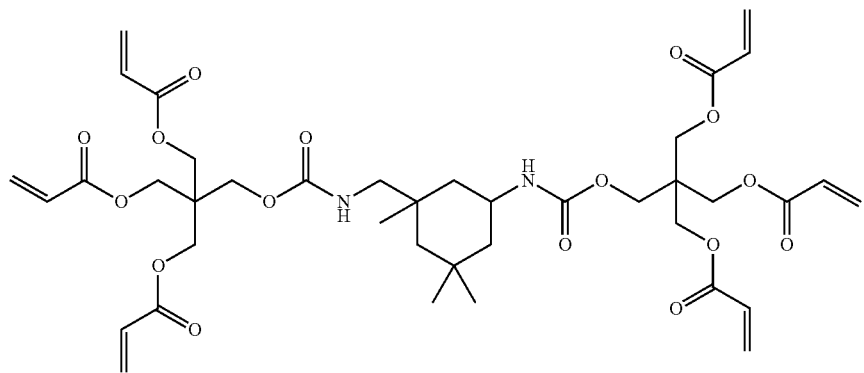
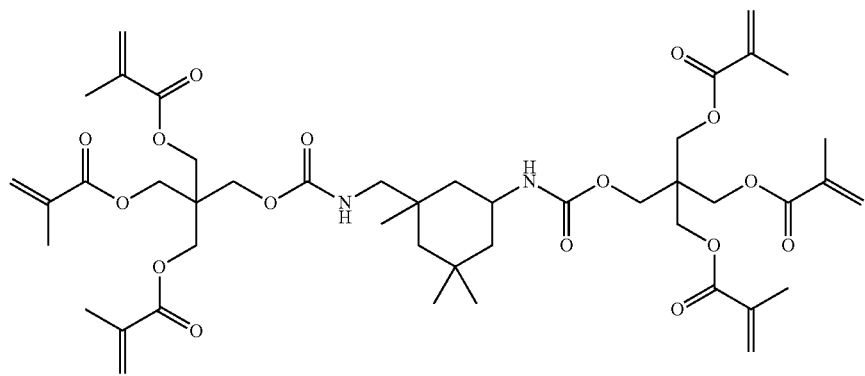

Further, among the monomers represented by the general formula (22), other preferred monomers may be monomers of the general formula (25) below.

[Chem. 50]

(25)

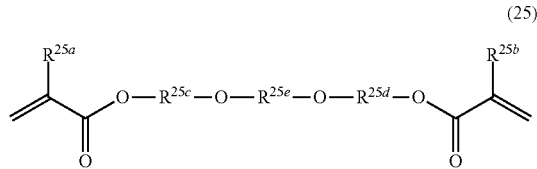

In the general formula (25), $R^{25a}$ and $R^{25b}$ each represent hydrogen or a methyl group and may be the same as or different from each other; and $R^{25c}$ and $R^{25d}$ each represent a $C_{1-12}$ divalent organic group which may contain oxygen, and may be the same as or different from each other. Examples of the divalent organic groups include hydrocarbon groups, for example, $C_{1-12}$ acyclic hydrocarbon groups such as alkylene groups, and $C_{1-12}$ cyclic hydrocarbon groups such as cycloalkylene groups and arylene groups; and $C_{1-12}$ oxygen-containing hydrocarbon groups such as those groups corresponding to the above hydrocarbon groups except that oxygen is introduced between at least part of the carbon atoms forming carbon-carbon bonds (but oxygen atoms are not inserted contiguously), for example, oxyalkylene groups. The $C_{1-12}$ cyclic hydrocarbon groups may have acyclic hydrocarbon moieties. Further, the acyclic hydrocarbon moieties present in these groups may be linear or branched. Further, hydrogen atoms present in the organic groups such as the $C_{1-12}$ hydrocarbon groups and the $C_{1-12}$ oxygen-containing hydrocarbon groups may be substituted by acid groups such as carboxyl groups and phosphate groups, functional groups such as hydroxyl groups, amino groups and epoxy groups, and polymerizable groups such as acryloyl groups and methacryloyl groups.

In the general formula (25), $R^{25e}$ represents a $C_{1-20}$ divalent organic group which may contain oxygen. Examples of the divalent organic groups include $C_{1-20}$ hydrocarbon groups such as alkylene groups, cycloalkylene groups and arylene groups; and $C_{1-20}$ oxygen-containing hydrocarbon groups such as those groups corresponding to the above hydrocarbon groups except that oxygen is introduced between at least part of the carbon atoms forming carbon-carbon bonds (but oxygen atoms are not inserted contiguously), for example, oxyalkylene groups. The $C_{1-20}$ cyclic hydrocarbon groups may have acyclic hydrocarbon moieties. Further, hydrogen atoms present in the organic groups such as the $C_{1-20}$ hydrocarbon groups and the $C_{1-20}$ oxygen-containing hydrocarbon groups may be substituted by acid groups such as carboxyl groups and phosphate groups, and functional groups such as hydroxyl groups, amino groups and epoxy groups.

Examples of the methacryloyl group-containing compounds represented by the general formula (25) include 2,2-bis[4-(3-methacryloyloxy-2-hydroxypropoxy)phenyl]propane (Bis-GMA), ethylene oxide-modified bisphenol A dimethacrylate and propylene oxide-modified bisphenol A dimethacrylate.

Examples of the acryloyl group-containing compounds represented by the general formula (25) include 2,2-bis[4-(3-acryloyloxy-2-hydroxypropoxy)phenyl]propane, ethylene oxide-modified bisphenol A diacrylate and propylene oxide-modified bisphenol A diacrylate.

When the dental material containing the dental polyfunctional monomer of the invention is used in such an application as dental adhesive materials, it is preferable that the dental material contain, as a (meth)acrylate group-containing monomer other than the polyfunctional monomers of the invention, a monomer exhibiting a bonding function. Examples of such adhesive (meth)acrylate group-containing monomers other than the polyfunctional monomers of the invention include monomers having at least one polymerizable group selected from methacryloyl groups and acryloyl groups, and an acidic group. Examples of the acidic groups include phosphate residues, pyrophosphate residues, thiophosphate residues, carboxylate residues and sulfonate residues.

Examples of the monomers having a methacryloyl group and a phosphate residue include 2-methacryloyloxyethyl dihydrogen phosphate, 9-methacryloyloxynonyl dihydrogen phosphate, 10-methacryloyloxydecyl dihydrogen phosphate, 11-methacryloyloxyundecyl dihydrogen phosphate, 20-methacryloyloxyeicosyl dihydrogen phosphate, 1,3-dimethacryloyloxypropyl-2-dihydrogen phosphate, 2-methacryloyloxyethyl phenyl phosphoric acid, 2-methacryloyloxyethyl 2'-bromoethyl phosphoric acid, methacryloyloxyethyl phenyl phosphonate, and acid chlorides of these compounds.

Examples of the monomers having a acryloyl group and a phosphate residue include 2-acryloyloxyethyl dihydrogen phosphate, 9-acryloyloxynonyl dihydrogen phosphate, 10-acryloyloxydecyl dihydrogen phosphate, 11-acryloyloxyundecyl dihydrogen phosphate, 20-acryloyloxyeicosyl dihydrogen phosphate, 1,3-diacryloyloxypropyl-2-dihydrogen phosphate, 2-acryloyloxyethyl phenyl phosphoric acid, 2-acryloyloxyethyl 2'-bromoethyl phosphoric acid, acryloyloxyethyl phenyl phosphonate, and acid chlorides of these compounds.

Examples of the monomers having a methacryloyl group and a pyrophosphate residue include di(2-methacryloyloxyethyl) pyrophosphate, and acid chlorides thereof.

Examples of the monomers having an acryloyl group and a pyrophosphate residue include di(2-acryloyloxyethyl) pyrophosphate, and acid chlorides thereof.

Examples of the monomers having a methacryloyl group and a thiophosphate residue include 2-methacryloyloxyethyl dihydrogen dithiophosphate, 10-methacryloyloxydecyl dihydrogen thiophosphate, and acid chlorides of these compounds.

Examples of the monomers having an acryloyl group and a thiophosphate residue include 2-acryloyloxyethyl dihydrogen dithiophosphate, 10-acryloyloxydecyl dihydrogen thiophosphate, and acid chlorides of these compounds.

Examples of the monomers having a methacryloyl group and a carboxylate residue include 4-methacryloyloxyethoxycarbonylphthalic acid, 5-methacryloylaminopentylcarboxylic acid, 11-methacryloyloxy-1,1-undecanedicarboxylic acid, and acid chlorides and acid anhydrides of these compounds.

Examples of the monomers having an acryloyl group and a carboxylate residue include 4-acryloyloxyethoxycarbonylphthalic acid, 5-acryloylaminopentylcarboxylic acid, 11-acryloyloxy-1,1-undecanedicarboxylic acid, and acid chlorides and acid anhydrides of these compounds.

Examples of the monomers having a methacryloyl group and a sulfonate residue include 2-sulfoethyl methacrylate and 2-methacrylamido-2-methylpropanesulfonic acid.

Examples of the monomers having an acryloyl group and a sulfonate residue include 2-sulfoethyl acrylate and 2-acrylamido-2-methylpropanesulfonic acid.

[Polymerization Initiators]

Among the components other than the dental polyfunctional monomers of the invention in the dental materials according to the first aspect of the invention, other components may be polymerization initiators.

The polymerization initiator may be any of general polymerization initiators used in the dental field, and is usually selected in consideration of the polymerizability of the polymerizable monomers, and the polymerization conditions.

In the case of self curing, for example, a redox polymerization initiator that is a combination of an oxidant and a reductant is preferable. When using a redox polymerization initiator, an oxidant and a reductant which are separately packaged need to be mixed with each other immediately before use.

The oxidants are not particularly limited. Examples thereof include organic peroxides such as diacyl peroxides, peroxy esters, dialkyl peroxides, peroxyketals, ketone peroxides and hydroperoxides. Examples of the organic peroxides include such diacyl peroxides as benzoyl peroxide, 2,4-dichlorobenzoyl peroxide and m-toluoyl peroxide; such peroxy esters as t-butyl peroxybenzoate, bis-t-butyl peroxyisophthalate, 2,5-dimethyl-2,5-bis(benzoylperoxy)hexane, t-butyl peroxy-2-ethylhexanoate and t-butyl peroxyisopropyl carbonate; such dialkyl peroxides as dicumyl peroxide, di-t-butyl peroxide and lauroyl peroxide; such peroxyketals as 1,1-bis(t-butylperoxy)-3,3,5-trimethylcyclohexane; such ketone peroxides as methyl ethyl ketone peroxide; and such hydroperoxides as t-butyl hydroperoxide.

The reductants are not particularly limited, but tertiary amines are usually used. Examples of the tertiary amines include N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-i-propylaniline, N,N-dimethyl-4-t-butylaniline, N,N-dimethyl-3,5-di-t-butylaniline, N,N-bis(2-hydroxyethyl)-p-toluidine, N,N-bis(2-hydroxyethyl)-3,5-dimethylaniline, N,N-bis(2-hydroxyethyl)-3,4-dimethylaniline, N,N-bis(2-hydroxyethyl)-4-ethylaniline, N,N-bis(2-hydroxyethyl)-4-i-propylaniline, N,N-bis(2-hydroxyethyl)-4-t-butylaniline, N,N-di(2-hydroxyethyl)-3,5-di-i-propylaniline, N,N-bis(2-hydroxyethyl)-3,5-di-t-butylaniline, ethyl 4-dimethylaminobenzoate, n-butoxyethyl 4-dimethylaminobenzoate, (2-methacryloyloxy)ethyl 4-dimethylaminobenzoate, trimethylamine, triethylamine, N-methyldiethanolamine, N-ethyldiethanolamine, N-n-butyldiethanolamine, N-lauryldiethanolamine, triethanolamine, (2-dimethylamino)ethyl methacrylate, N,N-bis(methacryloyloxyethyl)-N-methylamine, N,N-bis(methacryloyloxyethyl)-N-ethylamine, N,N-bis(2-hydroxyethyl)-N-methacryloyloxyethylamine, N,N-bis(methacryloyloxyethyl)-N-(2-hydroxyethyl)amine and tris(methacryloyloxyethyl)amine.

Besides these organic peroxide/amine systems, other redox polymerization initiators such as cumene hydroperoxide/thiourea systems, ascorbic acid/$Cu^{2+}$ salt systems and organic peroxide/amine/sulfinic acid (or sulfinate salt) systems may be used. Further, other polymerization initiators such as tributyl borane and organic sulfinic acids are also suitably used.

In the case of thermal polymerization with heating, it is preferable to use peroxides or azo compounds.

The peroxides are not particularly limited, and examples thereof include benzoyl peroxide, t-butyl hydroperoxide and cumene hydroperoxide. The azo compounds are not particularly limited, and examples thereof include azobisisobutyronitrile.

In the case of photopolymerization with the application of visible lights, suitable initiators are redox initiators such as α-diketones/tertiary amines, α-diketones/aldehydes and α-diketones/mercaptans.

Examples of the photopolymerization initiators, although not particularly limited to, include α-diketones/reductants, ketals/reductants and thioxanthones/reductants. Examples of the α-diketones include camphorquinone, benzil and 2,3-pentanedione. Examples of the ketals include benzyl dimethyl ketal and benzyl diethyl ketal. Examples of the thioxanthones include 2-chlorothioxanthone and 2,4-diethylthioxanthone. Examples of the reductants include tertiary amines such as Michler's ketone, 2-(dimethylamino)ethyl methacrylate, N,N-bis[(meth)acryloyloxyethyl]-N-methylamine, ethyl N,N-dimethylaminobenzoate, butyl 4-dimethylaminobenzoate, butoxyethyl 4-dimethylaminobenzoate, N-methyldiethanolamine, 4-dimethylaminobenzophenone, N,N-bis(2-hydroxyethyl)-p-toluidine and dimethylaminophenanthrol; aldehydes such as citronellal, lauryl aldehyde, phthalic dialdehyde, dimethylaminobenzaldehyde and terephthalaldehyde; and thiol group-containing compounds such as 2-mercaptobenzoxazole, decanethiol, 3-mercaptopropyltrimethoxysilane, 4-mercaptoacetophenone, thiosalicylic acid and thiobenzoic acid. Organic peroxides may be added to these redox systems. That is, α-diketone/organic peroxide/reductant systems may be suitably used.

In the case of photopolymerization with the application of UV lights, some suitable initiators are benzoin alkyl ethers and benzyl dimethyl ketal. Further, such photopolymerization initiators as (bis)acylphosphine oxides are also suitably used.

Of the (bis)acylphosphine oxides, examples of the acylphosphine oxides include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide and benzoyldi-(2,6-dimethylphenyl) phosphonate. Examples of the bisacylphosphine oxides include bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, bis-(2,6-dimethoxybenzoyl)phenylphosphine oxide, bis-(2,6-dimethoxybenzoyl)-2,4,4-trimethylpentylphosphine oxide, bis-(2,6-dimethoxybenzoyl)-2,5-dimethylphenylphosphine oxide, bis-(2,4,6-trimethylbenzoyl)phenylphosphine oxide and (2,5,6-trimethylbenzoyl)-2,4,4-trimethylpentylphosphine oxide. These (bis)acylphosphine oxide photopolymerization initiators may be used singly or in combination with various reductants such as amines, aldehydes, mercaptans and sulfinate salts. These reductants may be suitably used also in combination with the visible light photopolymerization initiators described hereinabove.

The polymerization initiators or the photopolymerization initiators may be used singly, or two or more thereof may be used in appropriate combination. The amount thereof is usually in the range of 0.01 to 20 parts by weight, preferably 0.1 to 5 parts by weight per 100 parts by weight of the dental material.

[Fillers]

Among the components other than the dental polyfunctional monomers of the invention in the dental materials according to the first aspect of the invention, other components may be fillers.

The filler may be any of general fillers used in the dental field. The fillers are usually broadly categorized into organic fillers and inorganic fillers.

Examples of the organic fillers include fine powders of polymethyl methacrylate, polyethyl methacrylate, methyl methacrylate-ethyl methacrylate copolymer, crosslinked polymethyl methacrylate, crosslinked polyethyl methacrylate, ethylene-vinyl acetate copolymer and styrene-butadiene copolymer.

Examples of the inorganic fillers include fine powders of various glasses (based on silicon dioxide and optionally containing oxides of, for example, heavy metals, boron and aluminum), various ceramics, diatomaceous earth, kaolin, clay minerals (such as montmorillonite), activated clay, synthetic zeolite, mica, calcium fluoride, ytterbium fluoride, calcium phosphate, barium sulfate, zirconium dioxide, titanium dioxide and hydroxyapatite. Of these inorganic fillers, those that are used as X-ray contrast agents are preferable. Specific examples of the inorganic fillers that are used as X-ray contrast agents include barium borosilicate glasses (such as Kimble Raysorb T3000, Schott 8235, Schott GM27884 and Schott GM39923), strontium boroaluminosilicate glasses (such as Raysorb T4000, Schott G018-093 and Schott GM32087), lanthanum glasses (such as Schott GM31684), fluoroaluminosilicate glasses (such as Schott G018-091 and Schott G018-117), and boroaluminosilicate glasses containing zirconium and/or cesium (such as Schott G018-307, G018-308 and G018-310)

Further, an organic inorganic composite filler may be used which is obtained by adding a polymerizable monomer beforehand to the inorganic filler to give a paste, which is then cured by polymerization and crushed.

In a preferred aspect of the dental material, the material contains a microfiller having a particle diameter of not more than 0.1 μm. Such a material is suited as a dental composite resin. Preferred examples of the materials for such micron size fillers include silica (for example, product name: AEROSIL), alumina, zirconia and titania. The addition of such a micron size inorganic filler is advantageous in order for a cured product of the composite resin to achieve high polish and smoothness by being polished.

These fillers may have been surface treated with agents such as silane coupling agents in accordance with purposes. Examples of such surface treating agents include known silane coupling agents, for example, organosilicon compounds such as γ-methacryloxyalkyltrimethoxysilanes (the number of carbon atoms between the methacryloxy group and the silicon atom: 3 to 12), γ-methacryloxyalkyltriethoxysilanes (the number of carbon atoms between the methacryloxy group and the silicon atom: 3 to 12), vinyltrimethoxysilane, vinylethoxysilane and vinyltriacetoxysilane. The surface treating agent is usually used with a concentration in the range of 0.1 to 20 parts by weight, and preferably 1 to 10 parts by weight per 100 parts by weight of the filler.

The fillers may be used singly, or two or more thereof may be used in appropriate combination. The amount of the filler may be determined appropriately in consideration of handling properties (viscosity) of the composite resin paste and mechanical properties of cured products of the paste. The amount is usually 10 to 2000 parts by weight, preferably 50 to 1000 parts by weight, and more preferably 100 to 600 parts by weight per 100 parts by weight of all the components present in the dental material except the filler.

The above-mentioned dental materials containing a (meth)acryloyl group-containing monomer, a polymerization initiator and a filler are sometimes called composite resins.

[Other Components]

The dental material according to the first aspect of the invention may appropriately contain components other than the dental polyfunctional monomers of the invention, the polymerizable monomer other than the polyfunctional monomers of the invention (for example the (meth)acrylate group-containing monomer other than the polyfunctional monomers of the invention, or the epoxy group-containing monomer), the polymerization initiator and the filler in accordance with the purpose. For example, the dental material may contain the aforementioned polymerization inhibitor for enhancing storage stability. To control the color tone, known colorants such as pigments and dyes may be added. Further, known reinforcing materials such as fibers may be added to increase the strength of cured products. Further, solvents such as water, ethanol and acetone may be added.

[Ratio of Components]

The amount of the polyfunctional monomer according to the first aspect of the invention based on the amount of the dental material is not particularly limited, and is, for example, in the range of 0.1 to 99%. The preferred amount of the polyfunctional monomer may vary depending on the purpose of the dental material. For example, the polyfunctional monomer is added in an amount of 1 to 50 wt %, preferably 3 to 30 wt % based on the amount of the polymerizable monomer components (the dental polyfunctional monomer of the invention and the polymerizable monomer other than the polyfunctional monomers of the invention (for example the (meth)acrylate group-containing monomer other than the polyfunctional monomers of the invention, or the epoxy group-containing monomer)). In particular, when the dental material is used as a filling composite resin, a tooth crowning hard resin, a denture base resin or a CAD/CAM resin block, the amount of the polyfunctional monomer is preferably 1 to 50 wt %, more preferably 3 to 30 wt % based on the amount of polymerizable monomer components. When the dental material is used as a dental adhesive material (orthodontic adhesive material, bonding material, adhesive resin cement, filling adhesive composite resin, resin glass ionomer cement or the like), a dental primer or a dental fissure sealant, the amount of the polyfunctional monomer is preferably 1 to 50 wt %, more preferably 3 to 20 wt % based on the amount of polymerizable monomer components.

(Reverse Mutation Test)

The dental material of the polyfunctional monomer according to the first aspect of the invention may be negative in a reverse mutation test. The reverse mutation test (Ames test) is conducted in accordance with the same procedure as that of the above-described reverse mutation test except that the dental material of the polyfunctional monomer according to the first aspect of the invention is used instead of the dental monomer composition according to the first aspect of the invention.

(Cell Test in NRU Method)

The dental material of the polyfunctional monomer according to the first aspect of the invention may allow the relative cell survival rate to fall within a certain range in a cell test in the NRU method using Balb/3T3 cells. The cell test is conducted in accordance with the same procedure as that of the above-described cell test in the NRU method except that the dental material of the polyfunctional monomer according to the first aspect of the invention is used instead of the dental monomer composition according to the first aspect of the invention. Further, the concentration of the test substance of the test material (the dental polyfunctional monomer of the dental material) in the test solution, and the relative cell growth rate (%) in the dental material may be the same as in the case of the dental monomer composition according to the first aspect of the invention.
(Cell Test in WST Method)

The dental material of the polyfunctional monomer according to the first aspect of the invention may allow the relative cell growth rate to fall within a certain range in a cell test in the WST method using Balb/3T3 cells. The cell test is conducted in accordance with the same procedure as that of the above-described cell test in the WST method except that the dental material of the polyfunctional monomer according to the first aspect of the invention is used in place of the dental monomer composition according to the first aspect of the invention. Further, the concentration of the test substance of the test material (the dental polyfunctional monomer of the dental material) in the test solution, and the relative cell growth rate (%) in the dental material may be the same as in the case of the dental monomer composition according to the first aspect of the invention.

[Method for Producing Dental Material]

A known method may be adopted without limitation as a method for producing the dental material according to the first aspect of the invention by mixing the dental polyfunctional monomer according to the first aspect of the invention, the polymerizable monomer other than the polyfunctional monomers (for example the (meth)acrylate group-containing monomer other than the polyfunctional monomers of the invention, or the epoxy group-containing monomer), the polymerization initiator, the filler, other components and the like.

[Cured Product]

The dental material according to the first aspect of the invention may be cured under appropriate conditions in accordance with the manner in which the polymerization initiator initiates the polymerization. In the case where, for example, the dental material according to the first aspect of the invention contains a visible light photopolymerization initiator, a desired cured product may be obtained by shaping the dental material into a prescribed form, and then irradiating the material with visible light for a prescribed time using a known irradiator. The conditions such as intensity may be controlled appropriately in accordance with the curability of the dental material. The cured product that has been cured by the application of light such as visible light may be heat treated under more appropriate conditions, and thereby the mechanical properties of the cured product can be enhanced. Alternatively, in the case where the dental material according to the first aspect of the invention contains a heat polymerization initiator, a desired cured product may be obtained by shaping the dental material into a prescribed form, and then heating the material at an appropriate temperature for an appropriate time.

The thus-obtained cured product of the dental material according to the first aspect of the invention may be used for dental treatment purposes.

[Usage]

The dental material according to the first aspect of the invention may be used by any known methods generally adopted for dental materials without limitation. When, for example, the dental material according to the first aspect of the invention is used as a composite resin for filling carious cavities, the purpose may be fulfilled by filling a cavity in the mouth with the dental material and photocuring the material using a known irradiator. When used as a composite resin for restoring a tooth crown, the material may be shaped into an appropriate form, then photocured with a known irradiator, and, if necessary, heat treated under prescribed conditions to give a desired material for restoring a tooth crown.

[Purposes]

The dental material according to the first aspect of the invention may be suitably used for dental treatment purposes, and may be used as, for example, a filling composite resin, a tooth crowning hard resin, a denture base resin, a denture base liner, an impression material, a dental adhesive material (orthodontic adhesive material, bonding material (which may be a more general expression), adhesive resin cement, filling adhesive composite resin or resin glass ionomer cement), a dental primer, a dental fissure sealant, a CAD/CAM resin block, a temporary crown or an artificial dental material.

[Kits]

Kits according to the first aspect of the invention include the dental material according to the first aspect. The kits according to the first aspect of the invention include kits in which each component of the dental material is packed as one agent; and kits composed of a plurality of agents such that each component of the dental material is divided into two or more agents and packed in view of a polymerization type, storage stability and the like. Such kits may include other dental materials which are used in combination with the dental material according to the first aspect of the invention.

[Dental Hydroxyl Group-Containing Monomer]

The dental hydroxyl group-containing monomer according to the second aspect of the invention is a compound represented by the general formula (8B) below, in which the core (X) below and the terminal group (Y2B) below are bonded to each other directly or via the linking group (Z) below.

[Chem. 51]

$$X(Y2B)n^{8aB}(Z-Y2B)n^{8bB} \qquad (8B)$$

In the general formula (8B), $n^{8aB}$ represents the number of terminal groups (Y2B) directly bonded to the core (X), $n^{8bB}$ represents the number of terminal groups (Y2B) bonded to the core (X) via the linking group (Z), and the sum of $n^{8aB}$ and $n^{8bB}$ is equal to the valence of the core (X). The combination of $n^{8aB}$ and $n^{8bB}$ is not limited as long as each of $n^{8aB}$ and $n^{8bB}$ is an integer of not less than 0 and the sum thereof is not less than 3. As an example of the combination, $n^{8aB}$ is 0 and $n^{8bB}$ is an integer of not less than 3, and in this case, all the terminal groups (Y2B) are bonded to the core X via the linking group (Z). As another example of the combination, $n^{8bB}$ is 0 and $n^{8aB}$ is an integer of not less than 3, and in this case, all the terminal groups (Y2B) are directly bonded to the core X.

[Core (X)]

The core (X) is a polyvalent organic group having a valence of not less than 3 containing an oxygen atom or a nitrogen atom in which an atom bonded to the terminal group (Y2B) or the linking group (Z) is the oxygen atom or the nitrogen atom. The oxygen atom or nitrogen atom bonded to the terminal group (Y2B) or the linking group (Z) is bonded to a methylene group or a divalent aromatic carbon group in addition to the terminal group (Y2B) or the linking group (Z). Any hydrogen atom present in the methylene group or the divalent aromatic carbon group may be substituted by a $C_{1-12}$ monovalent hydrocarbon group. The number of carbon atoms in the core (X) is usually in the range of 1 to 200, preferably 1 to 100, more preferably 1 to 30, still more preferably 2 to 20.

The valence of the core (X) is not less than 3 as described above, and preferably 3 to 12, more preferably 3 to 8. The atom bonded to the terminal group (Y2B) or the linking group (Z) is selected from an oxygen atom and a nitrogen atom as described above, and is preferably an oxygen atom. Examples of the core (X) include the groups represented by the general formulas (6a) to (6j) which are shown above as the cores (X) of the dental polyfunctional monomers.

[Terminal Group (Y2B)]

The terminal group (Y2B) is a (meth)acryloyl group-containing group (Y3) represented by the general formula (9) which is shown as the (meth)acryloyl group-containing group (Y3) present in the dental polyfunctional monomer, a (meth)acryloyl group or a $C_{1-20}$ hydrocarbon group, and a plurality of terminal groups (Y2B) may be the same as or different from each other, with the proviso that among all the terminal groups (Y2B) in the compound represented by the general formula (8B), one or more terminal groups are (meth)acryloyl group-containing groups (Y3), and one or more terminal groups are hydrogen atoms.

Examples of the (meth)acryloyl group-containing group (Y3) represented by the general formula (9) include the groups represented by the general formulas (9a) to (9f) which are shown above as specific examples of the (meth) acryloyl group-containing group (Y3) present in the dental polyfunctional monomer.

The terminal group (Y2B) is a (meth)acryloyl group-containing group (Y3) represented by the general formula (9), a (meth)acryloyl group or a $C_{1-20}$ hydrocarbon group as described above, and preferably a (meth)acryloyl group-containing group (Y3) or a hydrogen atom.

[Linking Group (Z)]

The linking group (Z) is the same as a divalent group represented by the general formula (2) which is shown as the linking group (Z) present in the dental polyfunctional monomer, and when the compound represented by the general formula (8B) contains a plurality of linking groups (Z), the linking groups (Z) may be the same as or different from each other.

The definitions and preferred aspects of $n^{2a}$, $n^{2b}$, $n^{2c}$ and $n^{2d}$ in the general formula (2) are the same as in the case of the dental polyfunctional monomer. In the dental hydroxyl group-containing monomer, the left end of the group represented by the general formula (2) is bonded to the core (X), and the right end of the group is bonded to the terminal group (Y2B).

The descriptions of the repeating units represented by —$C_2H_4O$—, —$C_3H_6O$—, —$C_4H_8O$— and —CO(CH$_2$)$_5$O— in the general formula (2) are the same as in the case of the dental polyfunctional monomer.

The linking group (Z) is preferably a divalent group represented by the general formula (4) which is shown above as a preferred example of the linking group (Z) present in the dental polyfunctional monomer. When the compound represented by the general formula (8B) contains a plurality of linking groups (Z), the linking groups (Z) may be the same as or different from each other.

The definitions and preferred aspects of $n^{4a}$, $n^{4b}$ and $n^{4c}$ in the general formula (4) are the same as in the case of the dental polyfunctional monomer. In the dental hydroxyl group-containing monomer, the left end of the group represented by the general formula (2) is bonded to the core (X), and the right end of the group is bonded to the terminal group (Y2B). The descriptions of the repeating units in the general formula (4) are the same as the descriptions of the repeating units in the general formula (2).

The linking group (Z) is more preferably a divalent group represented by the general formula (5) which is shown above as a preferred example of the linking group (Z) present in the dental polyfunctional monomer. When the compound represented by the general formula (8B) contains a plurality of linking groups (Z), the linking groups (Z) may be the same as or different from each other.

The definitions and preferred aspects of $n^{5a}$ and $n^{5b}$ in the general formula (5) are the same as in the case of the dental polyfunctional monomer. In the dental hydroxyl group-containing monomer, the left end of the group represented by the general formula (2) is bonded to the core (X), and the right end of the group is bonded to the terminal group (Y2B). The descriptions of the repeating units in the general formula (5) are the same as the descriptions of the repeating units in the general formula (2).

More specific examples of the linking group (Z) may include linking groups having repeating units composed of only oxyethylene units (linking groups in which $n^{5b}$ is 0, and $n^{5a}$ is 1 to 100, preferably 1 to 20 in the general formula (5)), linking groups having repeating units composed of only oxypropylene units (linking groups in which $n^{5a}$ is 0, and $n^{5b}$ is 1 to 100, preferably 1 to 20 in the general formula (5)), and linking groups having a block structure of polymer block composed of oxypropylene units/polymer block composed of oxyethylene units/polymer block composed of oxypropylene units (linking groups having a structure in which blocks are linked in the structure (5') below in the general formula (5)).

[Chem. 52]

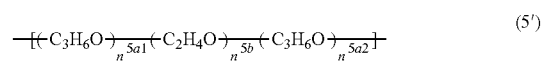

(5')

In the general formula (5'), $n^{5a1}$, $n^{5a2}$ and $n^{5b}$ represent the unit numbers of respective repeating units, and are each 1 to 100, preferably 1 to 20. The sum of $n^{5a1}$, $n^{5a2}$ and $n^{5b}$ is 1 to 100, preferably 1 to 20. The left end of the group is bonded to the core (X), the right end of the group is bonded to the terminal group (Y2B), and the oxypropylene polymer blocks and the oxyethylene polymer block in the bracket are bonded in the order presented. The descriptions of the repeating units in the general formula (5') are the same as the descriptions of the repeating units in the general formula (2).

[Method for Producing Dental Hydroxyl Group-Containing Monomer]

The dental polyfunctional monomer of the invention is obtained by, for example, reacting at least one of active protons in a compound represented by the general formula (1B) below, in which the core (X) below and the terminal group (Y1B) below are bonded to each other directly or via the linking group (Z) below, with isocyanate groups in a (meth)acryloyl group-containing isocyanate compound represented by the general formula (3) below to form corresponding carbamate groups or urea groups. It is to be noted that at least one of the active protons remains unreacted. The active proton mentioned here is a hydrogen atom which is bonded to alcoholic oxygen and amine nitrogen and which has reactivity with isocyanate at a practical rate.

The condition for production of the dental polyfunctional monomer of the invention is, for example, reaction of a raw material containing a compound represented by the general formula (1B) below, in which the core (X) below and the terminal group (Y1B) below are bonded to each other directly or via the linking group (Z) below, with a raw material containing a (meth)acryloyl group-containing isocyanate compound represented by the general formula (3) below, at a ratio of (the number of isocyanate groups present in the compound represented by the general formula (3) below)/(the number of active protons bonded to oxygen atoms and nitrogen atoms present in the compound represented by the general formula (1B) below) (hereinafter, written as a reaction ratio during production)<1. Here, the reaction ratio during production is preferably equal to or greater than 1/(the number of active protons bonded to oxygen atoms and nitrogen atoms present in the compound represented by the general formula (1B) below (the average number of active protons per molecule of the compound (1B))). Here, in terms of a stoichiometric ratio, some of active protons in the compound represented by the general formula (1B) below remain in the reaction product.

The number of moles of active protons in a raw material containing the compound represented by the general formula (1B) below can be determined by calculation on the basis of a known analysis method, for example measurement of a hydroxyl group value, specifically JIS K 0070-1992, JIS K 1557-1-2007, ISO 14900-2001, a method conforming thereto, or the like. Further, the number of moles of isocyanate groups present in the compound represented by the general formula (3) below can be determined by calculation on the basis of a known analysis method, for example measurement of a NCO value, specifically JIS K 7301-1995, JIS K 1603-2007, JIS K 1556-2006, ISO 14896-2006, a method conforming thereto, or the like.

[Chem. 53]

$$X(Y1B)n^{1aB}(Z-Y1B)n^{1bB} \quad (1B)$$

In the general formula (1B), $n^{1aB}$ represents the number of terminal groups (Y1B) directly bonded to the core (X), $n^{1bB}$ represents the number of terminal groups (Y1B) bonded to the core (X) via the linking group (Z), and the sum of $n^{1aB}$ and $n^{1bB}$ is equal to the valence of the core (X). The combination of $n^{1aB}$ and $n^{1bB}$ is not limited as long as each of $n^{1aB}$ and $n^{1bB}$ is an integer of not less than 0 and the sum thereof is not less than 3. As an example of the combination, $n^{1aB}$ is 0 and $n^{1bB}$ is an integer of not less than 3, and in this case, all the terminal groups (Y1B) are bonded to the core X via the linking group (Z). As another example of the combination, $n^{1bB}$ is 0 and $n^{1aB}$ is an integer of not less than 3, and in this case, all the terminal groups (Y2B) are directly bonded to the core X. The core (X) and the linking group (Z) are as described for the general formula (8B)

[Terminal Group (Y1B)]

The terminal group (Y1B) is a (meth)acryloyl group, a $C_{1-20}$ monovalent hydrocarbon group or a hydrogen atom, and a plurality of terminal groups (Y1B) may be the same as or different from each other, with the proviso that among terminal groups (Y1B) present in the compound represented by the general formula (1B), two or more terminal groups are hydrogen atoms. The terminal group (Y1B) is preferably a (meth)acryloyl group or a hydrogen atom, and is more preferably composed of only a hydrogen atom.

Specific Examples of Compounds of General Formula (1B)

Examples of the compounds of the general formula (1B) include polyhydric alcohols represented by the general formulas (6'a) to (6'h) which are shown as specific examples of the compounds of the general formula (1A) for use in production of the dental polyfunctional monomer.

The definition and preferred examples of $n^{6'g}$ in the general formula (6'g) are the same as in the case of the compounds of the general formula (1A).

Among the compounds of the general formula (1B), other compounds are polyols represented by the general formulas (6'i) to (6'k) which are shown as specific examples of the compounds of the general formula (1A) for use in production of the dental polyfunctional monomer.

The definitions and preferred aspects of $n^{6'i-a}$, $n^{6'j-a}$ and $n^{6'k-a}$ in the general formulas (6'i), (6'j) and (6'k), the definitions and preferred aspects of $n^{6'i-b}$ and $n^{6'j-b}$ in the general formulas (6'i) and (6'j), the definitions and preferred aspects of $n^{6'k-b}$ and $n^{6'k-c}$ in the general formula (6'k), and the definitions and specific examples of X in the general formulas (6'i), (6'j) and (6'k) are the same as in the case of the compounds of the general formula (1A) for use in production of the dental polyfunctional monomer.

Some of the polyols having repeating units such as oxyethylene units and oxypropylene units in the molecule have been already widely used in the industrial world as materials for polyurethane and the like. While the method for producing the polyols is not particularly limited, these polyols are obtained by adding ethylene oxide, propylene oxide or the like to polyols represented by the general formulas (6'a) to (6'h) using a known method.

[(Meth)Acryloyl Group-Containing Isocyanate Compound]

[Chem. 54]

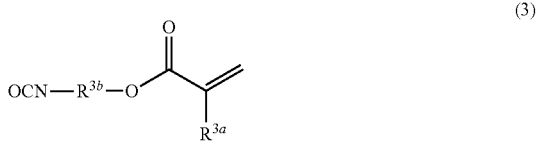

(3)

In the general formula (3), $R^{3a}$ represents a hydrogen atom or a methyl group, $R^{3b}$ represents a $C_{2-6}$ linear alkylene group or a $C_{2-6}$ linear oxyalkylene group, and the linear alkylene group or the linear oxyalkylene group is optionally substituted with a $C_{1-6}$ alkyl group or a (meth)acryloyloxymethylene group in place of a hydrogen atom.

Specific examples of the (meth)acryloyl group-containing isocyanate compounds represented by the general formula (3) may include at least one selected from the group consisting of compounds represented by general formulas (3a) to (3f) which are shown as preferred examples of the compounds represented by the general formula (3) for use in production of the dental polyfunctional monomer.

These (meth)acryloyl group-containing isocyanate compounds may be used singly, or two or more thereof may be used in combination.

[Reaction Conditions]

As described above, the dental hydroxyl group-containing monomer of the invention is obtained by reacting a compound represented by the general formula (1B) with a (meth)acryloyl group-containing isocyanate compound represented by the general formula (3). The reaction can be carried out by a known method or a substantially known method.

The dental hydroxyl group-containing monomer of the invention can be obtained by, for example, mixing a compound represented by the general formula (1B) with a (meth)acryloyl group-containing isocyanate compound represented by the general formula (3). During this process, the hydroxyl groups or the amino groups in the compound represented by the general formula (1B) react with the isocyanate groups in the (meth)acryloyl group-containing isocyanate compound represented by the general formula (3) to form carbamoyl groups or urea groups. This reaction is sometimes called the urethane-forming reaction.

The reaction may be carried out in the presence or absence of a catalyst. To enhance the reaction rate, a catalyst is preferably added. Known catalysts capable of accelerating the urethane-forming reaction may be used as the catalysts.

Specific examples of the urethane-forming catalyst are the same as in the case of production of the dental polyfunctional monomer. Of these, dibutyltin dilaurate and tin octanoate are advantageous in that the reaction is facilitated with a small amount of the catalyst and the catalyst has high selectivity for diisocyanate compounds.

When the urethane-forming catalyst is used, the amount thereof is preferably 0.001 to 0.5 parts by weight, more preferably 0.002 to 0.3 parts by weight, still more preferably 0.01 to 0.3 parts by weight, further preferably 0.01 to 0.2 parts by weight, still further preferably 0.05 to 0.2 parts by weight per 100 parts by weight in total of the compound represented by the general formula (1B) and the (meth)acryloyl group-containing isocyanate compound represented by the general formula (3). If the amount is below the lower limit, the catalytic effect is decreased to give rise to a risk that a significantly long reaction time is incurred. If the amount is above the upper limit, the catalytic effect is so increased that the reaction generates a large amount of heat possibly to make it difficult to control the temperature. The catalyst may be added in the whole amount at the initiation of the reaction, or may be added successively or in portions to the reaction system as required. Such successive or portionwise addition of the catalyst prevents the generation of an excessively large amount of reaction heat at the initial stage of the reaction and thus facilitates the control of the reaction temperature.

The reaction temperature is not particularly limited, but is preferably 0 to 120° C., more preferably 20 to 100° C., and still more preferably 40 to 80° C. At a reaction temperature below the lower limit, the reaction rate is markedly decreased and the reaction requires a very long time to complete or does not complete at times. On the other hand, the reaction at a temperature above the upper limit may involve side reactions generating impurities. Such impurities may cause the coloration of the dental hydroxyl group-containing monomer produced.

To ensure stable production at the aforementioned preferred range of temperatures, it is preferable that the reaction temperature be controlled. The urethane-forming reaction is usually exothermic. In the case where the reaction generates a large amount of heat and the temperature of the reaction product may be elevated above the preferred range of the reaction temperature, cooling is sometimes performed. When the reaction has substantially completed and the temperature of the reaction product may be decreased below the preferred range of the reaction temperature, heating is sometimes performed.

The dental hydroxyl group-containing monomer of the invention has polymerization activity. Thus, undesired polymerization reaction may take place when the system is subjected to a high temperature during the production of the monomer. To prevent such undesired polymerization reaction, a known polymerization inhibitor may be added before the initiation of the reaction or during the reaction. The polymerization inhibitor is not particularly limited as long as the inhibitor can suppress undesired polymerization of (meth)acryloyl groups in production of the dental hydroxyl group-containing monomer of the invention, and specific examples and preferred examples thereof are the same as in the case of production of the dental polyfunctional monomer. The amount of the polymerization inhibitor added is not particularly limited, but is preferably 0.001 to 0.5 parts by weight, more preferably 0.002 to 0.3 parts by weight, still more preferably 0.005 to 0.3 parts by weight, further preferably 0.005 to 0.1 parts by weight, still further preferably 0.01 to 0.1 parts by weight per 100 parts by weight in total of the compound represented by the general formula (1B) and the (meth)acryloyl group-containing isocyanate compound represented by the general formula (3). If the amount is below the lower limit, the polymerization inhibitor may fail to perform as expected. If the amount is above the upper limit, a dental material containing such a dental hydroxyl group-containing monomer may exhibit a markedly low curing rate and may have a limited practical applicability.

The urethane-forming reaction may involve a solvent. The solvent is not particularly limited as long as the solvent does not have practical reactivity with the compound represented by the general formula (1B) and the (meth)acryloyl group-containing isocyanate compound represented by the general formula (3), does not inhibit the reaction, and can dissolve the raw materials and the product. The reaction may be performed in the absence of solvents. The (meth)acryloyl group-containing isocyanate compound represented by the general formula (3) is usually a low viscous liquid and is miscible with the compound represented by the general formula (1B) to allow the reaction to take place without solvents.

The compound represented by the general formula (1B) and the (meth)acryloyl group-containing isocyanate compound represented by the general formula (3) may be mixed with each other by any methods without limitation. For example, a controlled amount of the (meth)acryloyl group-containing isocyanate compound represented by the general formula (3) may be admixed with the compound represented by the general formula (1B) placed in a reaction vessel; a controlled amount of the compound represented by the general formula (1B) may be admixed with the (meth)acryloyl group-containing isocyanate compound represented by the general formula (3) placed in a reaction vessel; or controlled amounts of the compound represented by the general formula (1B) and the (meth)acryloyl group-containing isocyanate compound represented by the general formula (3) may be added to a reaction vessel at the same time and mixed with each other. By these mixing methods, the amount of heat generated by the urethane-forming reaction can be controlled in an appropriate range and thus the temperature control during the reaction is facilitated. Alternatively, the urethane-forming reaction may be performed in such a manner that the whole amounts of the compound represented by the general formula (1B) and the (meth)acryloyl group-containing isocyanate compound represented by the general formula (3) are added to a reaction vessel and thereafter the temperature is increased. During the reaction, the reaction temperature may be sharply increased due to the generation of reaction heat and the temperature control by cooling may be appropriately required at times.

Oxygen is effective as a polymerization inhibitor for compounds containing (meth)acryloyl groups. Thus, oxygen is sometimes introduced into the reactor to prevent undesired polymerization of (meth)acryloyl groups during the reaction. Specific aspects and preferred aspects of introduction of oxygen are the same as in the case of production of the dental polyfunctional monomer.

If water is present as an impurity in the system during the urethane-forming reaction, the (meth)acryloyl group-containing isocyanate compound represented by the general formula (3) and the water may react with each other, resulting in formation of unintended impurities. Thus, it is preferable that as little water as possible be present in the reaction system during the urethane-forming reaction.

Therefore, the amount of water present in the compound represented by the general formula (1B) is preferably as small as possible. Specifically, the amount of water is preferably not more than 0.5 wt %, more preferably not more than 0.3 wt %, still more preferably not more than 0.1 wt % based on the amount of the compound represented by the general formula (1B). In the case where the compound represented by the general formula (1B) contains water in an amount exceeding the upper limit, it is preferable that the compound be used as a raw material for the dental hydroxyl group-containing monomer of the invention after water is removed therefrom by a known method. The reaction vessel in which the urethane-forming reaction will be performed is preferably dried by a known method to remove water therefrom.

[Dental Monomer Composition Containing Dental Hydroxyl Group-Containing Monomer]

The dental hydroxyl group-containing monomer according to the second aspect of the invention can be blended with other components, for example components other than the hydroxyl group-containing monomers and suitable for dental materials, to form a dental monomer composition. The dental monomer composition may contain a polymerizable monomer other than the dental hydroxyl group-containing monomers according to the second aspect of the invention and capable of being blended with the later-described dental materials (for example a (meth)acrylate group-containing monomer other than the hydroxyl group-containing monomers of the invention).

In the dental monomer composition according to the second aspect of the invention, for example, the content of the dental hydroxyl group-containing monomer according to the second aspect of the invention may be not less than 1.0 mass % (e.g. not less than 10 mass %, not less than 50 mass %, not less than 80 mass % or not less than 90 mass %) and may be not more than 100 mass % (e.g. not more than 99 mass %, not more than 90 mass %, not more than 80 mass %, not more than 50 mass % or not more than 10 mass %) based on the total amount of the dental monomer composition.

The dental monomer composition according to the second aspect of the invention is preferably negative in a reverse mutation test. The reverse mutation test (Ames test) is conducted in accordance with the same procedure as that of the above-described reverse mutation test of the dental monomer composition according to the first aspect of the invention except that the dental monomer composition according to the second aspect of the invention is used in place of the dental monomer composition according to the first aspect of the invention.

(Cell Test in NRU Method)

The dental monomer composition according to the second aspect of the invention may allow the relative cell survival rate to fall within a certain range in a cell test in the NRU method using Balb/3T3 cells. The cell test is conducted in accordance with the same procedure as that of the above-described cell test in the NRU method except that the dental monomer composition according to the second aspect of the invention is used in place of the dental monomer composition according to the first aspect of the invention. Further, the concentration of the test substance of the test composition (the dental hydroxyl group-containing monomer of the dental monomer composition) in the test solution, and the relative cell growth rate (%) in the dental monomer composition may be the same as in the case of the dental monomer composition according to the first aspect of the invention.

(Cell Test in WST Method)

The dental material of the polyfunctional monomer according to the first aspect of the invention may allow the relative cell growth rate to fall within a certain range in a cell test in the WST method using Balb/3T3 cells. The cell test is conducted in accordance with the same procedure as that of the above-described cell test in the WST method except that the dental monomer composition according to the second aspect of the invention is used in place of the dental monomer composition according to the first aspect of the invention. Further, the concentration of the test substance of the test composition (the dental hydroxyl group-containing monomer of the dental monomer composition) in the test solution, and the relative cell growth rate (%) in the dental monomer composition may be the same as in the case of the dental monomer composition according to the first aspect of the invention.

[Dental Material Containing Dental Hydroxyl Group-Containing Monomer]

The dental hydroxyl group-containing monomer according to the second aspect of the invention is suitable as a raw material for dental materials. By blending the dental hydroxyl group-containing monomer of the invention with components other than the dental hydroxyl group-containing monomers of the invention (for example polymerizable monomers other than the dental hydroxyl group-containing monomers ((meth)acrylate group-containing monomers other than the hydroxyl group-containing monomers of the invention, monomers containing epoxy groups, and the like)), a dental material containing the dental hydroxyl group-containing monomer of the invention can be produced.

[(Meth)Acrylate Group-Containing Monomers Other than Inventive Dental Hydroxyl Group-Containing Monomers]

Examples of the components other than the dental hydroxyl group-containing monomers of the invention may include (meth)acrylate group-containing monomers other than the hydroxyl group-containing monomers of the invention.

The (meth)acrylate group-containing monomer other than the hydroxyl group-containing monomers of the invention contains one or more (meth)acrylate groups in the molecule. The number of polymerizable groups present may be 1, or not less than 2.

The (meth)acrylate group-containing monomer other than the hydroxyl group-containing monomers of the invention may be composed of one compound, or composed of a mixture of two or more compounds.

Examples of the (meth)acrylate group-containing monomers other than the hydroxyl group-containing monomers, which have only one polymerizable group, include monomers represented by the general formula (21) which are shown above as monomers which can be used in combination with the dental polyfunctional monomer (of the monomers represented by the general formula (21), monomers corresponding to the dental hydroxyl group-containing monomers of the invention are excluded).

Specific examples of the monovalent organic groups which can be present as $R^{21b}$ in the general formula (21) are the same as in the case of the monomers represented by the general formula (21) which can be used in combination with the dental polyfunctional monomer.

Specific examples of the methacryloyl group-containing compounds represented by the general formula (21) are the same as in the case of the monomers represented by the general formula (21) which can be used in combination with the dental polyfunctional monomer.

Specific examples of the acryloyl group-containing compounds represented by the general formula (21) are the same as in the case of the monomers represented by the general formula (21) which can be used in combination with the dental polyfunctional monomer.

Examples of the (meth)acrylate group-containing monomers other than the hydroxyl group-containing monomers of the invention, which have two or more polymerizable groups, include monomers represented by the general formula (22) which are shown above as (meth)acrylate group-containing monomers other than the dental polyfunctional monomers, which can be used in combination with the dental polyfunctional monomer (of the monomers represented by the general formula (22), monomers corresponding to the dental hydroxyl group-containing monomers of the invention are excluded).

Specific examples of the divalent organic groups which can be present as $R^{22c}$ in the general formula (22) are the same as in the case of the monomers represented by the general formula (22) which can be used in combination with the dental polyfunctional monomer.

Among the monomers represented by the general formula (22), some preferred monomers are those monomers in which $R^{22c}$ is a linear alkylene group having 2 to 20 carbon atoms, preferably 4 to 12 carbon atoms.

Specific examples of the methacryloyl group-containing compounds which are the preferred monomers are the same as in the case of the monomers represented by the general formula (22) which can be used in combination with the dental polyfunctional monomer.

Specific examples of the acryloyl group-containing compounds which are the preferred monomers are the same as in the case of the monomers represented by the general formula (22) which can be used in combination with the dental polyfunctional monomer.

Among the monomers represented by the general formula (22), other preferred monomers are those monomers in which $R^{22c}$ is a linear oxyalkylene group having 2 to 20 carbon atoms, preferably 4 to 12 carbon atoms.

Specific examples of the methacryloyl group-containing compounds which are the preferred monomers are the same as in the case of the monomers represented by the general formula (22) which can be used in combination with the dental polyfunctional monomer.

Specific examples of the acryloyl group-containing compounds which are the preferred monomers are the same as in the case of the monomers represented by the general formula (22) which can be used in combination with the dental polyfunctional monomer.

Among the monomers represented by the general formula (22), other preferred monomers may be carbamoyl group-containing monomers represented by the general formula (23) which are shown above as monomers which can be used in combination with the dental polyfunctional monomer.

Specific examples of the divalent organic groups which can be present as $R^{23c}$ and $R^{23d}$ in the general formula (23) are the same as in the case of the monomers represented by the general formula (23) which can be used in combination with the dental polyfunctional monomer.

Specific examples of the $C_{1-20}$ divalent organic groups which may be present as $R^{23e}$ in the general formula (23) and contain oxygen are the same as in the case of the monomers represented by the general formula (23) which can be used in combination with the dental polyfunctional monomer.

Specific examples of the acryloyl group-containing compounds represented by the general formula (23) are the same as in the case of the monomers represented by the general formula (23) which can be used in combination with the dental polyfunctional monomer.

Among the (meth)acryloyl group-containing compounds represented by the general formula (23), other preferred compounds are at least one selected from the group consisting of compounds represented by the general formulas (24a) to (24e) which can be used in combination with the dental polyfunctional monomer.

Among the monomers represented by the general formula (22), other preferred compounds may be monomers of the general formula (25) which can be used in combination with the dental polyfunctional monomer.

Specific examples of the $C_{1-20}$ divalent organic groups which may be present as $R^{25e}$ in the general formula (25) and contain oxygen are the same as in the case of the monomers represented by the general formula (25) which can be used in combination with the dental polyfunctional monomer.

Specific examples of the methacryloyl group-containing compounds represented by the general formula (25) are the same as in the case of the monomers of the general formula (25) which can be used in combination with the dental polyfunctional monomer.

Specific examples of the acryloyl group-containing compounds represented by the general formula (25) are the same as in the case of the monomers represented by the general formula (25) which can be used in combination with the dental polyfunctional monomer.

When the dental material containing the dental hydroxyl group-containing monomer of the invention is used in such an application as dental adhesives, it is preferable that the dental material contain, as a (meth)acrylate group-containing monomer other than the hydroxyl group-containing monomer of the invention, a monomer exhibiting a bonding function. Examples of such adhesive (meth)acrylate group-containing monomers other than the hydroxyl group-containing monomer of the invention include monomers having at least one polymerizable group selected from methacryloyl groups and acryloyl groups, and an acidic group. Examples of the acidic groups include phosphate residues, pyrophosphate residues, thiophosphate residues, carboxylate residues and sulfonate residues.

Specific examples of the monomers having methacryloyl groups and phosphate residues are the same as specific examples of the monomers which have methacryloyl groups and phosphate residues and which can be used in combination with the dental polyfunctional monomer.

Specific examples of the monomers having acryloyl groups and phosphate residues are the same as specific examples of the monomers which have acryloyl groups and phosphate residues and which can be used in combination with the dental polyfunctional monomer.

Examples of the monomers having a methacryloyl group and a pyrophosphate residue include di(2-methacryloyloxyethyl) pyrophosphate, and acid chlorides thereof.

Examples of the monomers having an acryloyl group and a pyrophosphate residue include di(2-acryloyloxyethyl) pyrophosphate, and acid chlorides thereof.

Examples of the monomers having a methacryloyl group and a thiophosphate residue include 2-methacryloyloxyethyl dihydrogen dithiophosphate, 10-methacryloyloxydecyl dihydrogen thiophosphate, and acid chlorides of these compounds.

Examples of the monomers having an acryloyl group and a thiophosphate residue include 2-acryloyloxyethyl dihydrogen dithiophosphate, 10-acryloyloxydecyl dihydrogen thiophosphate, and acid chlorides of these compounds.

Examples of the monomers having a methacryloyl group and a carboxylate residue include 4-methacryloyloxyethoxycarbonylphthalic acid, 5-methacryloylaminopentylcarboxylic acid, 11-methacryloyloxy-1,1-undecanedicarboxylic acid, and acid chlorides and acid anhydrides of these compounds.

Examples of the monomers having an acryloyl group and a carboxylate residue include 4-acryloyloxyethoxycarbonylphthalic acid, 5-acryloylaminopentylcarboxylic acid, 11-acryloyloxy-1,1-undecanedicarboxylic acid, and acid chlorides and acid anhydrides of these compounds.

Examples of the monomers having a methacryloyl group and a sulfonate residue include 2-sulfoethyl methacrylate and 2-methacrylamido-2-methylpropanesulfonic acid.

Examples of the monomers having an acryloyl group and a sulfonate residue include 2-sulfoethyl acrylate and 2-acrylamido-2-methylpropanesulfonic acid.

[Polymerization Initiators]

Among the components other than the dental hydroxyl group-containing monomers of the invention in the dental materials according to the second aspect of the invention, other components may be polymerization initiators. The specific examples, preferred examples and the like of the polymerization initiators are the same as those of the polymerization initiators which can be present in the dental materials according to the first aspect of the invention.

The polymerization initiators or the photopolymerization initiators may be used singly, or two or more thereof may be used in appropriate combination. The amount thereof is usually in the range of 0.01 to 20 parts by weight, preferably 0.1 to 5 parts by weight per 100 parts by weight of the dental material.

[Fillers]

Among the components other than the dental hydroxyl group-containing monomers of the invention in the dental materials according to the second aspect of the invention, other components may be fillers. The specific examples, preferred examples and the like of the fillers are the same as those of the fillers present in the dental materials according to the first aspect of the invention.

These fillers may be appropriately added according to the purpose of the dental material. These fillers are appropriately used singly, or two or more thereof are appropriately used in combination. The preferred range of the amount of the filler varies depending on the purpose of the dental material. For example, in the case where the dental material is used as a dental bonding material which is one of dental adhesives, the filler may be added in an amount of about 0.1 to 5 parts by weight per 100 parts by weight of the dental material in order to adjust the viscosity of the dental material. As another example, in the case where the dental material is used as a dental adhesive cement which is one of dental adhesives, the filler may be added in an amount of about 30 to 70 parts by weight per 100 parts by weight of the dental material in order to enhance the mechanical strength and adjust the viscosity. As still another example, in the case where the dental material is used as a dental adhesive composite resin which is one of dental adhesives, the filler may be added in an amount of about 50 to 90 parts by weight per 100 parts by weight of the dental material in order to enhance the mechanical strength and adjust the viscosity.

[Other Components]

The dental material according to the second aspect of the invention may appropriately contain components other than the dental hydroxyl group-containing monomers of the invention, the polymerizable monomer other than the hydroxyl group-containing monomers of the invention (for example the (meth)acrylate group-containing monomer other than the hydroxyl group-containing monomers of the invention, or the epoxy group-containing monomer), the polymerization initiator and the filler in accordance with the purpose. For example, the dental material may contain the aforementioned polymerization inhibitor for enhancing storage stability. To control the color tone, known colorants such as pigments and dyes may be added. Further, known reinforcing materials such as fibers may be added to increase the strength of cured products. In addition, solvents such as acetone, ethanol and water may be added.

[Ratio of Components]

The amount of the hydroxyl group-containing monomer according to the second aspect of the invention based on the amount of the dental material is not particularly limited, and is, for example, in the range of 0.1 to 99%. The preferred amount of the hydroxyl group-containing monomer may vary depending on the purpose of the dental material. For example, the hydroxyl group-containing monomer is added in an amount of 1 to 50 wt %, more preferably 1 to 40 wt %, still more preferably 3 to 30 wt % based on the amount of the polymerizable monomer components (the dental hydroxyl group-containing monomer and the polymerizable monomer other than the hydroxyl group-containing monomers (for example the (meth)acrylate group-containing monomer other than the hydroxyl group-containing monomers of the invention, or the epoxy group-containing monomer)). In particular, when the dental material is used as a dental adhesive material (bonding material) or a dental primer, the amount of the hydroxyl group-containing monomer is preferably 1 to 50 wt %, more preferably 1 to 40 wt % based on the amount of polymerizable monomer components. When the dental material is used as a dental adhesive material (adhesive resin cement or filling adhesive composite resin) or a dental fissure sealant, the amount of the hydroxyl group-containing monomer is preferably 1 to 50 wt %, more preferably 1 to 20 wt % based on the amount of polymerizable monomer components.

(Reverse Mutation Test)

The dental material of the dental hydroxyl group-containing monomer according to the second aspect of the invention is preferably negative in a reverse mutation test. The reverse mutation test (Ames test) is conducted in accordance with the same procedure as that of the above-described reverse mutation test except that the dental hydroxyl group-containing monomer according to the second aspect of the invention is used in place of the dental monomer composition according to the first aspect of the invention.

(Cell Test in NRU Method)

The dental material of the dental hydroxyl group-containing monomer according to the second aspect of the invention may allow the relative cell survival rate to fall within a certain range in a cell test in the NRU method using Balb/3T3 cells. The cell test is conducted in accordance with the same procedure as that of the above-described cell test in the NRU method except that the dental material of the dental hydroxyl group-containing monomer according to the second aspect of the invention is used in place of the dental monomer composition according to the first aspect of the invention. Further, the concentration of the test substance of the test material (the dental hydroxyl group-containing monomer of the dental material) in the test solution, and the relative cell growth rate (%) in the dental material may be the same as in the case of the dental monomer composition according to the first aspect of the invention.

(Cell Test in WST Method)

The dental material of the dental hydroxyl group-containing monomer according to the second aspect of the invention may allow the relative cell growth rate to fall within a certain range in a cell test in the WST method using Balb/3T3 cells. The cell test is conducted in accordance with the same procedure as that of the above-described cell test in the WST method except that the dental material of the dental hydroxyl group-containing monomer according to the second aspect of the invention is used in place of the dental monomer composition according to the first aspect of the invention. Further, the concentration of the test substance of the test material (the dental hydroxyl group-containing monomer of the dental material) in the test solution, and the relative cell growth rate (%) in the dental material may be the same as in the case of the dental monomer composition according to the first aspect of the invention.

[Method for Producing Dental Material]

A known method may be adopted without limitation as a method for producing the dental material according to the second aspect of the invention by mixing the dental hydroxyl group-containing monomer according to the second aspect of the invention, the polymerizable monomer other than the hydroxyl group-containing monomers (for example the (meth)acrylate group-containing monomer other than the hydroxyl group-containing monomers of the invention, or the epoxy group-containing monomer), the polymerization initiator, the filler, other components and the like.

[Cured Product]

The dental material according to the second aspect of the invention may be cured under appropriate conditions in accordance with the manner in which the polymerization initiator initiates the polymerization. In the case where, for example, the dental material according to the second aspect of the invention contains a visible light photopolymerization initiator, a desired cured product may be obtained by shaping the dental material into a prescribed form, and then irradiating the material with visible light for a prescribed time using a known irradiator. The conditions such as intensity may be controlled appropriately in accordance with the curability of the dental material. The cured product that has been cured by the application of light such as visible light may be heat treated under more appropriate conditions, and thereby the mechanical properties of the cured product can be enhanced. Alternatively, in the case where the dental material according to the second aspect of the invention contains a heat polymerization initiator, a desired cured product may be obtained by shaping the dental material into a prescribed form, and then heating the material at an appropriate temperature for an appropriate time.

The thus-obtained cured product of the dental material according to the second aspect of the invention may be used for dental treatment purposes.

[Purposes]

The dental material according to the second aspect of the invention may be suitably used for dental treatment purposes, and may be used as, for example, a filling composite resin, a tooth crowning hard resin, a denture base resin, a denture base liner, an impression material, a dental adhesive material (orthodontic adhesive material, bonding material, adhesive resin cement, filling adhesive composite resin or resin glass ionomer cement), a dental primer, a dental fissure sealant, a CAD/CAM resin block, a temporary crown or an artificial dental material. The dental hydroxyl group-containing monomer in the present invention has a function of enhancing the adhesive strength with the tooth during dental treatment, and therefore may be particularly suitably used for dental adhesive materials and dental primers.

While details of the reason why the dental material according to the second aspect of the present invention may be particularly suitably used for dental adhesive materials and dental primers are unknown, the dental hydroxyl group-containing monomer according to the second aspect of the present invention contains both hydroxyl groups and (meth)acryloyl groups in the molecule as described above, and are thus supposed to have both the functions of interaction with the tooth surface via hydroxyl groups and bonding to a resin matrix via (meth)acryloyl groups. Further, the dental hydroxyl group-containing monomer according to the second aspect of the present invention has a carbamate structure in the molecule. The carbamate structure is known to exhibit the effect of imparting high mechanical properties to a so-called urethane polymer due to the coagulation effect of the carbamate structure in the urethane polymer, and the carbamate structure present in the molecule of the dental hydroxyl group-containing monomer according to the second aspect of the present invention may also have a favorable effect on the strength of the cured dental material according to the second aspect of the invention. Generally, enhancement of the strength of an adhesive layer has a favorable effect on the bonding properties of the adhesive layer.

[Usage]

The dental material according to the second aspect of the invention may be used by any known methods generally adopted for dental materials without limitation. When, for example, the dental material according to the second aspect of the invention is used as a bonding material, the dental material is applied to a cavity in the mouth, then dried as necessary, and photocured with a known irradiator as necessary, and a filling composite resin is then packed.

When, for example, the dental material according to the second aspect of the invention is used as an adhesive resin cement, a tooth surface and a prosthesis bonded surface are treated with a primer as necessary, and the dental material according to the second aspect of the invention is then applied to the prosthesis, and the prosthesis is pressure-bonded at a prescribed site in the mouth.

When, for example, the dental material according to the second aspect of the invention is used as a tooth primer, the dental material is applied to a cavity in the mouth, then dried as necessary, and photocured with a known irradiator as necessary, and a prosthesis coated with an adhesive cement is pressure-bonded to the cavity.

When, for example, the dental material according to the second aspect of the invention is used as a filling adhesive composite resin, the dental material is directly packed in a cavity in the mouth, and then photocured with a known irradiator to achieve the purpose.

[Kits]

Kits according to the second aspect of the invention include the dental material according to the second aspect. The kits according to the second aspect of the invention include kits in which each component of the dental material is packed as one agent; and kits composed of a plurality of agents such that each component of the dental material is divided into two or more agents and packed in view of a polymerization type, storage stability and the like. The kits according to the invention may include other dental materials which are used in combination with the dental material according to the second aspect of the invention. Such kits are used for bonding materials, adhesive cements, primers, adhesive composite resins and the like.

EXAMPLES

The present invention will be described in further detail based on Examples hereinbelow without limiting the scope of the invention to such Examples.

Examples, Comparative Examples and so on of the first aspect of the present invention will be described hereinbelow.

Production Example 1A

A 100-milliliter four-necked flask equipped with a stirring blade, a thermometer and a reflux tube was loaded with 50.0 g of a polyol (OH group: 0.150 mol) of the structural formula shown in Table 1A below (ACTCOL (registered trademark), manufactured by Mitsui Chemicals, Inc., average molecular weight: 1000, hydroxyl group value: 168 mg KOH/g), 0.073 g (1000 ppm based on the total weight of reactants) of dibutyltin dilaurate (manufactured by Wako Pure Chemical Industries, Ltd.) and 0.073 g (1000 ppm based on the total weight of reactants) of 2,6-t-butyl-4-methylphenol (manufactured by Wako Pure Chemical Industries, Ltd.), and heated to 60° C. Subsequently, 23.3 g (0.150 mol) of 2-methacryloyloxyethyl isocyanate (KARENZ MOI (registered trademark), manufactured by Showa Denko K.K.) was added dropwise over a period of 10 minutes. Reaction was carried out for 5 hours at a reaction temperature of 75 to 85° C. The infrared absorption spectrum IR of the reaction product was measured (Spectrum Two, manufactured by PerkinElmer), and the result showed that the isocyanate-derived vibration at 2267 cm-1 disappeared. The reaction product was discharged from the reaction vessel to give 71.2 g of a product containing a urethane-methacrylic polyfunctional monomer 1A of the structural formula in Table 1A below. A part of the product was taken, the hydroxyl group value thereof was measured in accordance with JIS K 0070-1992, and the result showed that the hydroxyl group value was not more than 1 mg KOH/g.

Production Examples 2A to 5A

Except that polyols shown in Table 1A were used in place of the polyol described in Production Example 1A, the same synthesis operation as in Production Example 1A was carried out to give products containing polyfunctional monomers 2A to 5A of the structural formulas in Table 1A below.

Production Example 6A

Except that 2-acryloyloxyethyl isocyanate (KARENZ AOI (registered trademark), manufactured by Showa Denko K.K.) was used in place of the 2-methacryloyloxyethyl isocyanate described in Production Example 1A, the same synthesis operation as in Production Example 1A was carried out to give a product containing a polyfunctional monomer 6 of the structural formula in Table 1A below.

TABLE 1A

| | Dental polyfunctional monomers | Structural formula/average molecular weight of polyol raw material |
|---|---|---|
| Production Example 1A | Polyfunctionl monomer 1A 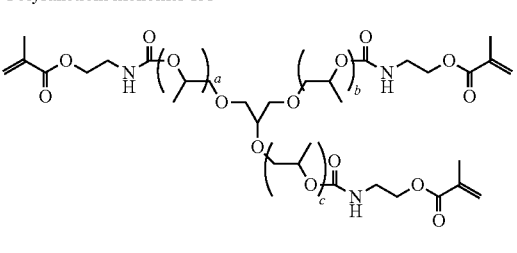 | 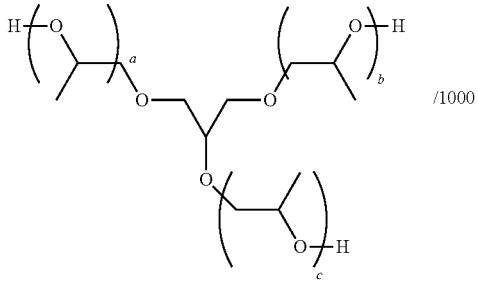 /1000 |
| Production Example 2A | Polyfunctionl monomer 2A 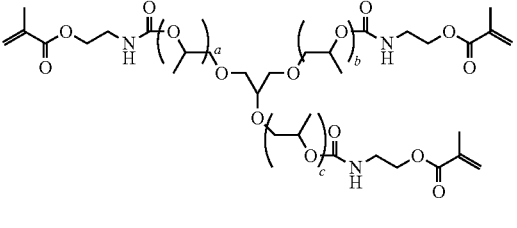 | 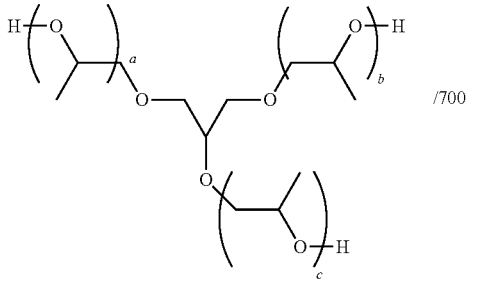 /700 |

TABLE 1A-continued

| Dental polyfunctional monomers | Structural formula/average molecular weight of polyol raw material |
|---|---|
| Production Example 3A — Polyfunctionl monomer 3A 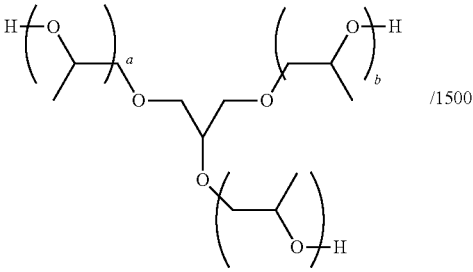 | 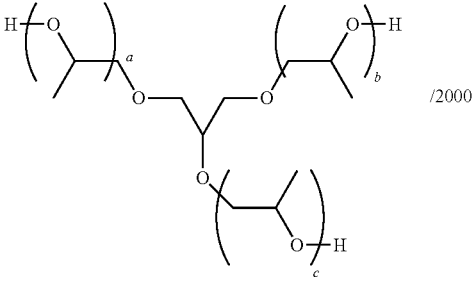 /1500 |
| Production Example 4A — Polyfunctionl monomer 4A | /2000 |
| Production Example 5A — Polyfunctionl monomer 5A | /500 |
| Production Example 6A — Polyfunctionl monomer 6A 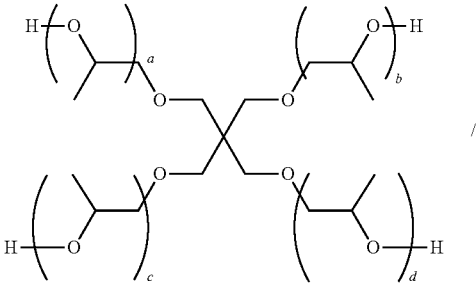 | 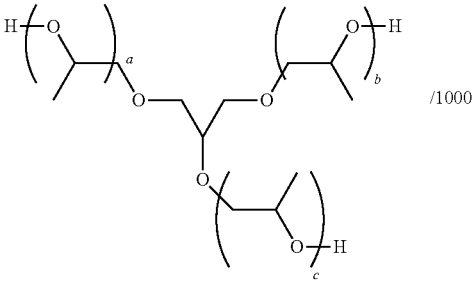 /1000 |

Example 1A-1

0.37 g of the polyfunctional monomer 1A obtained in Production Example 1A, 1.94 g of a urethane acrylate compound 7A of the structural formula below, and 0.12 g (0.42 mmol) of triethylene glycol dimethacrylate (NK Ester 3G, manufactured by Shin-Nakamura Chemical Co, Ltd. (hereinafter, abbreviated as TEGDMA)) were added into a container. The resulting mixture was stirred to uniformity at 50° C. to give a polymerizable monomer composition. 60 parts by weight of a barium aluminum borosilicate glass filler (GM 27884, particle diameter: 1.5 μm, 1.6% silane-treated product, manufactured by NEC SCHOTT Components Corporation) and 0.2 parts by weight of 2,4,6-trimethylbenzoyl-diphenyl-phosphine oxide (IRGACURE TPO, manufactured by BASF SE (hereinafter, abbreviated as TPO)) were then added to and mixed with 40 parts by weight of the polymerizable monomer composition to give a uniform pasty composition to be used as a dental material.

[Bending Strength Test Method]

The composition prepared as described above was packed in a 2×2×25 mm SUS mold, covered with a cover film, and then irradiated with light from a dental visible light irradiator (a Light V, manufactured by J. Morita Tokyo MFG. Corp.) for 3 minutes on each side, namely, for a total of 6 minutes on both sides to cure the composition. The cured product was stored in deionized water at 37° C. for 24 hours, and then subjected to a three-point bending test with a general-purpose tester (Precise Versatile Material Tester 210×, manufactured by INTESCO Co., Ltd.) under conditions in which the distance between supports was 20 mm and the cross head speed was 1 mm/min. The results of the bending test of the cured products of the compositions to be used as the dental materials are shown in Table 2A.

[Chem. 55]

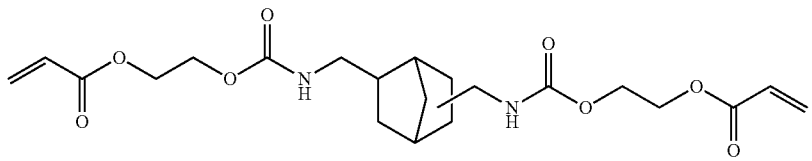

[Compound 7A]

[Compound 7A]

Example 1A-2

A composition to be used as a dental material was obtained by following the operation in Example 1A-1 except that the polyfunctional monomer 5A obtained in Production Example 5A was used in place of the polyfunctional monomer 1A. Further, the same operation as in Example 1A-1 was carried out to obtain bending test results. The results are shown in Table 2A.

Comparative Example 1A-1

A composition to be used as a dental material was obtained by following the operation in Example 1A-1 except that in place of the polyfunctional monomer 1A obtained in Production Example 1A, TEGDMA in an amount equal to that of the polyfunctional monomer 1A was used to increase the amount of TEGDMA. Further, the same operation as in Example 1A-1 was carried out to obtain bending test results. The results are shown in Table 2A.

Example 2A-1

A composition to be used as a dental material was obtained by following the operation in Example 1A-1 except that a urethane acrylate compound 8A was used in place of the urethane acrylate compound 7A. Further, the same operation as in Example 1A-1 was carried out to obtain bending test results. The results are shown in Table 2A.

[Chem. 56]

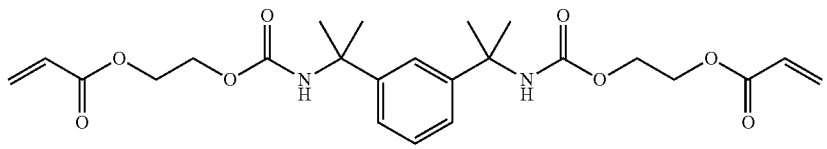

[Compound 8A]

[Compound 8A]

Comparative Example 2A-1

A composition to be used as a dental material was obtained by following the operation in Example 1A-3 except that in place of the polyfunctional monomer 1A obtained in Production Example 1A, TEGDMA in an amount equal to that of the polyfunctional monomer 1A was used to increase the amount of TEGDMA. Further, the same operation as in Example 1A-3 was carried out to obtain bending test results. The results are shown in Table 2A.

TABLE 2A

| | | Enhancement of toughness | | |
| --- | --- | --- | --- | --- |
| | | Bending test results of filler-containing composition cured products | | |
| | Monomer composition Monomer component weight ratio | Maximum stress (MPa) | Elastic modulus (GPa) | Fracture energy (mJ) |
| Example 1A-1 | Polyfunctional monomer 1A/TEGDMA/compound 7A 15/5/80 | 163 | 8.0 | 25 |

TABLE 2A-continued

Enhancement of toughness

| | Monomer composition Monomer component weight ratio | Bending test results of filler-containing composition cured products | | |
|---|---|---|---|---|
| | | Maximum stress (MPa) | Elastic modulus (GPa) | Fracture energy (mJ) |
| Example 1A-2 | Polyfunctional monomer 5A/TEGDMA/compound 7A 15/5/80 | 182 | 8.6 | 25 |
| Comparative Example 1A-1 | TEGDMA/compound 7A 20/80 | 124 | 8.3 | 10 |
| Example 2A-1 | Polyfunctional monomer 1A/TEGDMA/compound 8A 15/5/80 | 171 | 8.4 | 37 |
| Comparative Example 2A-1 | TEGDMA/compound 8A 20/80 | 142 | 9.7 | 13 |

The results in Table 2A show that the cured products from the compositions to be used as dental materials containing the dental polyfunctional monomers according to the first aspect of the invention achieved marked enhancement in flexural breaking strength and fracture energy as compared to the cured products of the conventional compositions. Thus, it has been indicated that use of the inventive dental polyfunctional monomers having both toughness and rigidity enhances the strength and toughness of the cured products of the dental materials.

Example 3A-1

0.5 parts by weight of TPO was added to 100 parts by weight of the polyfunctional monomer 1A obtained in Production Example 1A, and the resulting mixture was stirred to uniformity at room temperature to give a monomer solution. Thereafter, the resulting mixture was irradiated with light from a dental irradiator (Translux 2Wave, manufactured by Heraeus Kulzer GmbH) for 20 seconds, and the polymerization rate was measured by infrared spectroscopy (IR) (Spectrum Two, manufactured by PerkinElmer). The results are shown in Table 3.

The polymerization rate (%) was calculated from the following formula.

polymerization rate (%)={1-($I_{X,C-H}/I_{X,C=O}$)/($I_{0,C-H}/I_{0,C=O}$)}×100

$I_{X,C-H}$: absorbance at 810 cm-1 (acryloyl group-derived absorption) or 815 cm-1 (methacryloyl group-derived absorption) after photoirradiation
$I_{0,C-H}$: above absorbance before photoirradiation
$I_{X,C=O}$: absorbance at 1637 cm-1 (carbonyl group-derived absorption) after photoirradiation
$I_{0,C=O}$: above absorbance before photoirradiation Examples 3A-2 to 3A-5

The polymerization rates of the polyfunctional monomers 2A, 3A, 4A and 6A obtained in Production Examples were measured by the same method as in Example 3A-1. The results are shown in Table 3A.

Example 3A-1

The polymerization rate of the general-purpose dental mathacrylic compound TEGDMA is measured by the same method as in Example 3A-1. The result is shown in Table 3A.

TABLE 3A

| | Polymerizable monomers | Polymerization rate/% |
|---|---|---|
| Example 3A-1 | Polyfunctional monomer 1A | 98 |
| Example 3A-2 | Polyfunctional monomer 2A | 84 |
| Example 3A-3 | Polyfunctional monomer 3A | 99 |
| Example 3A-4 | Polyfunctional monomer 4A | 95 |
| Example 3A-5 | Polyfunctional monomer 6A | 97 |
| Comparative Example 3A-1 | TEGDMA | 28 |

Examples, Comparative Examples and so on of the second aspect of the present invention will be described hereinbelow.

Production Example 1B

A 300-milliliter four-necked flask equipped with a stirring blade, a thermometer and a reflux tube was loaded with 99.0 g of a polyol 1B (OH group: 1.63 mol) of the structural formula blow (ACTCOL (registered trademark), manufactured by Mitsui Chemicals, Inc., average molecular weight: 182, hydroxyl group value: 926 mg KOH/g), 0.27 g (1000 ppm based on the total weight of reactants) of dibutyltin dilaurate (manufactured by Tokyo Chemical Industry Co., Ltd.) and 0.14 g (500 ppm based on the total weight of reactants) of 2,6-t-butyl-4-methylphenol (manufactured by Tokyo Chemical Industry Co., Ltd.), and heated to 55° C. Subsequently, 171 g (1.10 mol, ⅔ equivalents based on the number of moles of OH of the polyol 1 used) of 2-methacryloyloxyethyl isocyanate (KARENZ MOI (registered trademark), manufactured by Showa Denko K.K.) was added dropwise over a period of 20 minutes. Reaction was carried out for 8 hours at a reaction temperature of 80 to 85° C. The infrared absorption spectrum IR was measured (Spectrum Two, manufactured by PerkinElmer), and the result showed that the isocyanate-derived vibration at 2267 cm-1 disappeared. A part of the product was taken, the hydroxyl group value thereof was measured in accordance with JIS K 0070, and the result showed that the hydroxyl group value was 119 mg KOH/g. The reaction product was subjected to liquid chromatography mass spectrometry (LC-MS analysis) (1.7 μm ACQUITY UPLC BEH C18 (2.1 mm×10 mm)/ACQUITY UPLC H-Class-SQ Detector 2, manufactured by Nihon Waters K.K.), and the result showed that the mass of [M-H]$^+$ was 489 and the mass of [M-Na]$^+$ was 511. This result demonstrated that the main product had a molecular weight of 488, and this molecular weight was consistent with that of the compound 1B in which one oxyethylene unit is introduced and a+b+c is equal to 1. The reaction product was discharged from the reaction vessel to give 260 g of a product containing a hydroxyl group-containing monomer represented by the structural formula of the compound 1B below.

[Chem. 57]

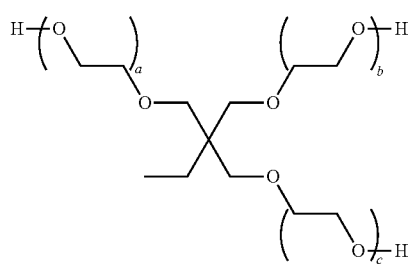

[Polyol 1B]

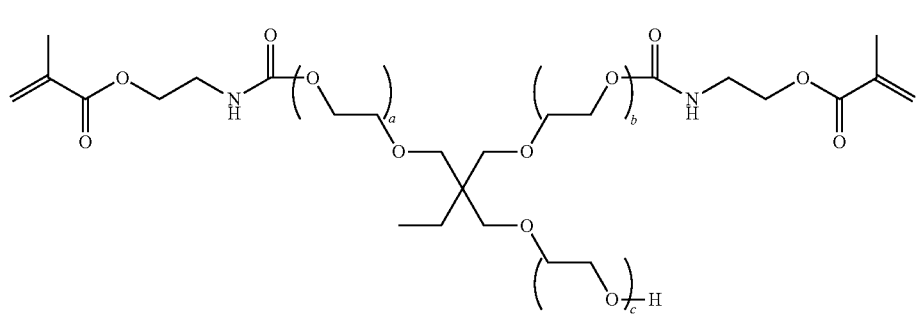

[Compound 1B]

Production Examples 2B to 5B

Except that polyols shown in Table 1B were used in place of the polyol described in Production Example 1B, the same synthesis operation as in Production Example 1B was carried out to give products containing hydroxyl group-containing monomers 2B to 5B.

Production Example 6B

Except that a polyol 6B shown in Table 1B was used in place of the polyol described in Production Example 1B, and ¾ equivalents of KARENZ MOI (registered trademark) was reacted based on the number of moles of OH of the polyol 6B, the same synthesis operation as in Production Example 1 was carried out to give a product containing a hydroxyl group-containing monomer 6B.

Production Example 7B

Except that a polyol 6B shown in Table 1B was used in place of the polyol described in Production Example 1B, and ¾ equivalents of KARENZ MOI-EG (registered trademark) was reacted based on the number of moles of OH of the polyol 6B, the same synthesis operation as in Production Example 1B was carried out to give a product containing a hydroxyl group-containing monomer 7B.

Production Example 8B

Except that a polyol 3B shown in Table 1B was used in place of the polyol described in Production Example 1B, and ⅔ equivalents of KARENZ MOI-EG (registered trademark) was reacted based on the number of moles of OH of the polyol 3B, the same synthesis operation as in Production Example 1B was carried out to give a product containing a hydroxyl group-containing monomer 8B.

Production Example 9B

Except that a polyol 6B shown in Table 1B was used in place of the polyol described in Production Example 1B, and ½ equivalents of KARENZ MOI (registered trademark) was reacted based on the number of moles of OH of the polyol 6B, the same synthesis operation as in Production Example 1B was carried out to give a product containing a hydroxyl group-containing monomer 9B.

TABLE 1B

| Production Example | Structural formula/average molecular weight/hydroxyl group value of polyol raw material (mgKOH/g) | Structural formula/hydroxyl group value of main product of hydroxyl group-containing monomer (mgKOH/g) |
|---|---|---|
| 1B | 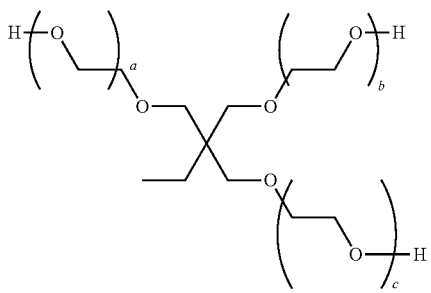<br>/182<br>/926<br>Polyol 1B | 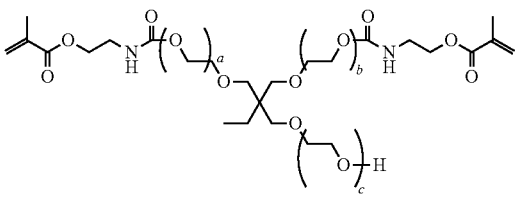<br>Compound 1B<br>/119 |
| 2B | 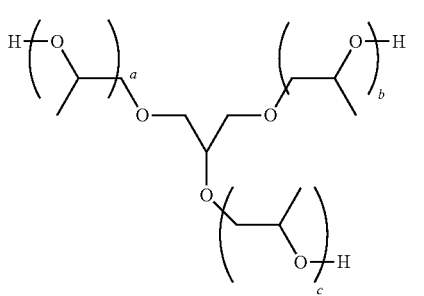<br>/1000<br>/168<br>Polyol 2B | 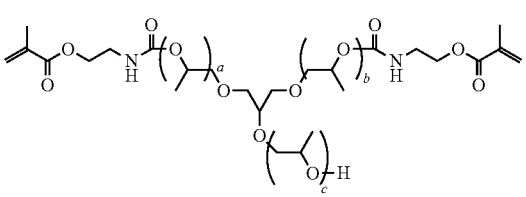<br>Compound 2B<br>/38 |
| 3B | 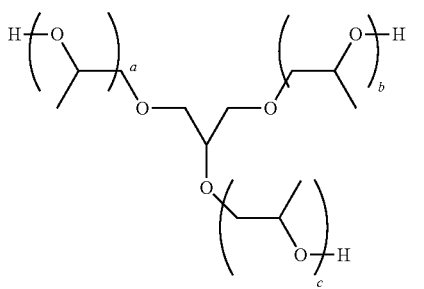<br>/700<br>/251<br>Polyol 3B | 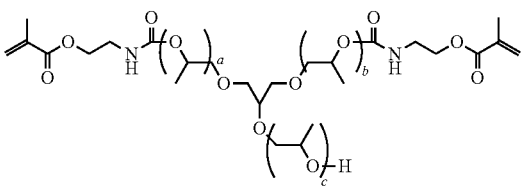<br>Compound 3B<br>/61 |
| 4B | 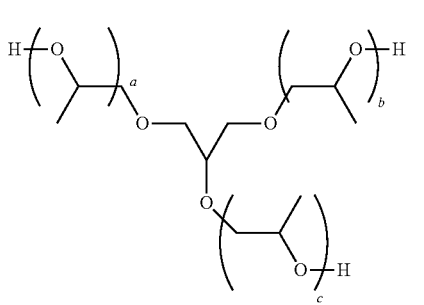<br>/250<br>/669<br>Polyol 4B | 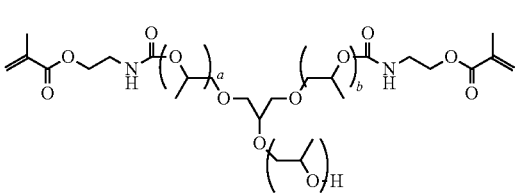<br>Compound 4B<br>/100 |

TABLE 1B-continued

| Production Example | Structural formula/average molecular weight/hydroxyl group value of polyol raw material (mgKOH/g) | Structural formula/hydroxyl group value of main product of hydroxyl group-containing monomer (mgKOH/g) |
|---|---|---|
| 5B | 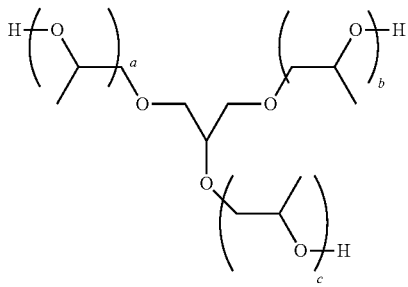<br>/400<br>/396<br>Polyol 5B | 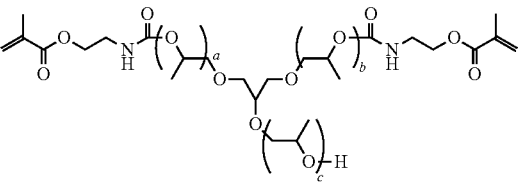<br>Compound 5B<br>/84 |
| 6B | 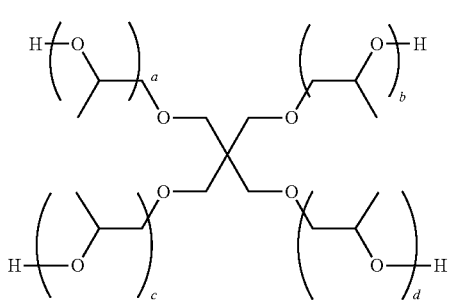<br>/500<br>/458<br>Polyol 6B | 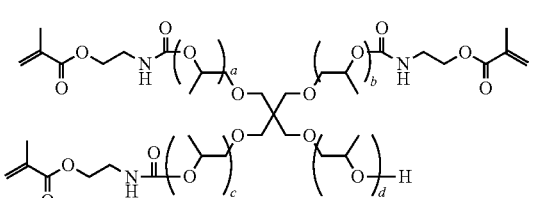<br>Compound 6B<br>/68 |
| 7B | 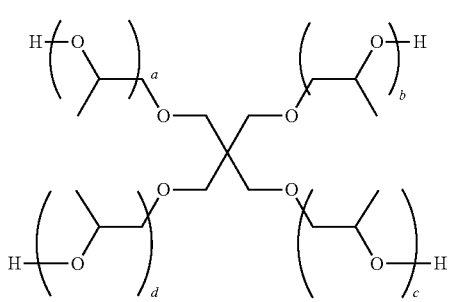<br>/500<br>/458<br>Polyol 6B | 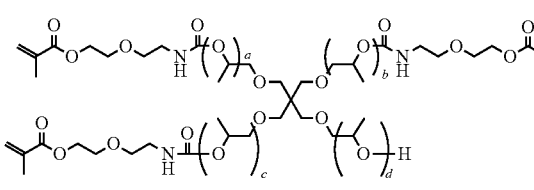<br>Compound 7B<br>/55 |
| 8B | 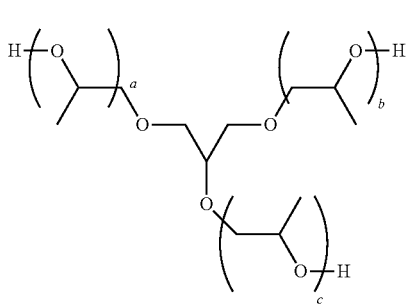<br>/700<br>/251<br>Polyol 3B | 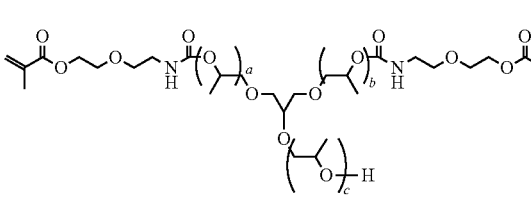<br>Compound 8B<br>/50 |

TABLE 1B-continued

| Production Example | Structural formula/average molecular weight/hydroxyl group value of polyol raw material (mgKOH/g) | Structural formula/hydroxyl group value of main product of hydroxyl group-containing monomer (mgKOH/g) |
|---|---|---|
| 9B | 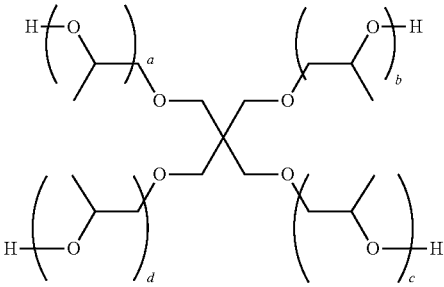 /500 /458 Polyol 6B | 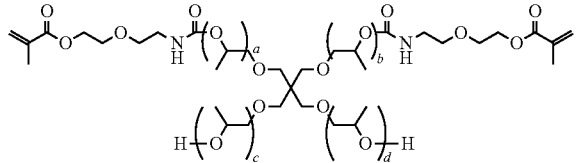 Compound 9B /127 |

Example 1B 10.33 g (5.5 parts by weight) of the compound 1B obtained in Production Example 1B, 0.50 g (8.3 parts by weight) of Bis-GMA (bisphenol A diglycidyl methacrylate, manufactured by Shin-Nakamura Chemical Co, Ltd.), 0.26 g (4.2 parts by weight) of E4BADMA (bisphenol A dimethacrylate ester 4-mole ethylene oxide-modified compound SR540, manufactured by SARTOMER Company), 0.31 g (5.2 parts by weight) of UDMA (2,2,4-trimethylhexamethylenebis(2-carbamoyloxyethyl)dimethacrylate), 0.37 g (6.2 parts by weight) of ETMPTA-3EO (trimethylolpropane triacrylate 3-mole ethylene oxide-modified compound, manufactured by KYOEISHA CHEMICAL Co., Ltd.), 0.37 g (6.1 parts by weight) of MDP (10-methacryloyloxydecyl dihydrogen phosphate), 6.1 mg (0.1 parts by weight) of CQ (camphaquinone, manufactured by Wako Pure Chemical Industries, Ltd.), 0.018 g (0.3 parts by weight) of ethyl 4-(dimethylamino)benzoate (manufactured by Wako Pure Chemical Industries, Ltd.), 2.0 mg (0.03 parts by weight) of BHT (dibutylhydroxytoluene, manufactured by Wako Pure Chemical Industries, Ltd.), 0.015 g (0.25 parts by weight) of 2 hydroxy-4-methoxybenzophenone (manufactured by Wako Pure Chemical Industries, Ltd.) and 3.8 g (64 parts by weight) of a barium aluminum borosilicate glass filler (GM 27884, particle diameter: 1.5 μm, 1.6% silane-treated product, manufactured by NEC SCHOTT Components Corporation) were added into a container, and stirred to uniformity at 50° C. to give a composition to be used as a dental material. The composition of Example 1B is, for example, a composition suitable for evaluation of performance as a resin.

[Adhesive Strength Test Method]

A bovine lower anterior tooth extracted and kept in a frozen state was thawed by injection of water, and subjected to root amputation and pulp extirpation treatment. This was placed in a plastic cylindrical container having a diameter of 25 mm and a depth of 25 mm, and embedded in an acrylic resin. The surface thereof was wet-polished with #120 and #400 emery papers to expose enamel and dentin flat surfaces in a state of being parallel to the lip surface.

Next, compressed air was blown onto the flat surfaces for about 1 second to perform drying, a plastic mold having a diameter of 2.38 mm (manufactured by Ultradent Products, Inc.) was then placed on the enamel or dentin flat surface, and the prepared composition was packed in the mold in two parts, then irradiated with light from a visible light irradiator (Translux 2Wave, manufactured by Heraeus Kulzer GmbH) for 20 seconds, and thereby cured. Thereafter, the mold was removed to prepare an adhesive sample. The sample was stored in warm water at 37° C. for 24 hours, and a shear load which was parallel to the enamel or dentin surface and in contact with the surface of the bovine tooth was then applied at a cross head speed of 1.0 mm/min using a general-purpose tester (Precise Versatile Material Tester 210x, manufactured by INTESCO Co., Ltd.). The shear adhesive strength was determined from the shear load at the time when the columnar composition formed on the bovine tooth surface was separated from the surface.

The results of the shear tests of the obtained compositions to be used as dental materials are shown in Table 2B.

Comparative Example 1B

A composition to be used as a dental material was obtained by following the operation in Example 1B except that HEMA (Acryester HO (registered trademark), manufactured by Mitsubishi Rayon Co., Ltd.) was used in place of the compound 1B. Further, the same operation as in Example 1B was carried out to obtain shear test results. The results are shown in Table 2B.

Comparative Example 2B

A composition to be used as a dental material was obtained by following the operation in Example 1B except that the compound 1B was not added. Further, the same operation as in Example 1B was carried out to obtain shear test results. The results are shown in Table 2B.

TABLE 2B

| | Bonding performance | | |
|---|---|---|---|
| | | Results of shear test on bovine tooth | |
| | Primer monomers | Enamel (MPa) | Dentin (MPa) |
| Example 1B | Compound 1B | 16.1 | 12.0 |
| Comparative Example 1B | HEMA | 9.0 | 11.8 |

TABLE 2B-continued

| | Bonding performance | | |
|---|---|---|---|
| | | Results of shear test on bovine tooth | |
| | Primer monomers | Enamel (MPa) | Dentin (MPa) |
| Comparative Example 2B | None | 9.5 | 7.8 |

The results in Table 2B have shown that the dental hydroxyl group-containing polymerizable monomer according to the second aspect of the invention had higher adhesive strength to and a higher primer effect on the bovine tooth, particularly the enamel as compared to the conventional hydroxyl group-containing dental compounds. Thus, it has been indicated that the use of the dental hydroxyl group-containing polymerizable monomer according to the second aspect of the invention makes it possible to provide a dental material having a high ability to prime the tooth.

Example 2B 0.40 g (20 parts by weight) of the compound 1B obtained in Production Example 1B, 0.20 g (10 parts by weight) of UDMA (2,2,4-trimethylhexamethylenebis(2-carbamoyloxyethyl)dimethacrylate), 0.20 g (10 parts by weight) of TEGDMA (triethylene glycol dimethacrylate: NK Ester 3G, manufactured by Shin-Nakamura Chemical Co, Ltd.), 0.26 g (13 parts by weight) of MDP (10-methacryloyloxydecyl dihydrogen phosphate), 0.020 g (1.0 part by weight) of CQ (camphaquinone, manufactured by Wako Pure Chemical Industries, Ltd.), 0.020 g (1.0 part by weight) of 2-butoxyethyl 4-(dimethylamino)benzoate (manufactured by Tokyo Chemical Industry Co., Ltd.), 0.60 g (30 parts by weight) of ethanol (ultradehydrated, manufactured by Wako Pure Chemical Industries, Ltd.) and 0.30 g (15 parts by weight) of distilled water were added into a container, and stirred to uniformity at 50° C. to give a composition to be used as a dental material. The composition of Example 2B is, for example, a composition suitable for evaluation of performance as a bonding material.

[Adhesive Strength Test Method]

A bovine lower anterior tooth extracted and kept in a frozen state was thawed by injection of water, and subjected to root amputation and pulp extirpation treatment. This was placed in a plastic cylindrical container having a diameter of 25 mm and a depth of 25 mm, and embedded in an acrylic resin. The surface thereof was wet-polished with #120 and #400 emery papers to expose an enamel in a state of being parallel to the lip surface.

Next, compressed air was blown onto the flat surface for about 1 second to perform drying, the prepared composition was then applied to the enamel flat surface, and compressed air was blown with a low blowing force to remove the solvent. The surface of the applied composition was irradiated with light from a visible light irradiator (Translux 2Wave, manufactured by Heraeus Kulzer GmbH) for 20 seconds. Further, a plastic mold having a diameter of 2.38 mm (manufactured by Ultradent Products, Inc.) was then placed thereon, and a dental composite resin (Venus Diamond, manufactured by Heraeus Kulzer GmbH) was packed, irradiated with light from the visible light irradiator for 20 seconds, and thereby cured. Thereafter, the mold was removed to prepare an adhesive sample. The sample was stored in warm water at 37° C. for 24 hours, and a shear load which was parallel to the enamel and in contact with the surface of the bovine tooth was then applied at a cross head speed of 1.0 mm/min using a general-purpose tester (Precise Versatile Material Tester 210×, manufactured by INTESCO Co., Ltd.). The shear adhesive strength was determined from the shear load at the time when the columnar composition formed on the bovine tooth surface was separated from the surface.

The results of the shear tests of the dental compositions are shown in Table 3B.

Examples 3B to 5B

Except that the hydroxyl group-containing monomers 3B, 4B and 6B obtained in Production Examples above were used in place of the compound 1B, the same operation as in Example 2B was carried out to prepare compositions to be used as dental materials. Subsequently, the same test as in Example 2B was conducted to obtain shear test results. The results are shown in Table 3B.

Comparative Example 3

Except that HEMA (Acryester HO (registered trademark), manufactured by Mitsubishi Rayon Co., Ltd.) was used in place of the compound 1B, the same operation as in Example 2B was carried out to prepare a composition to be used as a dental material. Subsequently, the same test as in Example 2B was conducted to obtain shear test results. The results are shown in Table 3B.

TABLE 3B

| | Bonding performance | |
|---|---|---|
| | Primer monomers | Results of shear test on bovine tooth Enamel (MPa) |
| Example 2B | Compound 1B | 19.0 |
| Example 3B | Compound 3B | 15.9 |
| Example 4B | Compound 4B | 20.2 |
| Example 5B | Compound 6B | 16.6 |
| Comparative Example 3B | HEMA | 14.2 |

Examples 6B to 13B

Except that the bovine tooth dentin was used in place of the bovine tooth enamel, and compounds shown in Table 4B were used, the same operation as in Example 2B was carried out to prepare compositions to be used as dental materials. Subsequently, the same test as in Example 2B was conducted to obtain shear test results. The results are shown in Table 4B.

Comparative Example 4B

Except that HEMA (Acryester HO (registered trademark), manufactured by Mitsubishi Rayon Co., Ltd.) was used in place of the compound 1B, the same operation as in Example 6B was carried out to prepare a composition to be used as a dental material. Subsequently, the same test as in Example 2 was conducted to obtain shear test results. The results are shown in Table 4B.

TABLE 4B

| | Bonding performance | |
|---|---|---|
| | Primer monomers | Results of shear test on bovine tooth Dentin(MPa) |
| Example 6B | Compound 1B | 10.0 |
| Example 7B | Compound 3B | 10.0 |
| Example 8B | Compound 4B | 9.4 |
| Example 9B | Compound 5B | 9.5 |
| Example 10B | Compound 6B | 10.4 |
| Example 11B | Compound 7B | 7.0 |
| Example 12B | Compound 8B | 4.8 |
| Example 13B | Compound 9B | 8.2 |
| Comparative Example 4B | HEMA | 3.1 |

The results in Tables 3B and 4B have shown that the dental hydroxyl group-containing polymerizable monomers of the invention achieved enhancement in adhesive strength to and primer effect on the bovine tooth enamel and dentin as compared to the conventional hydroxyl group-containing dental compounds. Thus, it has been indicated that the use of the dental polymerizable monomers of the invention makes it possible to provide dental material having a high ability to prime the tooth.

The invention claimed is:

1. A dental material comprising a dental polyfunctional monomer of general formula (8A), in which a core (X) and a terminal group (Y2A) are bonded to each other directly or via a linking group (Z):

$$X(Y2A)_{n^{8aA}}(Z{-}Y2A)_{n^{8bA}} \quad (8A)$$

wherein in the general formula (8A), $n^{8aA}$ represents a number of terminal groups (Y2A) directly bonded to the core (X), $n^{8bA}$ represents a number of terminal groups (Y2A) bonded to the core (X) via the linking group (Z), and a sum of $n^{8aA}$ and $n^{8bA}$ is equal to a valence of the core (X), provided that $n^{8bA}$ is not 0;

the terminal group (Y2A) is a (meth)acryloyl group-containing group (Y3) represented by general formula (9), a (meth)acryloyl group or a $C_{1-20}$ hydrocarbon group, and a plurality of the terminal groups (Y2A) may be the same as or different from each other, with the proviso that among all the terminal groups (Y2A) in the compound represented by the general formula (8A), three or more of the terminal groups are (meth)acryloyl group-containing groups (Y3) or (meth)acryloyl groups, and one or more of the terminal groups are (meth)acryloyl group-containing groups (Y3); and the linking group (Z) is a divalent group represented by general formula (2), and when the compound represented by the general formula (8A) contains a plurality of the linking groups (Z), the linking groups (Z) may be the same as or different from each other;

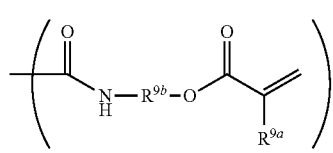
(9)

wherein in the general formula (9), $R^{9a}$ represents a hydrogen atom or a methyl group, $R^{9b}$ represents a $C_{2-6}$ linear alkylene group or a $C_{2-6}$ linear oxyalkylene group, and the linear alkylene group or the linear oxyalkylene group is optionally substituted with a $C_{1-6}$ alkyl group and/or a (meth)acryloyloxymethylene group in place of a hydrogen atom; and

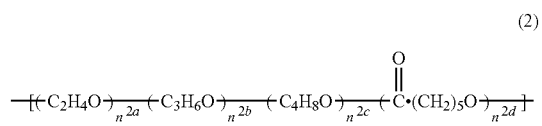
(2)

wherein in the general formula (2), $n^{2a}$, $n^{2b}$, $n^{2c}$ and $n^{2d}$ represent unit numbers of respective repeating units, and are each 0 to 100, a sum of $n^{2a}$, $n^{2b}$, $n^{2c}$ and $n^{2d}$ is 1 to 100, a left end of the group is bonded to the core (X), and a right end of the group is bonded to the terminal group (Y2A), wherein the core (X) is at least one selected from the group consisting of groups represented by general formulas (6a) to (6j):

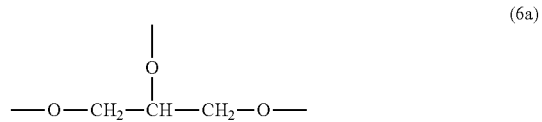
(6a)

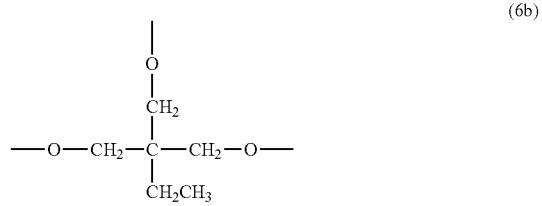
(6b)

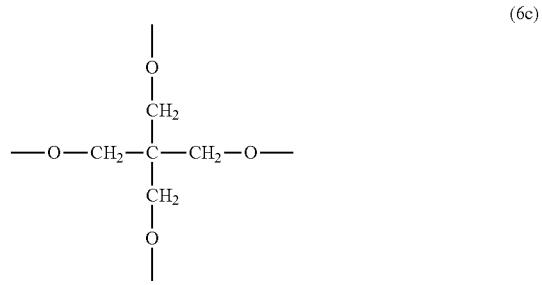
(6c)

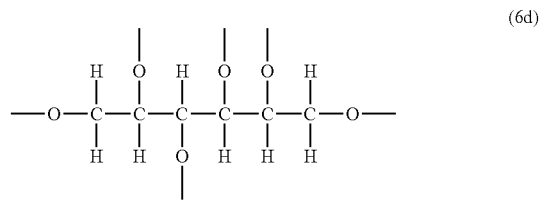
(6d)

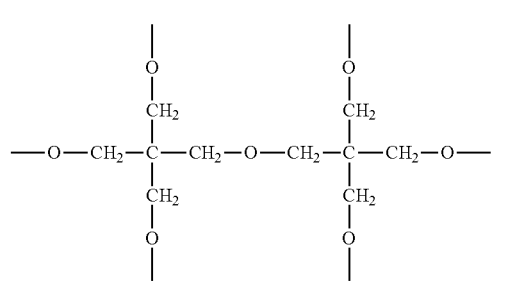
(6e)

(6f)

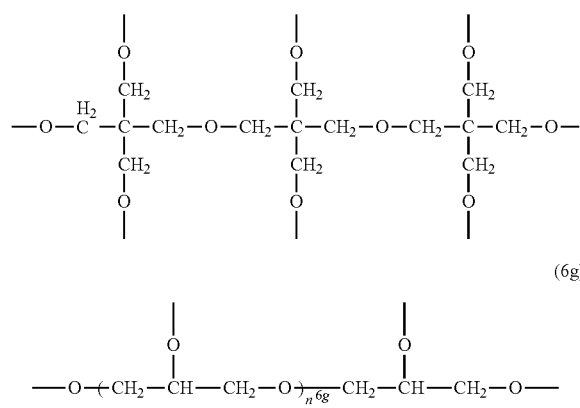

(6g)

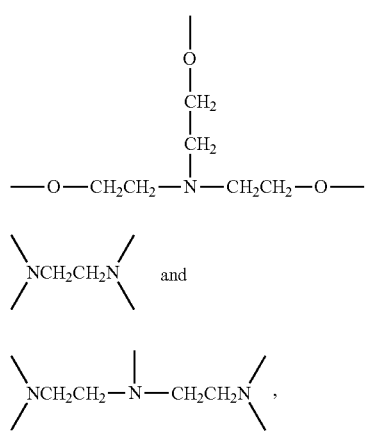

wherein the general formula (6g), $n^{6g}$ is an integer of 1 to 40, (6h)

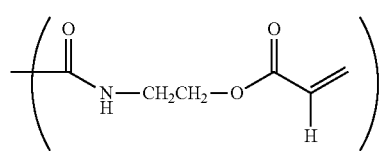

(6i)

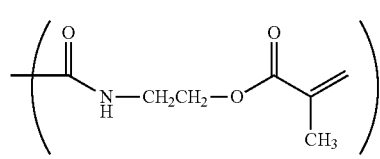  and (6j)

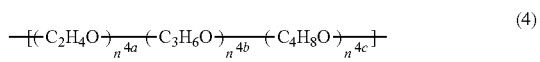

wherein the dental material further comprises at least one filler selected from the group consisting of glasses calcium fluoride, ytterbium fluoride, calcium phosphate, barium sulfate, zirconium dioxide, titanium dioxide and hydroxyapatite.

2. The dental material according to claim 1, wherein the core (X) is an organic group having a valence of 3 to 12.

3. The dental material according to claim 1, wherein the (meth)acryloyl group-containing group (Y3) is at least one selected from the group consisting of groups represented by general formulas (9a) to (9f):

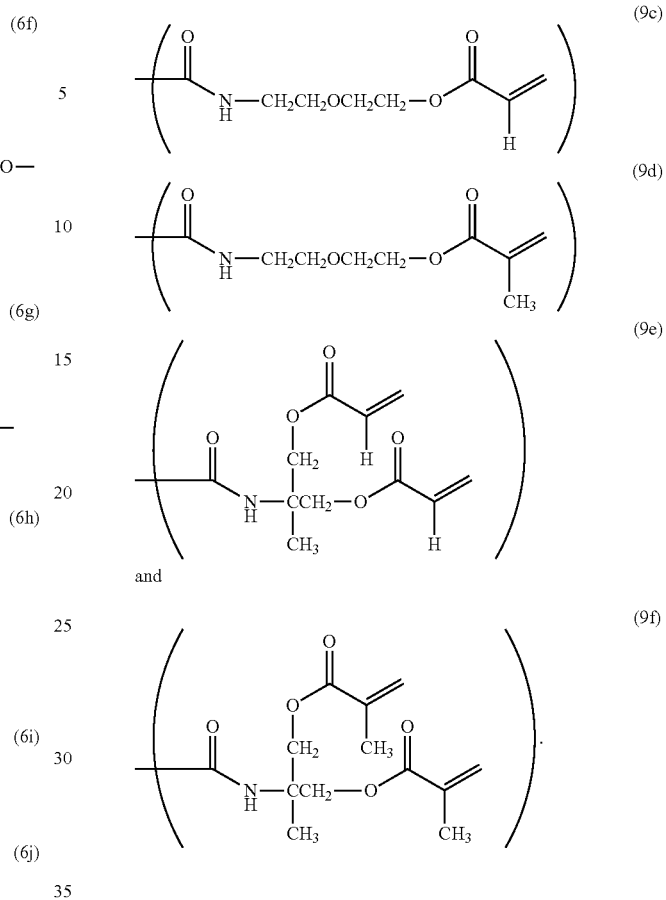

4. The dental material according to claim 1, wherein the (meth)acryloyl group-containing group (Y3) is a group represented by general formula (9b):

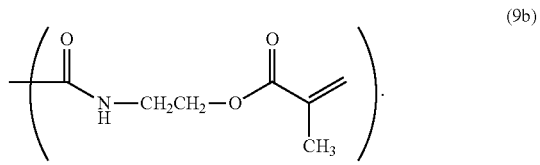

5. The dental material according to claim 1, wherein in the linking group (Z), $n^{2a}$, $n^{2b}$, $n^{2c}$ and $n^{2d}$ are each 0 to 20, and the sum of $n^{2a}$, $n^{2b}$, $n^{2c}$ and $n^{2d}$ is 1 to 20.

6. The dental material according to claim 1, wherein the linking group (Z) is a divalent group represented by general formula (4):

$$-[(C_2H_4O)_{n^{4a}}(C_3H_6O)_{n^{4b}}(C_4H_8O)_{n^{4c}}]- \quad (4)$$

wherein in the general formula (4), $n^{4a}$, $n^{4b}$ and $n^{4c}$ represent unit numbers of respective repeating units, and are each 0 to 20, a sum of $n^{4a}$, $n^{4b}$ and $n^{4c}$ is 1 to 20, a left end of the group is bonded to the core (X), and a right end of the group is bonded to the terminal group (Y2A).

7. The dental material according to claim 1, wherein the linking group (Z) is a divalent group represented by general formula (5):

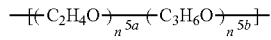 (5)

wherein in the general formula (5), $n^{5a}$ and $n^{5b}$ represent unit numbers of respective repeating units, and are each 0 to 20, a sum of $n^{5a}$ and $n^{5b}$ is 1 to 20, a left end of the group is bonded to the core (X), and a right end of the group is bonded to the terminal group (Y2A).

8. A cured product obtained by curing the dental material according to claim 1.

9. A dental material comprising a dental polyfunctional monomer which is a product of reaction of a compound represented by general formula (1A), in which a core (X) and a terminal group (Y1A) are bonded to each other directly or via a linking group (Z), with a (meth)acryloyl group-containing isocyanate compound represented by general formula (3):

$$X(Y1A)n^{1aA}(Z-Y1A)n^{1bA} \quad (1A)$$

wherein in the general formula (1A), $n^{1aA}$ represents a number of terminal groups (Y1A) directly bonded to the core (X), $n^{1bA}$ represents a number of terminal groups (Y1A) bonded to the core (X) via the linking group (Z), and a sum of $n^{1aA}$ and $n^{1bA}$ is equal to a valence of the core (X), provided that $n^{1bA}$ is not 0;

the core (X) is a $C_{1-200}$ polyvalent organic group having a valence of not less than 3 containing at least three oxygen atoms, or nitrogen atoms, or a mixture thereof, in which each atom bonded to the terminal group (Y1A) or the linking group (Z) is an oxygen or nitrogen atom;

the terminal group (Y1A) is a (meth)acryloyl group, a $C_{1-20}$ monovalent hydrocarbon group or an active hydrogen atom, and a plurality of the terminal groups (Y1A) may be the same as or different from each other, with the proviso that among the terminal groups (Y1A) in the compound represented by the general formula (1A), three or more of the terminal groups are active hydrogen atoms or (meth)acryloyl groups, and one or more of the terminal groups are active hydrogen atoms; and the linking group (Z) is a divalent group represented by general formula (2), and when the compound represented by the general formula (1A) contains a plurality of the linking groups (Z), the linking groups (Z) may be the same as or different from each other;

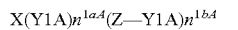 (2)

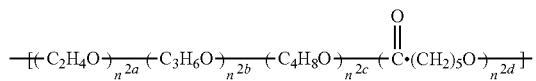

wherein in the general formula (2), $n^{2a}$, $n^{2b}$, $n^{2c}$ and $n^{2d}$ represent unit numbers of respective repeating units, and are each 0 to 100, a sum of $n^{2a}$, $n^{2b}$, $n^{2c}$ and $n^{2d}$ is 1 to 100, a left end of the group is bonded to the core (X), and a right end of the group is bonded to the terminal group (Y1A); and

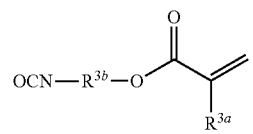 (3)

wherein in the general formula (3), $R^{3a}$ represents a hydrogen atom or a methyl group, $R^{3b}$ represents a $C_{2-6}$ linear alkylene group or a $C_{2-6}$ linear oxyalkylene group, and the linear alkylene group or the linear oxyalkylene group is optionally substituted with a $C_{1-6}$ alkyl group and/or a (meth)acryloyloxymethylene group in place of a hydrogen atom, under a condition of (total equivalents/moles of isocyanate groups present in the reaction derived from the compound represented by the general formula (3))/ (total equivalents/moles of active hydrogen atoms of (Y1A) bonded to terminal oxygen atoms and nitrogen atoms of the core (X) present in the compound represented by general formula (1A))=1, wherein the compound (1A) is at least one selected from the group consisting of compounds represented by general formulas (6'a) to (6'k):

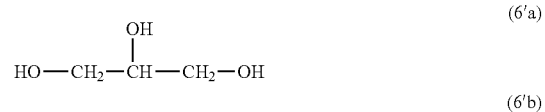 (6'a)

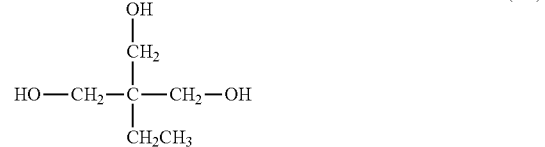 (6'b)

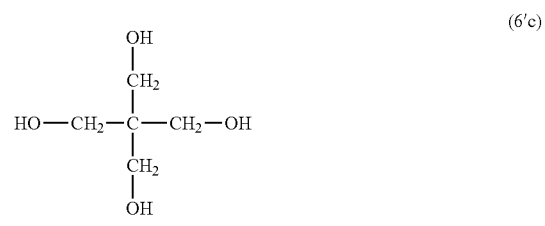 (6'c)

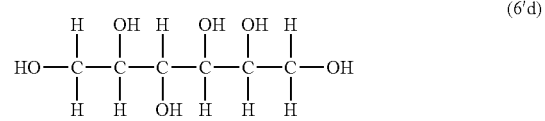 (6'd)

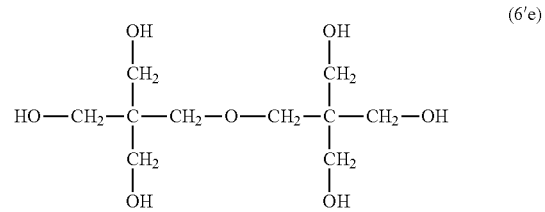 (6'e)

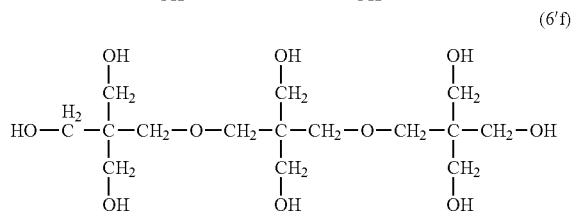 (6'f)

-continued

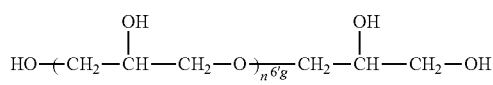   (6'g)

wherein the general formula (6g), $n^{6'g}$ is an integer of 1 to 40,

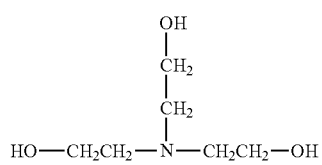   (6'h)

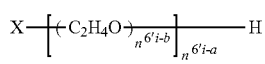   (6'i)

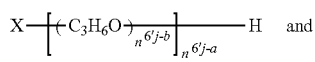   (6'j)   and

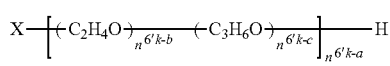   (6'k)

wherein $n^{6'i-a}$, $n^{6'j-a}$ and $n^{6'k-a}$ in the general formulas (6'i), (6'j) and (6'k) each represent a number of arms of a polyol bonded to the core X, and are each an integer of not less than 3; and $n^{6'i-b}$ and $n^{6'j-b}$ in the general formulas (6'i) and (6'j) represent numbers of oxyethylene units and oxypropylene units, respectively, and are each in the range of 1 to 100, the numbers of units for respective arms may be the same as or different from each other, $n^{6'k-b}$ and $n^{6'k-c}$ in the general formula (6'k) represent numbers of oxyethylene units and oxypropylene units, respectively, a sum thereof is in the range of 1 to 100, and the sums of the numbers of units for respective arms may be the same as or different from each other, wherein the dental material further comprises at least one filler selected from the group consisting of glasses, calcium fluoride, ytterbium fluoride, calcium phosphate, barium sulfate, zirconium dioxide, titanium dioxide and hydroxyapatite.

10. The dental material according to claim 9, wherein all terminal groups (Y1A) in the general formula (1A) are hydrogen atoms.

11. The dental material according to claim 9, wherein in the linking group (Z), $n^{2a}$, $n^{2b}$, $n^{2c}$ and $n^{2d}$ are each 0 to 20, and the sum of $n^{2a}$, $n^{2b}$, $n^{2c}$ and $n^{2d}$ is 1 to 20.

12. The dental material according to claim 9, wherein the linking group (Z) is a divalent group represented by general formula (4):

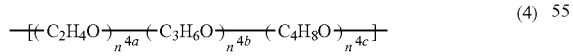   (4)

wherein in the general formula (4), $n^{4a}$, $n^{4b}$ and $n^{4c}$ represent unit numbers of respective repeating units, and are each 0 to 20, a sum of $n^{4a}$, $n^{4b}$ and $n^{4c}$ is 1 to 20, a left end of the group is bonded to the core (X), and a right end of the group is bonded to the terminal group (Y1A).

13. The dental material according to claim 9, wherein the linking group (Z) is a divalent group represented by general formula (5):

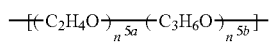   (5)

wherein in the general formula (5), $n^{5a}$ and $n^{5b}$ represent unit numbers of respective repeating units, and are each 0 to 20, a sum of $n^{5a}$ and $n^{5b}$ is 1 to 20, a left end of the group is bonded to the core (X), and a right end of the group is bonded to the terminal group (Y1A).

14. The dental material according to claim 9, wherein the core (X) is an organic group having a valence of 3 to 12.

15. The dental material according to claim 9, wherein the (meth)acryloyl group-containing isocyanate compound represented by the general formula (3) is at least one selected from the group consisting of compounds represented by general formulas (3a) to (3f):

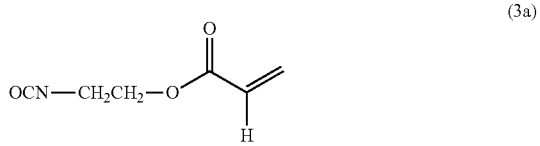   (3a)

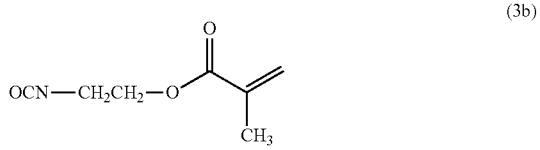   (3b)

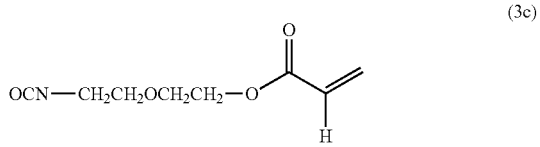   (3c)

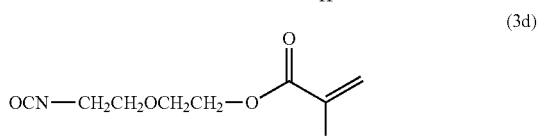   (3d)

   (3e)

and

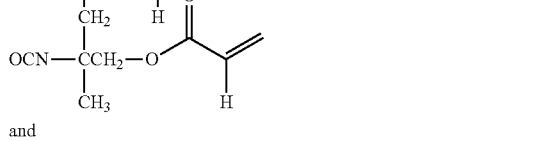   (3f)

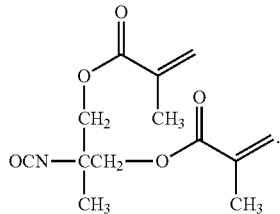

16. A cured product obtained by curing the dental material according to claim 9.

17. A dental treatment method comprising a step of curing in a mouth of a patient in need thereof a dental material composition that comprises a dental polyfunctional monomer, a polymerization initiator, and at least one filler selected from the group consisting of glasses, calcium fluoride, ytterbium fluoride, calcium phosphate, barium sulfate, zirconium dioxide, titanium dioxide and hydroxyapatite, wherein the dental polyfunctional monomer is represented by general formula (8A), in which a core (X) and a terminal group (Y2A) are bonded to each other directly or via a linking group (Z):

$$X(Y2A)_{n^{8aA}}(Z-Y2A)_{n^{8bA}} \quad (8A)$$

wherein in the general formula (8A), $n^{8aA}$ represents a number of terminal groups (Y2A) directly bonded to the core (X), $n^{8bA}$ represents a number of terminal groups (Y2A) bonded to the core (X) via the linking group (Z), and a sum of $n^{8aA}$ and $n^{8bA}$ is equal to a valence of the core (X), provided that $n^{8bA}$ is not 0;

the terminal group (Y2A) is a (meth)acryloyl group-containing group (Y3) represented by general formula (9), a (meth)acryloyl group or a $C_{1-20}$ hydrocarbon group, and a plurality of the terminal groups (Y2A) may be the same as or different from each other, with the proviso that among all the terminal groups (Y2A) in the compound represented by the general formula (8A), three or more of the terminal groups are (meth)acryloyl group-containing groups (Y3) or (meth)acryloyl groups, and one or more of the terminal groups are (meth)acryloyl group-containing groups (Y3); and the linking group (Z) is a divalent group represented by general formula (2), and when the compound represented by the general formula (8A) contains a plurality of the linking groups (Z), the linking groups (Z) may be the same as or different from each other;

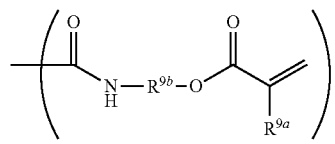

(9)

wherein in the general formula (9), $R^{9a}$ represents a hydrogen atom or a methyl group, $R^{9b}$ represents a $C_{2-6}$ linear alkylene group or a $C_{2-6}$ linear oxyalkylene group, and the linear alkylene group or the linear oxyalkylene group is optionally substituted with a $C_{1-6}$ alkyl group and/or a (meth)acryloyloxymethylene group in place of a hydrogen atom; and

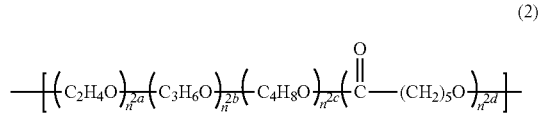

(2)

wherein in the general formula (2), $n^{2a}$, $n^{2b}$, $n^{2c}$ and $n^{2d}$ represent unit numbers of respective repeating units, and are each 0 to 100, a sum of $n^{2a}$, $n^{2b}$, $n^{2c}$ and $n^{2d}$ is 1 to 100, a left end of the group is bonded to the core (X), and a right end of the group is bonded to the terminal group (Y2A), wherein the core (X) is at least one selected from the group consisting of groups represented by general formulas (6a) to (6j):

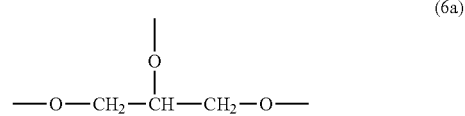

(6a)

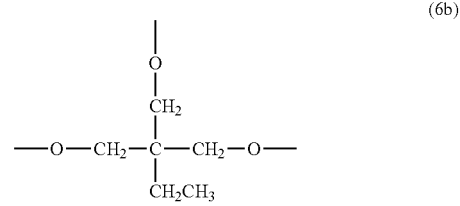

(6b)

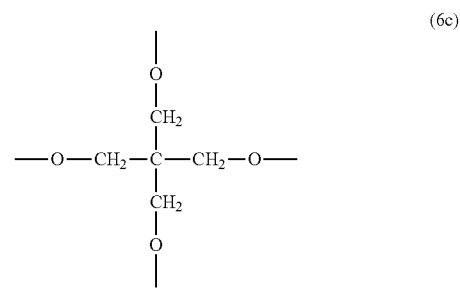

(6c)

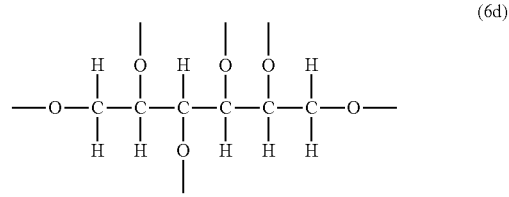

(6d)

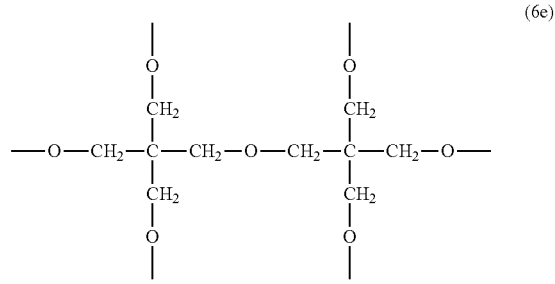

(6e)

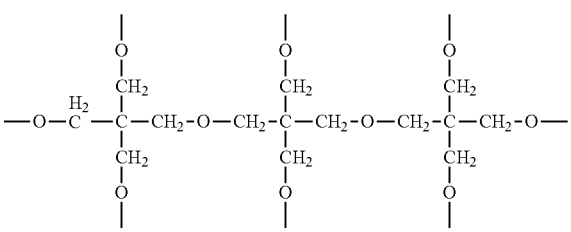

(6f)

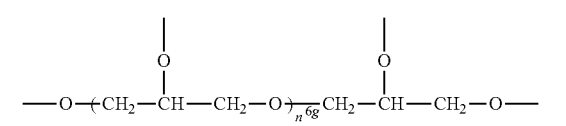

(6g)

wherein in general formula (6g), $n^{6g}$ is an integer of 1 to 40, (6h)

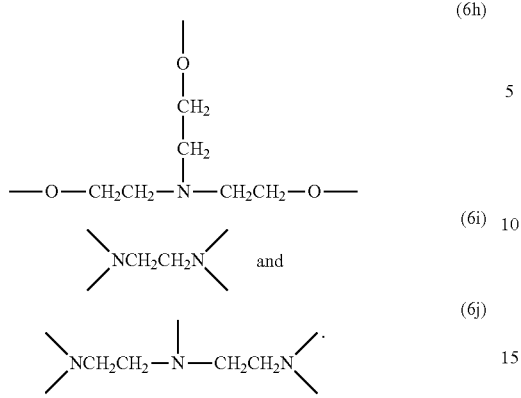

(6i)

(6j)

18. A dental treatment method comprising a step of curing outside a mouth of a patient in need thereof a dental material composition that comprises a dental polyfunctional monomer, a polymerization initiator, and at least one filler selected from the group consisting of glasses, calcium fluoride, ytterbium fluoride, calcium phosphate, barium sulfate, zirconium dioxide, titanium dioxide and hydroxyapatite, to obtain a cured product, and a step of applying the cured product into the mouth, wherein the dental polyfunctional monomer is represented by general formula (8A), in which a core (X) and a terminal group (Y2A) are bonded to each other directly or via a linking group (Z):

$$X(Y2A)_{n^{8aA}}(Z-Y2A)_{n^{8bA}} \quad (8A)$$

wherein in the general formula (8A), $n^{8aA}$ represents a number of terminal groups (Y2A) directly bonded to the core (X), $n^{8bA}$ represents a number of terminal groups (Y2A) bonded to the core (X) via the linking group (Z), and a sum of $n^{8aA}$ and $n^{8bA}$ is equal to a valence of the core (X), provided that $n^{8bA}$ is not 0;

the terminal group (Y2A) is a (meth)acryloyl group-containing group (Y3) represented by general formula (9), a (meth)acryloyl group or a $C_{1-20}$ hydrocarbon group, and a plurality of the terminal groups (Y2A) may be the same as or different from each other, with the proviso that among all the terminal groups (Y2A) in the compound represented by the general formula (8A), three or more of the terminal groups are (meth)acryloyl group-containing groups (Y3) or (meth)acryloyl groups, and one or more of the terminal groups are (meth)acryloyl group-containing groups (Y3); and the linking group (Z) is a divalent group represented by general formula (2), and when the compound represented by the general formula (8A) contains a plurality of the linking groups (Z), the linking groups (Z) may be the same as or different from each other;

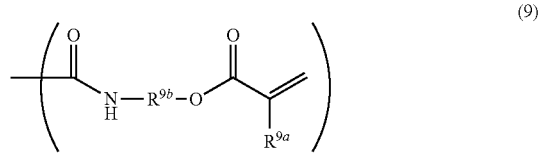

(9)

wherein in the general formula (9), $R^{9a}$ represents a hydrogen atom or a methyl group, $R^{9b}$ represents a $C_{2-6}$ linear alkylene group or a $C_{2-6}$ linear oxyalkylene group, and the linear alkylene group or the linear oxyalkylene group is optionally substituted with a $C_{1-6}$ alkyl group and/or a (meth)acryloyloxymethylene group in place of a hydrogen atom; and

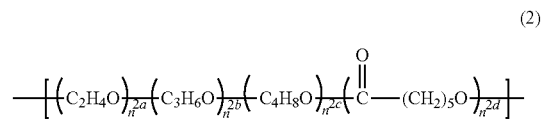

(2)

wherein in the general formula (2), $n^{2a}$, $n^{2b}$, $n^{2c}$ and $n^{2d}$ represent unit numbers of respective repeating units, and are each 0 to 100, a sum of $n^{2a}$, $n^{2b}$, $n^{2c}$ and $n^{2d}$ is 1 to 100, a left end of the group is bonded to the core (X), and a right end of the group is bonded to the terminal group (Y2A), wherein the core (X) is at least one selected from the group consisting of groups represented by general formulas (6a) to (6j):

(6a)

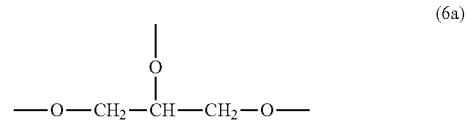

(6b)

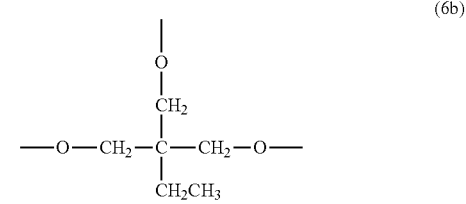

(6c)

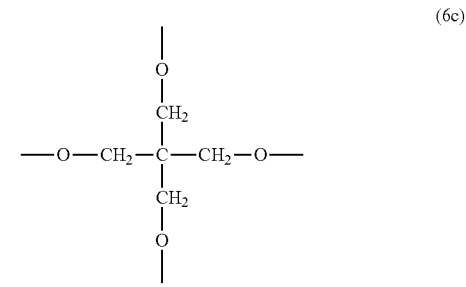

(6d)

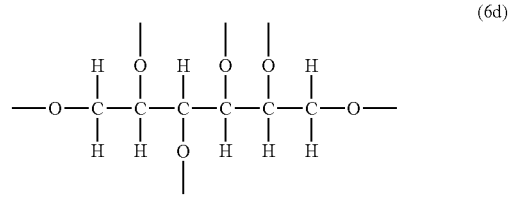

(6e)

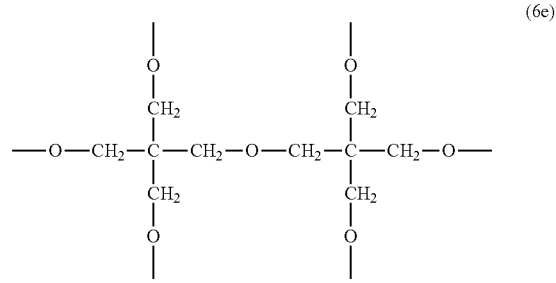

(6f)

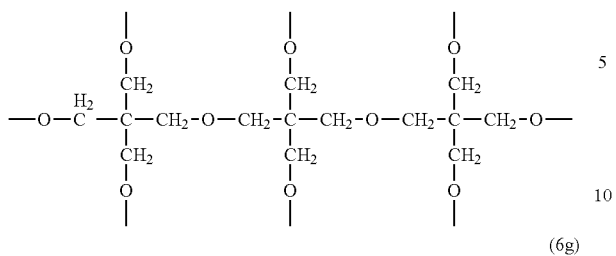

(6g)

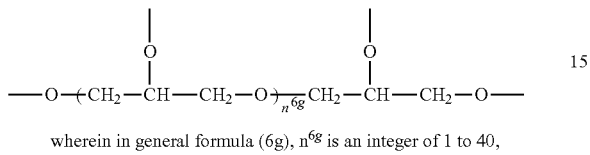

wherein in general formula (6g), $n^{6g}$ is an integer of 1 to 40, (6h)

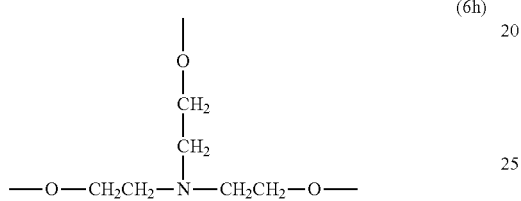

(6i)

 and (6j)

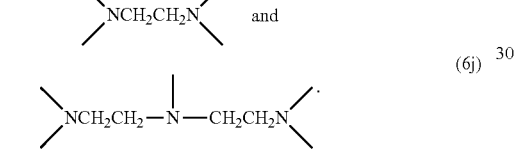

19. A dental treatment method comprising a step of curing in a mouth of a patient in need thereof a dental material composition that comprises a dental polyfunctional monomer, a polymerization initiator, and at least one filler selected from the group consisting of glasses, calcium fluoride, ytterbium fluoride, calcium phosphate, barium sulfate, zirconium dioxide, titanium dioxide and hydroxyapatite, wherein the dental polyfunctional monomer is a product of reaction of a compound represented by general formula (1A), in which a core (X) and a terminal group (Y1A) are bonded to each other directly or via a linking group (Z), with a (meth)acryloyl group-containing isocyanate compound represented by general formula (3):

$$X(Y1A)_{n^{1aA}}(Z-Y1A)_{n^{1bA}}$$ (1A)

wherein in the general formula (1A), $n^{1aA}$ represents a number of terminal groups (Y1A) directly bonded to the core (X), $n^{1bA}$ represents a number of terminal groups (Y1A) bonded to the core (X) via the linking group (Z), and a sum of $n^{1aA}$ and $n^{1bA}$ is equal to a valence of the core (X), provided that $n^{1bA}$ is not 0;

the core (X) is a $C_{1-200}$ polyvalent organic group having a valence of not less than 3 containing at least three oxygen atoms, or nitrogen atoms, or a mixture thereof, in which each atom bonded to the terminal group (Y1A) or the linking group (Z) is an oxygen or nitrogen atom;

the terminal group (Y1A) is a (meth)acryloyl group, a $C_{1-20}$ monovalent hydrocarbon group or an active hydrogen atom, and a plurality of the terminal groups (Y1A) may be the same as or different from each other, with the proviso that among the terminal groups (Y1A) in the compound represented by the general formula (1A), three or more of the terminal groups are active hydrogen atoms or (meth)acryloyl groups, and one or more of the terminal groups are active hydrogen atoms; and the linking group (Z) is a divalent group represented by general formula (2), and when the compound represented by the general formula (1A) contains a plurality of the linking groups (Z), the linking groups (Z) may be the same as or different from each other;

(2)

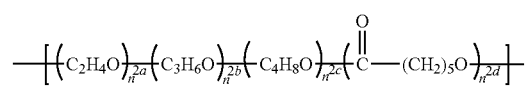

wherein in the general formula (2), $n^{2a}$, $n^{2b}$, $n^{2c}$ and $n^{2d}$ represent unit numbers of respective repeating units, and are each 0 to 100, a sum of $n^{2a}$, $n^{2b}$, $n^{2c}$ and $n^{2d}$ is 1 to 100, a left end of the group is bonded to the core (X), and a right end of the group is bonded to the terminal group (Y1A); and (3)

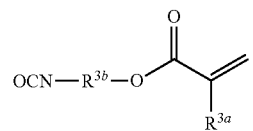

wherein in the general formula (3), $R^{3a}$ represents a hydrogen atom or a methyl group, $R^{3b}$ represents a $C_{2-6}$ linear alkylene group or a $C_{2-6}$ linear oxyalkylene group, and the linear alkylene group or the linear oxyalkylene group is optionally substituted with a $C_{1-6}$ alkyl group and/or a (meth)acryloyloxymethylene group in place of a hydrogen atom, under a condition of (total equivalents/moles of isocyanate groups present in the reaction derived from the compound represented by the general formula (3))/ (total equivalents/moles of active hydrogen atoms of (Y1A) bonded to terminal oxygen atoms and nitrogen atoms of the core (X) present in the compound represented by general formula (1A))=1, wherein the compound (1A) is at least one selected from the group consisting of compounds represented by general formulas (6'a) to (6'k):

(6'a)

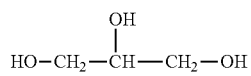

(6'b)

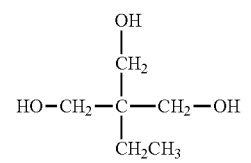

-continued

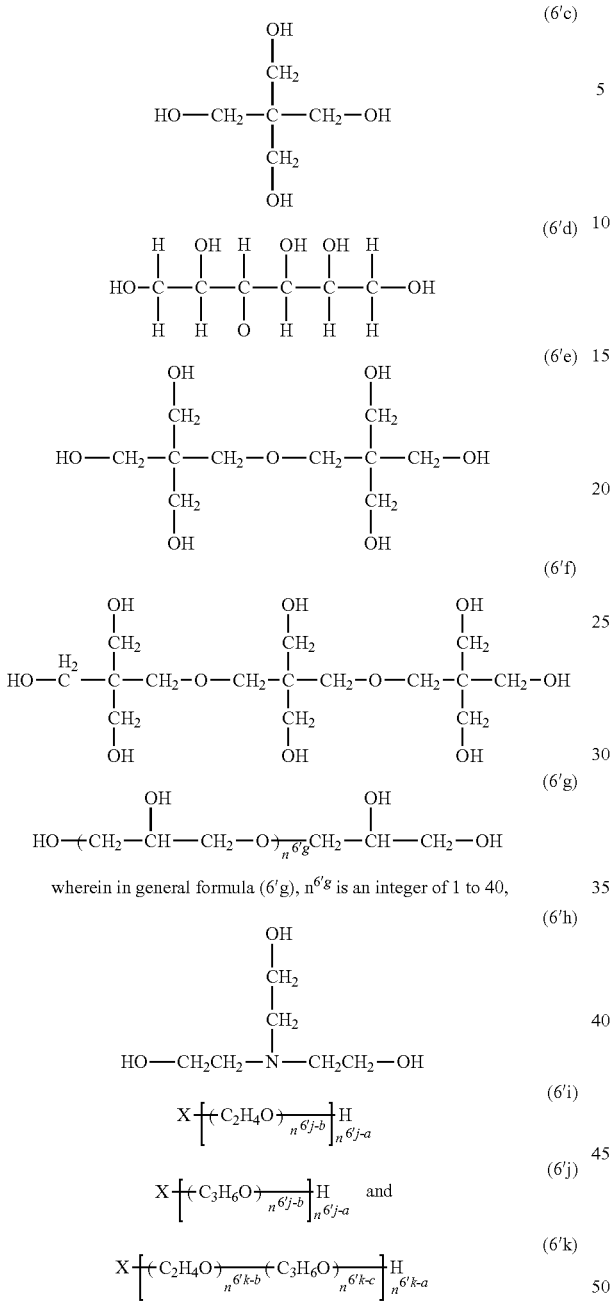

wherein in general formula (6'g), $n^{6'g}$ is an integer of 1 to 40, wherein $n^{6'i-a}$, $n^{6'j-a}$ and $n^{6'k-a}$ in the general formulas (6'i), (6'j) and (6'k) each represent a number of arms of a polyol bonded to the core X, and are each an integer of not less than 3; and $n^{6'i-b}$ and $n^{6'j-b}$ in the general formulas (6'i) and (6'j) represent numbers of oxyethylene units and oxypropylene units, respectively, and are each in the range of 1 to 100, the numbers of units for respective arms may be the same as or different from each other, $n^{6'k-b}$ and $n^{6'k-c}$ in the general formula (6'k) represent numbers of oxyethylene units and oxypropylene units, respectively, a sum thereof is in the range of 1 to 100, and the sums of the numbers of units for respective arms may be the same as or different from each other.

20. A dental treatment method comprising a step of curing outside a mouth of a patient in need thereof a dental material composition that comprises a dental polyfunctional monomer, a polymerization initiator, and at least one filler selected from the group consisting of glasses, calcium fluoride, ytterbium fluoride, calcium phosphate, barium sulfate, zirconium dioxide, titanium dioxide and hydroxyapatite, to obtain a cured product, and a step of applying the cured product into the mouth, wherein the dental polyfunctional monomer is a product of reaction of a compound represented by general formula (1A), in which a core (X) and a terminal group (Y1A) are bonded to each other directly or via a linking group (Z), with a (meth)acryloyl group-containing isocyanate compound represented by general formula (3):

$$X(Y1A)n^{1aA}(Z-Y1A)n^{1bA} \qquad (1A)$$

wherein in the general formula (1A), $n^{1aA}$ represents a number of terminal groups (Y1A) directly bonded to the core (X), $n^{1bA}$ represents a number of terminal groups (Y1A) bonded to the core (X) via the linking group (Z), and a sum of $n^{1aA}$ and $n^{1bA}$ is equal to a valence of the core (X), provided that $n^{1bA}$ is not 0;

the core (X) is a $C_{1-200}$ polyvalent organic group having a valence of not less than 3 containing at least three oxygen atoms, or nitrogen atoms, or a mixture thereof, in which each atom bonded to the terminal group (Y1A) or the linking group (Z) is an oxygen or nitrogen atom;

the terminal group (Y1A) is a (meth)acryloyl group, a $C_{1-20}$ monovalent hydrocarbon group or an active hydrogen atom, and a plurality of the terminal groups (Y1A) may be the same as or different from each other, with the proviso that among the terminal groups (Y1A) in the compound represented by the general formula (1A), three or more of the terminal groups are active hydrogen atoms or (meth)acryloyl groups, and one or more of the terminal groups are active hydrogen atoms; and the linking group (Z) is a divalent group represented by general formula (2), and when the compound represented by the general formula (1A) contains a plurality of the linking groups (Z), the linking groups (Z) may be the same as or different from each other;

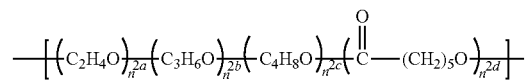
(2)

wherein in the general formula (2), $n^{2a}$, $n^{2b}$, $n^{2c}$ and $n^{2c}$ represent unit numbers of respective repeating units, and are each 0 to 100, a sum of $n^{2a}$, $n^{2b}$, $n^{2c}$ and $n^{2d}$ is 1 to 100, a left end of the group is bonded to the core (X), and a right end of the group is bonded to the terminal group (Y1A); and

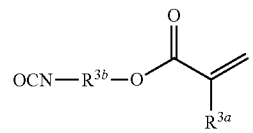
(3)

wherein in the general formula (3), $R^{3a}$ represents a hydrogen atom or a methyl group, $R^{3b}$ represents a $C_{2-6}$ linear alkylene group or a $C_{2-6}$ linear oxyalkylene group, and the linear alkylene group or the linear oxyalkylene group is optionally substituted with a $C_{1-6}$ alkyl group and/or a (meth)acryloyloxymethylene group in place of a hydrogen atom, under a condition of (total equivalents/moles of isocyanate groups present in the reaction derived from the compound represented by the general formula (3))/(total equivalents/moles of active hydrogen atoms of (Y1A) bonded to terminal oxygen atoms and nitrogen atoms of the core (X) present in the compound represented by general formula (1A))=1, wherein the compound (1A) is at least one selected from the group consisting of compounds represented by general formulas (6'a) to (6'k):

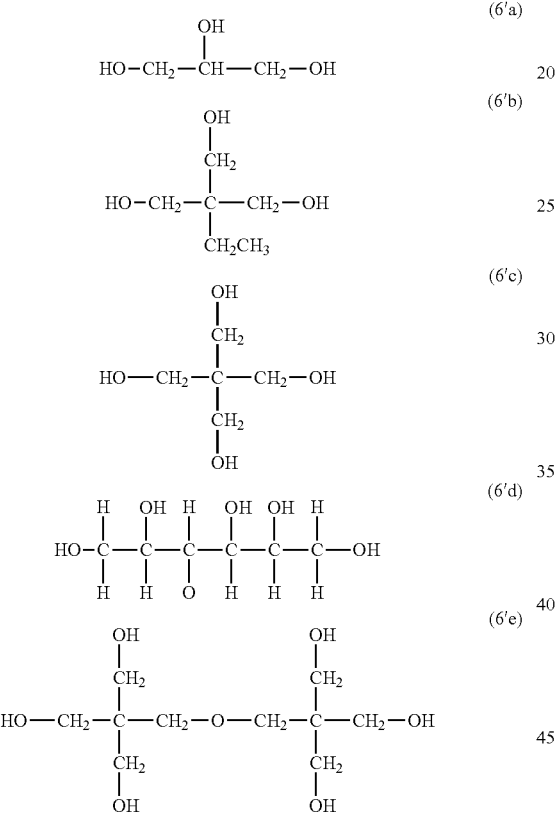

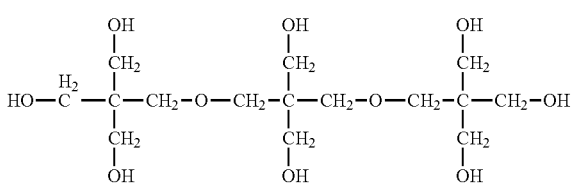

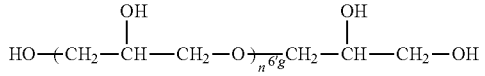

wherein in general formula (6'g), $n^{6'g}$ is an integer of 1 to 40,

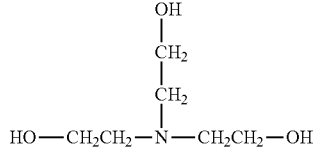

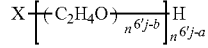

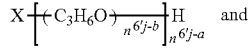

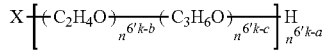

wherein $n^{6'i-a}$, $n^{6'j-a}$ and $n^{6'k-a}$ in the general formulas (6'i), (6'j) and (6'k) each represent a number of arms of a polyol bonded to the core X, and are each an integer of not less than 3; and $n^{6'i-b}$ and $n^{6'j-b}$ in the general formulas (6'i) and (6'j) represent numbers of oxyethylene units and oxypropylene units, respectively, and are each in the range of 1 to 100, the numbers of units for respective arms may be the same as or different from each other, $n^{6'k-b}$ and $n^{6'k-c}$ in the general formula (6'k) represent numbers of oxyethylene units and oxypropylene units, respectively, a sum thereof is in the range of 1 to 100, and the sums of the numbers of units for respective arms may be the same as or different from each other.

\* \* \* \* \*